US012746000B2

(12) United States Patent
Gustafson et al.

(10) Patent No.: US 12,746,000 B2
(45) Date of Patent: Sep. 29, 2026

(54) SOFT ANCHORS FOR ANATOMICAL FIXATION, AND RELATED SYSTEMS AND METHODS

(71) Applicant: Medos International Sarl, Le Locle (CH)

(72) Inventors: Adam Gustafson, Rehobeth, MA (US); Stephen Johnson, Johnston, RI (US); Thien Ngo, Mansfield, MA (US)

(73) Assignee: Medos International Sarl, Le Locle (CH)

( * ) Notice: Subject to any disclaimer, the term of this patent is extended or adjusted under 35 U.S.C. 154(b) by 49 days.

(21) Appl. No.: 18/920,183

(22) Filed: Oct. 18, 2024

(65) Prior Publication Data

US 2025/0160813 A1 May 22, 2025

Related U.S. Application Data

(60) Provisional application No. 63/600,355, filed on Nov. 17, 2023.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0409* (2013.01);
(Continued)

(58) Field of Classification Search
CPC ................ A61B 17/04; A61B 17/0401; A61B 2017/0409; A61B 2017/0458; A61B 2017/0461; A61B 2017/0464; A61F 2/08; A61F 2/0811; A61F 2002/0852; A61F 2002/0882
See application file for complete search history.

(56) References Cited

U.S. PATENT DOCUMENTS

| | | | | |
|---|---|---|---|---|
| 6,296,659 | B1 * | 10/2001 | Foerster | A61B 17/0469 623/13.13 |
| 7,905,904 | B2 | 3/2011 | Stone et al. | |

(Continued)

FOREIGN PATENT DOCUMENTS

| | | |
|---|---|---|
| CN | 113853170 | 12/2021 |

*Primary Examiner* — Vi X Nguyen
(74) *Attorney, Agent, or Firm* — Barnes & Thornburg LLP

(57) ABSTRACT

A tissue repair assembly can transition from an insertion to an anchored configuration and includes an anchor body, actuator, and "snake." The body and actuator comprise suture. The body defines a loop with length and width that decrease and increase, respectively, during transition to the anchored configuration. The actuator defines first and second actuation portions, the former defining a locking mechanism having knot loops within a distal interior passage of the body. The snake has a snake portion and first and second tails. In the insertion configuration: the snake portion extends through the knot loops; the second actuation portion and tails are outside the body. Tensioning the second actuation portion and/or tails transitions the assembly to the anchored configuration. The first tail can engage and pull the second actuation portion through the passage, wherein the second actuation portion is slidable through the knot loops and defines an exterior approximation loop.

16 Claims, 31 Drawing Sheets

(52) U.S. Cl.
CPC ................. *A61B 2017/0458* (2013.01); *A61B 2017/0461* (2013.01); *A61B 2017/0464* (2013.01); *A61F 2002/0852* (2013.01); *A61F 2002/0882* (2013.01)

(56) References Cited

U.S. PATENT DOCUMENTS

| | | | |
|---|---|---|---|
| 8,118,836 | B2 | 2/2012 | Denham et al. |
| 8,608,777 | B2 | 12/2013 | Kaiser et al. |
| 9,084,597 | B2 | 7/2015 | Arai et al. |
| 9,284,668 | B2 | 3/2016 | Johnson |
| 9,421,008 | B2 | 8/2016 | Burkhart et al. |
| 9,463,011 | B2 | 10/2016 | Dreyfuss et al. |
| 9,622,738 | B2 | 4/2017 | Dreyfuss et al. |
| 9,820,731 | B2 | 11/2017 | Arai et al. |
| 9,826,971 | B2 | 11/2017 | Lombardo et al. |
| 9,962,150 | B2 | 5/2018 | Rodriguez et al. |
| 10,182,806 | B2 | 1/2019 | Foerster |
| 10,383,619 | B2 | 8/2019 | Thal |
| 10,448,942 | B2 | 10/2019 | Santangelo et al. |
| 10,595,845 | B2 | 3/2020 | Burkhart et al. |
| 10,736,620 | B2 | 8/2020 | Dreyfuss et al. |
| 10,743,856 | B2 | 8/2020 | Durando |
| 10,952,719 | B2 | 3/2021 | Lombardo et al. |
| 10,966,705 | B2 | 4/2021 | Rodriguez et al. |
| 11,116,491 | B2 | 9/2021 | Burkhart et al. |
| 11,185,404 | B2 | 11/2021 | Kam et al. |
| 11,452,516 | B2 | 9/2022 | Gregoire et al. |
| 11,517,302 | B2 | 12/2022 | Lombardo et al. |
| 11,666,320 | B2 | 6/2023 | Johnson et al. |
| 2013/0296934 | A1* | 11/2013 | Sengun .............. A61B 17/0401 606/232 |
| 2015/0173739 | A1* | 6/2015 | Rodriguez ....... A61B 17/06166 606/232 |
| 2020/0138429 | A1 | 5/2020 | Dreyfuss et al. |
| 2020/0205799 | A1 | 7/2020 | Burkhart et al. |
| 2020/0214689 | A1 | 7/2020 | Bosworth et al. |
| 2021/0186484 | A1 | 6/2021 | Nason et al. |
| 2021/0244401 | A1 | 8/2021 | Burkhart et al. |
| 2021/0275290 | A1 | 9/2021 | Domecus et al. |
| 2022/0142637 | A1 | 5/2022 | Kehoe |
| 2022/0151602 | A1 | 5/2022 | Thal |
| 2022/0175514 | A1 | 6/2022 | Verma et al. |
| 2022/0240918 | A1 | 8/2022 | Qi et al. |
| 2022/0378409 | A1 | 12/2022 | Zenz-Olson et al. |
| 2023/0000480 | A1 | 1/2023 | Burkhart et al. |

* cited by examiner

SOFT ANCHORS FOR ANATOMICAL FIXATION, AND RELATED SYSTEMS AND METHODS

CROSS REFERENCE TO RELATED APPLICATIONS

This application claims the benefit under 35 U.S.C. § 119(e) of Provisional U.S. Patent Application No. 63/600, 355, filed Nov. 17, 2023, the entire contents of which are hereby incorporated by reference.

TECHNICAL FIELD

The present invention relates in general to devices, systems, and methods for approximating damaged tissue, and more particularly, to devices, systems and methods for anchoring a tissue repair assembly to a first anatomical structure and connecting the tissue repair assembly to a second anatomical structure for approximating the second anatomical structure with respect to the first anatomical structure.

BACKGROUND

Injuries to tissue such as cartilage, skin, muscle, bone, tendon and ligament, frequently require surgical intervention to repair the damage and facilitate healing. Surgical procedures to repair tissue damage are often performed using sutures connected to one or more anchoring device implanted in or adjacent to the damaged tissue. The sutures can also be passed through or around the tissue according to a variety of surgical techniques to secure the repair. The sutures can also interconnect two or more anchors used to perform the repair. Suture anchors have been fabricated with bodies formed from a variety of materials including nonabsorbable materials such as metals and durable polymers, as well as bioabsorbable materials such as absorbable polymers, bioceramics, absorbable composites and processed bone. Anchors that are themselves constructed entirely or at least substantially of suture material have been referred to as "all-suture anchors" or simply "suture anchors." and such anchors can be particularly advantageous in connection with certain types of tissue repair. Moreover, anchors that are themselves constructed entirely or at least substantially of textile suture material have been referred to as "soft anchors." Soft anchors display advantages in relation to fixation within bone material because the relatively soft and pliable nature of textile suture material allows soft anchors to generally fit within smaller pre-drilled holes in bone relative to other types of bone anchors, thus reducing the amount of bone that must be removed prior to anchor insertion.

SUMMARY

According to an embodiment of the present disclosure, an assembly for anatomical approximation is configured to transition from an insertion configuration to an anchored configuration and includes and anchor body, an actuation member, and a snake member. The anchor body is constructed of suture, defines an anchor loop, and has a length along a first direction and a width along a second direction that is substantially perpendicular to the first direction. The anchor body is configured so that the length decreases and the width increases as the assembly transitions from the insertion configuration to the anchored configuration. The actuation member is constructed of suture and defines a first actuation portion and a second actuation portion. The first actuation portion defines a locking mechanism within an interior passage defined by a distal portion of the anchor body. The locking mechanism comprises a plurality of knot loops. The snake member has a first snake portion and first and second snake tails. When the assembly is in the insertion configuration: the first snake portion extends along the interior passage and through the plurality of knot loops; the second actuation portion and the first and second snake tails are exterior of the anchor body; and at least one of the second actuation portion and the first and second snake tails is configured to receive a tensile force for transitioning the assembly from the insertion configuration to the anchored configuration. A free end region of the second snake tail is configured to couple with a free end region of the second actuation portion, such that a free end region of the first snake tail is configured to be pulled to draw the free end region of the second actuation portion into and through the interior passage of the anchor body, so that when the assembly is in a third configuration, the second actuation portion: 1) is gripped by and slidable relative to the plurality of knot loops within the interior passage, and 2) defines an approximation loop located exterior of the anchor body for approximating tissue.

According to another embodiment of the present disclosure, an instrument assembly for delivering a tissue repair assembly to a target site of an anatomical structure includes an insertion instrument and a tissue repair assembly carried by the insertion instrument while the tissue repair assembly is in an insertion configuration. The insertion instrument has a proximal end and a distal end spaced from each other along a longitudinal direction. The insertion instrument also has a handle portion at the proximal end and a fork at the distal end. The tissue repair assembly includes an anchor body, an actuation member, and a snake member. The anchor body is constructed of suture and defines an anchor loop. A distal portion of the anchor body is attachable to the fork between a pair of tines thereof. The anchor body defines a length along the longitudinal direction and a width along a lateral direction that is substantially perpendicular to the longitudinal direction. The anchor body is configured so that the length decreases and the width increases as the anchor body transitions from the insertion configuration to an anchored configuration of the tissue repair assembly. The actuation member is constructed of suture and defines a locking mechanism and at least one actuation tail extending away from the locking mechanism. The locking mechanism comprises a plurality of knot loops disposed within an interior passage of a distal portion of the anchor body. The snake member has a first snake portion and first and second snake tails. When the tissue repair assembly is in the insertion configuration: the first snake portion extends through the plurality of knot loops; the at least one actuation tail and the first and second snake tails are exterior of the anchor body and extend to one or more suture cleats of the handle portion; and one or more of the at least one actuation tail and the first and second snake tails is configured to receive a tensile force for transitioning the tissue repair assembly from the insertion configuration to the anchored configuration. The second snake tail is configured to couple with and pull the at least one actuation tail into the interior passage and through the plurality of knot loops so that a portion of the at least one actuation tail defines an approximation loop located exterior of the anchor body for approximating tissue.

According to an additional embodiment of the present disclosure, a method for approximating a second anatomical structure with respect to a first anatomical structure includes inserting an anchor body of a tissue repair assembly to a target location of the first anatomical structure. The anchor body is constructed of suture and defines an anchor loop. During the inserting step, an actuation member and a snake member are coupled to a distal portion of the anchor body and extend away from the anchor body. The actuation member defines a locking mechanism coupled to the distal portion of the anchor body. The locking mechanism comprises a plurality of knot loops disposed within an interior passage of the distal portion of the anchor body. The method includes tensioning at least one of the actuation member and the snake member in a manner causing a length of the anchor body to decrease and a width of the anchor body to increase; and coupling a free end region of the actuation member with a free end region of the snake member, such that the coupled actuation member and the snake member form a loop, wherein at least a portion of the second anatomical structure extends through the loop. The method includes pulling a second free end region of the snake member in a direction away from the anchor body, thereby pulling the coupled free end region of the actuation member through the plurality of knot loops, such that the actuation member itself forms an approximation loop through which the at least a portion of the second anatomical structure extends. The method also includes pulling the free end region of the actuation member away from the plurality of knot loops, thereby reducing a circumference of the approximation loop.

BRIEF DESCRIPTION OF THE DRAWINGS

The foregoing summary, as well as the following detailed description of illustrative embodiments of the present application, will be better understood when read in conjunction with the appended drawings. For the purposes of illustrating the features of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

Figure 1A:
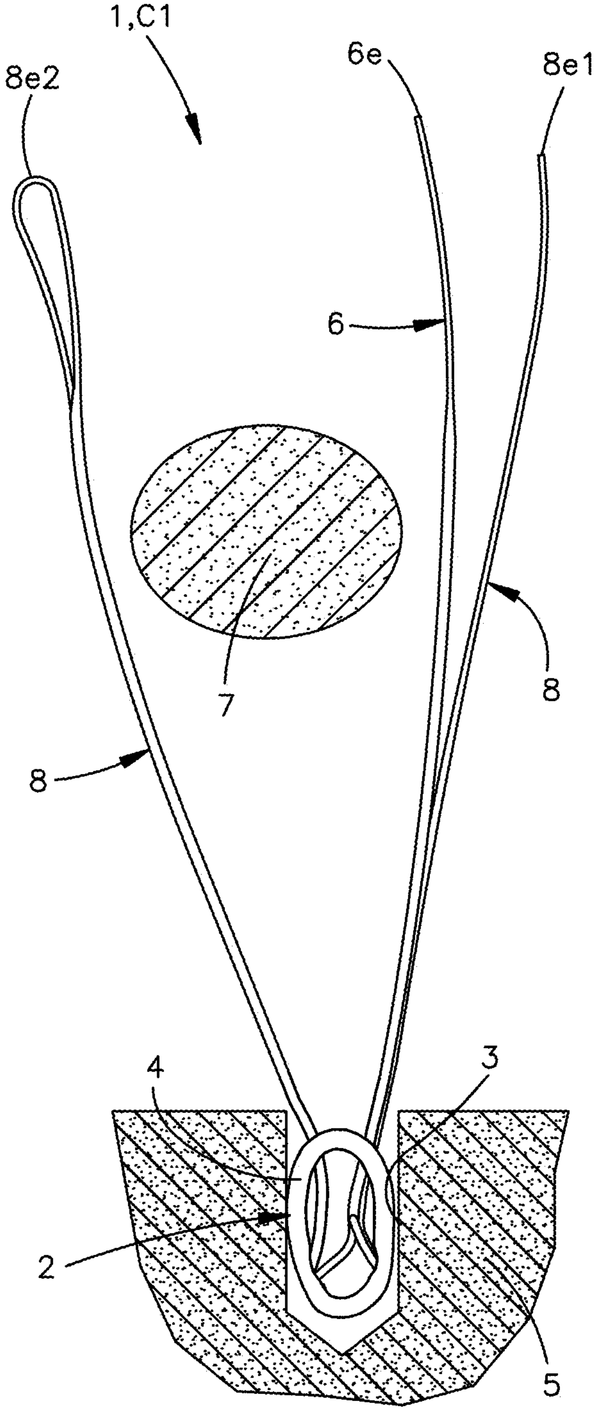
FIG. 1A is a front plan view of a tissue repair assembly shown in an insertion configuration, the tissue repair assembly includes an anchor body and also includes an operative or "actuation" member and a utility or "snake" member coupled to and extending from the anchor body, wherein the anchor body and portions of the utility member and snake member extending along the anchor body are constructed of textile suture material(s) and collectively define a "soft anchor" of the tissue repair assembly, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "about" and "substantially", as used herein with respect to dimensions, angles, ratios, and other geometries, takes into account manufacturing tolerances. Further, the terms "about" and "substantially" can include 10% greater than or less than the stated dimension, ratio, or angle. Further, the terms "about" and "substantially" can equally apply to the specific value stated.

As used herein with reference to anatomical repair, the terms "approximate", "approximating", "approximated", and derivatives thereof, refer to action(s) by which a distance between respective anatomical structures is reduced. It should be appreciated that these terms and their derivatives as used herein do not infer which particular anatomical structure(s) move with respect to other anatomical structure (s) unless expressly stated otherwise. For example, as used herein, the exemplary phrase "the second anatomical structure is approximated with respect to the first anatomical structure" does not inherently mean that the second anatomical structure moves while the first anatomical structure remains stationary; although the exemplary phrase can indeed encompass the foregoing, it can also encompass action(s) in which the first anatomical structure moves while the second anatomical structure remains stationary and it can further encompass action(s) in which both the first and second anatomical structures move (e.g., toward each other).

It should be understood that, although terms involving numerical prepositions (e.g., "first," "second," "third") can be used herein to describe various features, such features should not be limited by these terms. These terms are instead used to distinguish one feature from another. For example, a first element could be termed a second element or a third element in another context, and, similarly, a second element could be termed a first element or a third element in another context, without departing from the scope of the embodiments disclosed herein.

The embodiments disclosed herein pertain to soft anchors for use with tissue repair assemblies, particularly for tissue approximation. The soft anchors disclosed herein provide numerous advantages over many prior art soft anchors. For example, the soft anchors disclosed herein are configurable to have a narrow profile when in an insertion configuration (such as when loaded on an insertion instrument), which narrow profile includes a tapered distal geometry, and which narrow profile reduces friction with bone material during anchor insertion within a pre-formed tunnel or hole in bone. The soft anchors disclosed herein also transition from their narrow insertion configuration to an "anchored" (i.e., bunched-up) configuration, in which the maximum width of the soft anchors have increased significantly, which facilitates secure affixation with the bone. Additionally, when in their anchored configurations, the soft anchors disclosed herein present broad proximal faces at or adjacent their proximal ends, which, when combined with their increased maximum widths, further secures affixation with the bone and prevents pullout. The soft anchors disclosed herein also provide each anchor with a proximal barrier-like formation that mechanically interferes with or otherwise impedes the locking mechanism or other distal portions of the anchor from migrating proximally from the remainder of the anchor. Additionally, such mechanical interference has been observed to impede, or at least reduce the chances of, unwanted affects stemming from proximal migration (such as anchor prominence or tenting at the outer bone surface, and/or laxity in an approximation loop coupled to the anchor). Some of the soft anchors disclosed herein are also configured so that, as they transition to their anchored configurations, they collapse longitudinally (i.e., along the direction in which they were inserted into the hole), beginning at their distal ends and collapsing proximally, and in smooth, rapid longitudinal anchor collapse sequence that terminates when the collapsing portions of the anchors encounter mechanical interference with the barrier-like proximal portions of the anchors, which provides an abrupt stop to the longitudinal collapse sequence, thereby providing enhanced tactile feedback to the user indicating that the soft anchor has successfully anchored within the bone.

Figure 1B:
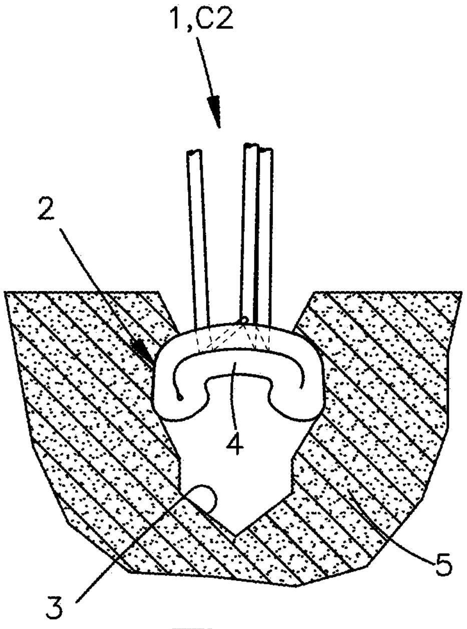
FIG. 1B is front plan view of the soft anchor illustrated in FIG. 1A, shown in an anchored configuration.
Figure 1C:
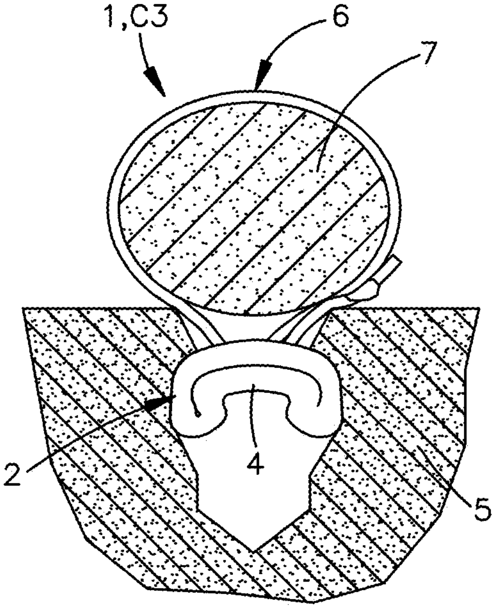
FIG. 1C is a front plan view of the tissue repair assembly illustrated in FIG. 1A, shown in an approximated configuration.

Referring to FIG. 1A, an exemplary tissue repair assembly 1 for anatomical approximation includes an anchor body 4, an operative or "actuation" member 6 that is coupled to the anchor body 4, and a utility or "snake" member 8 that is temporarily coupled to the anchor body 4. A distal portion of the repair assembly 1, particularly the anchor body 4 and the respective portions of the actuation member 6 and the snake member 8 extending alongside and/or within the anchor body 4, define an anchor unit 2 of the repair assembly 1. The anchor unit 2 can be referred to simply as an "anchor" 2. Due to the construction of its constituent members (described in more detail below), the anchor 2 can be characterized as a "soft" anchor 2. In the exemplary embodiments disclosed herein, the repair assembly 1 is particularly configured for anatomical approximation of (i.e., reducing a distance between) a first anatomical structure 5 and a second anatomical structure 7. In particular, the anchor body 4 is configured to affix the repair assembly 1 to a target location 3 of the first anatomical structure 5. The actuation member 6 extends from the anchor body 4 and is configured to connect the repair assembly 1 to the second anatomical structure 7, and the snake member 8 is configured to couple with and shuttle a free end 6*e* of the actuation member 6 through a locking mechanism attached to the anchor body 4, whereby the actuation member 6 forms an approximation loop around the second anatomical structure 7. With the approximation loop in place, the actuation member 6 can be employed for approximating at least one of the first anatomical structure 5 and the second anatomical structure 7 toward the other. For such purposes, the soft anchor 2 of the repair assembly 1 is adapted for insertion to the target location 3 of the first anatomical structure 5 while the repair assembly 1 is in a first or insertion configuration C1, as shown in FIG. 1A. The repair assembly 1, and particularly the anchor 2 thereof, is also configured to transition from the insertion configuration to a second or anchored configuration C2, in which the anchor body 4 affixes to the target location 3, as shown in FIG. 1B. The repair assembly 1 is further configured to transition to a third or approximated configuration C3 in which the first and second anatomical structures 5, 7 are approximated, as shown in FIG. 1C.

The first and second anatomical structures 5, 7 can include bone and/or soft tissue (e.g., cartilage, ligament, and/or tendon, by way of non-limiting examples). For example, as shown in FIGS. 1A-1C, the first anatomical structure 5 can include bone, the second anatomical structure 7 can include soft tissue, and the repair assembly 1 can be employed to approximate the soft tissue to the bone. In one such particular technique, the repair assembly 1 can be employed to repair a torn labrum of the shoulder. In this particular example, the first anatomical structure 5 can be the glenoid 5 of the shoulder and the second anatomical structure 7 can be a torn portion of the labrum 7. For example, the anchor body 4 can be inserted and affixed within a pre-drilled hole 3 formed the glenoid 5, the actuation member 6 can connect to the torn portion of the labrum 7, and the snake member 8 can be employed to pull the free end 6*e* of the actuation member 6 through the anchor body 4 to approximate (i.e., reduce a distance between) the torn portion of the labrum 7 and the glenoid 5. It should be appreciated that various other tissue repairs can be performed using the repair assembly 1 described herein, such as ACL repair, ankle instability repair, Achilles tendon repair, rotator cuff repair, extracapsular knee ligament reconstructions/repair (e.g., MPFL, MCL, LCL, ALL), iliotibial band (ITB) tenodesis, biceps tenodesis, and knee meniscus repair, by way of additional non-limiting examples. It should also be appreciated that the target location 3 of the first anatomical structure 5 need not be a hole formed therein. For example, the first target location 3 could be located adjacent an exterior surface of the first anatomical structure 5.

Figure 2B:
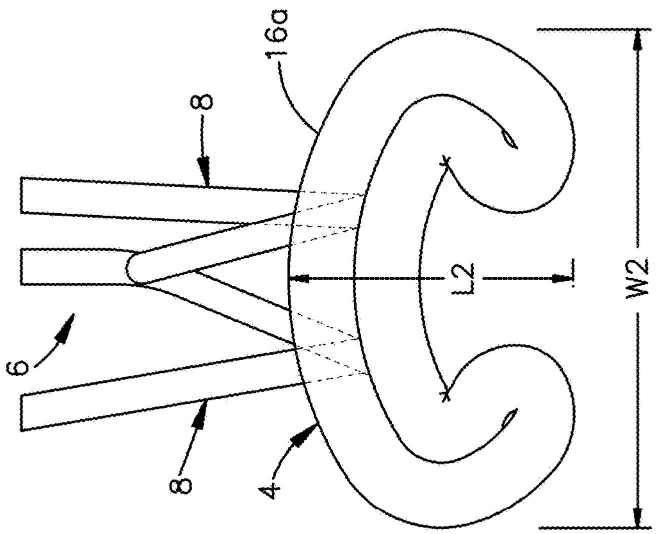
FIGS. 2A-2B are enlarged front plan views of the soft anchor illustrated in FIGS. 1A-1B, particularly showing the soft anchor in the insertion configuration (FIG. 2A) and in the anchored configuration (FIG. 2B)
Figure 2A:
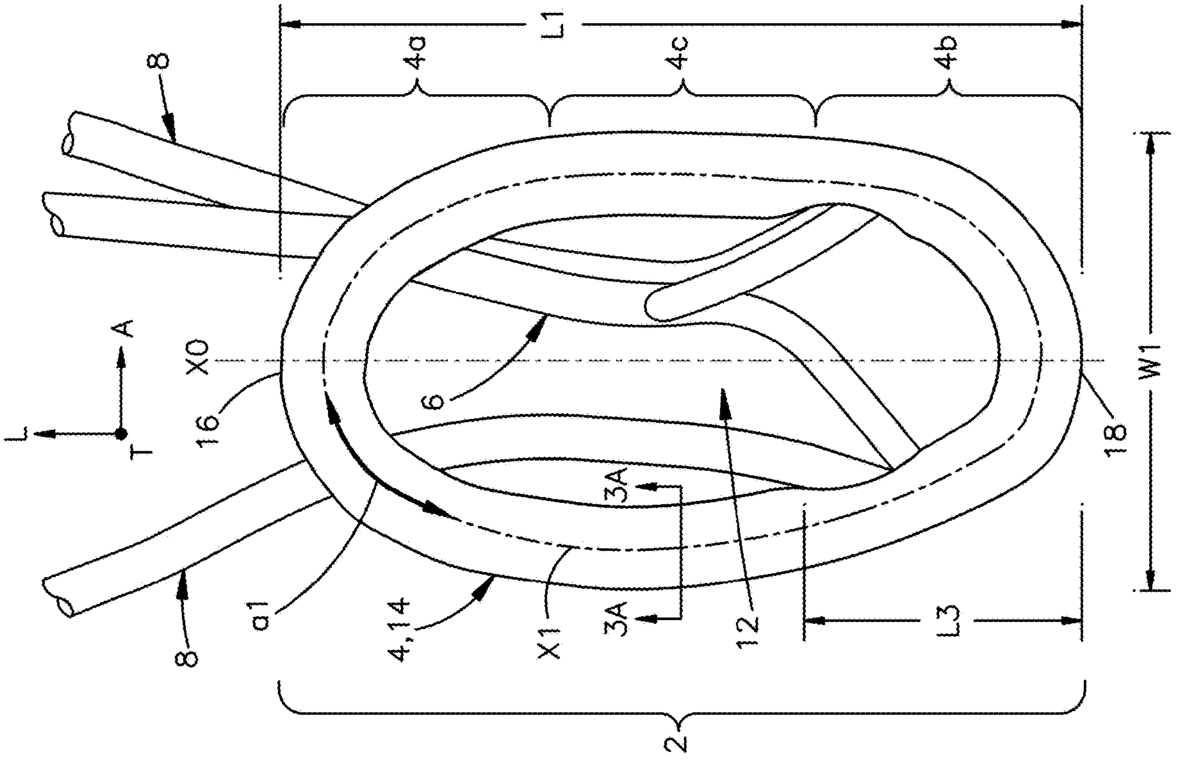

Referring now to FIG. 2A, the soft anchor 2 is shown in the insertion configuration C1. The anchor body 4 defines and extends along a central body axis X1 and is arranged into a shape. The central body axis X1 extends along an axial direction al. In the illustrated embodiment, the shape of the anchor body 4 is a loop, which can be referred to as an anchor loop 14, and which is preferably a closed loop that defines an interior anchor eyelet 12. Accordingly, the central body axis X1 is also arranged in a loop (e.g., a closed loop) in such embodiments. It should be appreciated that the anchor body 4 can be arranged into other shapes in the insertion configuration, such as a V-shape, U-shape, horseshoe shape, and hourglass-like shape, by way of non-limiting examples, which such other shapes can but need not define an interior anchor eyelet.

The anchor body 4 has a trailing or proximal end 16 and a leading or distal end 18 spaced from each other along a longitudinal direction L that is oriented along an axis of insertion X0 (also referred to herein as the "insertion axis" X0) into patient anatomy. In particular, the distal end 18 is spaced from the proximal end 16 in a distal direction D, which is oriented along the longitudinal direction L. The proximal end 16 is spaced from the distal end 18 in a proximal direction P, which is opposite the distal direction D and is also oriented along the longitudinal direction L. It should be appreciated that the proximal and distal directions P, D are mono-directional components of the longitudinal direction L, which is bi-directional. It should also be appreciated that, as used herein: the terms "longitudinal", "longitudinally", and derivatives thereof refer to the longitudinal direction L; the terms "proximal", "proximally", and derivatives thereof refer to the proximal direction P; and the terms "distal", "distally", and derivatives thereof refer to the distal direction D.

The anchor body 4 defines a proximal portion 4*a* and a distal portion 4*b* that are longitudinally spaced from each other. The proximal portion 4*a* extends distally from the proximal end 16 toward the distal portion 4*b*. The distal portion 4*b* extends proximally from the distal end 18 toward the proximal portion 4*a*. The anchor body 4 can also define an intermediate portion 4*c* located longitudinally between the proximal and distal portions 4*a,b*. The actuation member 6 is coupled to the anchor body 4 preferably at the distal portion 4*b* thereof. Additionally, the snake member 8 is also preferably coupled to the anchor body 4 at the distal portion 4*b* thereof when in the insertion configuration C1.

Referring now to FIGS. 2A-2B, the anchor body 4 defines a length along the longitudinal direction L and a width along a lateral direction A that is substantially perpendicular to the longitudinal direction L. The anchor body 4 also defines a thickness along a transverse direction T that is substantially perpendicular to the longitudinal and lateral directions L, A. It should be appreciated that, as used herein: the terms "lateral", "laterally", and derivatives thereof refer to the lateral direction A; and the terms "transverse", "transversely", and derivatives thereof refer to the transverse direction T. As mentioned above, the anchor body 4 is configured to be inserted to the target location 3 of the first anatomical structure 5 when in the insertion configuration C1 (FIG. 2A). When in the anchored configuration (FIG. 2B), the anchor body 4 is configured to affix to the target location 3. In particular, the repair assembly 1 is configured to transition from the insertion configuration C1 to the anchored configuration C2 responsive to (i.e., as a response to, or, as caused by) tensile force(s) applied to one or more of the actuation member 6 and the snake member 8. In the illustrated embodiment, transitioning the repair assembly 1 to the anchored configuration C2 is preferably actuated by applying tensile forces to the free end 6*e* of the actuation member 6 and to opposite ends 8*e*1, 8*e*2 of the snake member 8 generally in the proximal direction P (which ends 6*e*, 8*e*1, 8*e*2 are shown in FIG. 1A). The approximated configuration C3 is discussed in more detail below. It should be appreciated that the anchor body 4 remains anchored with respect to the first anatomical structure 5 during and after the repair assembly 1 transitions to the approximated configuration C3. Accordingly, the approximated configuration C3 can be characterized as a latter stage of the anchored configuration C2.

As the repair assembly 1 transitions from the insertion configuration C1 to the anchored configuration C2, the anchor body 4 is particularly configured to bunch-up such that its length decreases and its width increases. This allows the anchor body 4 to have a narrower width in the insertion configuration, which facilitates inserting the anchor body 4 into the target location 3 (such as the hole 3 formed in the bone 5), and to thereafter transition to the anchored configuration in which the width is increased, which facilitates rigid fixation to the anatomical structure (e.g., within the hole 3 in the bone 5). In particular, in the insertion configuration (FIG. 2A), the anchor body 4 defines a first maximum width W1 along the lateral direction A and a first maximum length L1 along the longitudinal direction L. In the anchored configuration (FIG. 2B), the anchor body 4 defines a second maximum width W2 along the lateral direction A and a second maximum length L2 along the longitudinal direction L, wherein the second maximum width W2 is greater than the first maximum width W1 and the second maximum length L2 is less than the first maximum length L1. The anchor body 4 has been observed to present a broad proximal face 16*a* at or adjacent the proximal end 16, which enhances anchoring within bone and reduces the chances of pullout, which is particularly advantageous when anchoring to harder cancellous bone material. It is to be appreciated that the first and second maximum widths W1, W2 each refers to a total width of the anchor body 4 with respect to the lateral direction A, and is not to be limited to widths measured between two opposite points on the anchor body 4 that intersect a single linear axis orientated along the lateral direction A. For instance, the locations of the anchor body 4 that define a maximum width can be spaced from each other along the longitudinal direction L. It should be appreciated that, as used herein, the terms “bunch”, “bunching”, “bunch up”, “bunch together”, and their derivatives refers to an action whereby at least a portion of the anchor body 4 is forced toward expanding along the lateral direction A in response to a shortening force along the longitudinal direction L. It should also be appreciated that the maximum thickness of the anchor body 4 along the transverse direction T also preferably increases as the anchor body 4 transitions from the insertion configuration C1 to the anchored configuration C2.

Figure 3A:
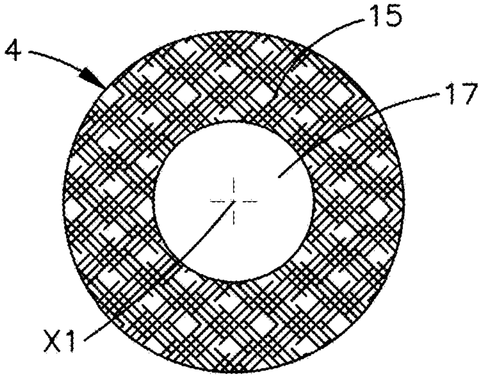
FIGS. 3A-3C are respective axial sectional views of the anchor body (FIG. 3A) (taken along section line 3A-3A in FIG. 2A), the actuation member (FIG. 3B), and the snake member (FIG. 3C) of the soft anchor illustrated in FIG. 2A, taken along respective planes orthogonal to the central axes of the anchor body, actuation member, and snake member.

The anchor body 4 is preferably constructed of suture material, particularly textile suture material(s). Accordingly, the anchor body 4 contributes greatly to the anchor 2 being characterized as a “soft anchor.” Referring now to FIG. 3A, in such embodiments, the anchor body 4 includes a textile construct or “jacket” 15 that defines an interior core space 17, which can be centrally located along the anchor body 4 such that the central body axis X1 extends along the core space 17. The jacket 15 is preferably constructed of a plurality of fibers of suture material, which are braided or otherwise woven or intertwined together in a manner that defines the jacket 15. In the illustrated embodiment, the plurality of suture fibers are braided together in a circular braiding pattern that provides the jacket 15 with a generally circular cross-sectional profile. In other embodiments, the jacket 15 can have a flat or “tape”-like cross-sectional profile or yet other cross-sectional profiles, including those described more fully in U.S. Pat. No. 11,666,320, issued Jun. 6, 2023, in the name of Johnson, et al. (“the ’320 Reference”), the entire disclosure of which is hereby incorporated by reference herein. The fibers of the textile suture material of the jacket 15 can have a material composition that includes one or more of polyethylene terephthalate (PET, e.g., ETHIBOND® brand polyester suture produced by Ethicon, Inc. of Bridgewater, New Jersey, USA), ultra-high-molecular-weight polyethylene (UHMWPE), polydioxanone (PDS), polypropylene (PP), and nylon, for example. The jacket fibers can be monofilament or multi-filament fibers, and can be employed with or without colorants as desired. In the illustrated embodiment, the interior core space 17 of the anchor body 4 is generally devoid of anchor body 4 material, although in other embodiments, the anchor body 4 can include a core member that extends within and along the interior core space 17. It should be appreciated that such core member(s) can include swellable material, such as those disclosed in the ’320 Reference.

Figure 3B:
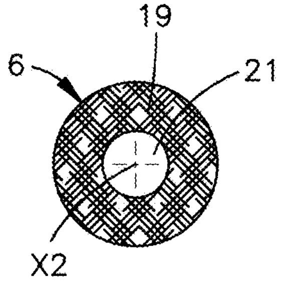
Figure 3C:
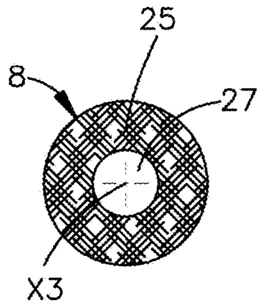

Referring now to FIGS. 3B-3C, the actuation member 6 and the snake member 8 are also preferably constructed of suture material, particularly textile suture material(s). In such embodiments, the actuation member 6 and the snake member 8 each have a respective textile construct or “jacket” 19, 25 that defines a respective interior core space 21, 27, which can be centrally located along a central actuation member axis X2 and a central snake member axis X3, respectively. The jackets 19, 25 of the actuation member 6 and snake member 8 are preferably constructed of a plurality of fibers of suture material, which are braided or otherwise woven or intertwined together in a manner that defines the jackets 19, 25. In the illustrated embodiment, the plurality of suture fibers are braided together in a circular braiding pattern that provides the jackets 19, 25 with generally circular cross-sectional profiles. In other embodiments, the jackets 19, 25 of one or both of the actuation member 6 and the snake member 8 can have a flat or “tape”-like cross-sectional profile or yet other cross-sectional profiles, including those described more fully in the ’320 Reference. The fibers of the textile suture material of the jackets 19, 25 of the actuation member 6 and snake member 8 can have a material composition including those described above with reference to the jacket 15 of the anchor body 4. In the illustrated embodiment, at least a majority of the interior core spaces 21, 27 of the actuation member 6 and the snake member 8 are devoid of material, which facilitations various manipulations, adaptations, and constructions made or makable to one or more portions of the actuation member 6 and the snake member 8, such as splices and the like, as described in more detail below. However, in other embodiments, one or more portions of the actuation member 6 and/or the snake member 8 can include one or core members that extends within and along the interior core spaces 21, 27 thereof, which core member(s) can include swellable material, such as those disclosed in the ’320 Reference.

In one non-limiting exemplary embodiment of the repair assembly 1, the anchor body 4 is constructed of textile suture materials including #5 size UHMWPE braided with PET tracers, the actuation member 6 is constructed of textile suture materials including #1 size UHMWPE, and the snake member 8 is constructed of textile suture materials including a #1 size co-braid of UHMWPE and PET. It should be appreciated that various other textile suture material compositions, sizes, and constructions can be employed for the anchor body 4, actuation member 6, and snake member 8, respectively.

Figure 4A:
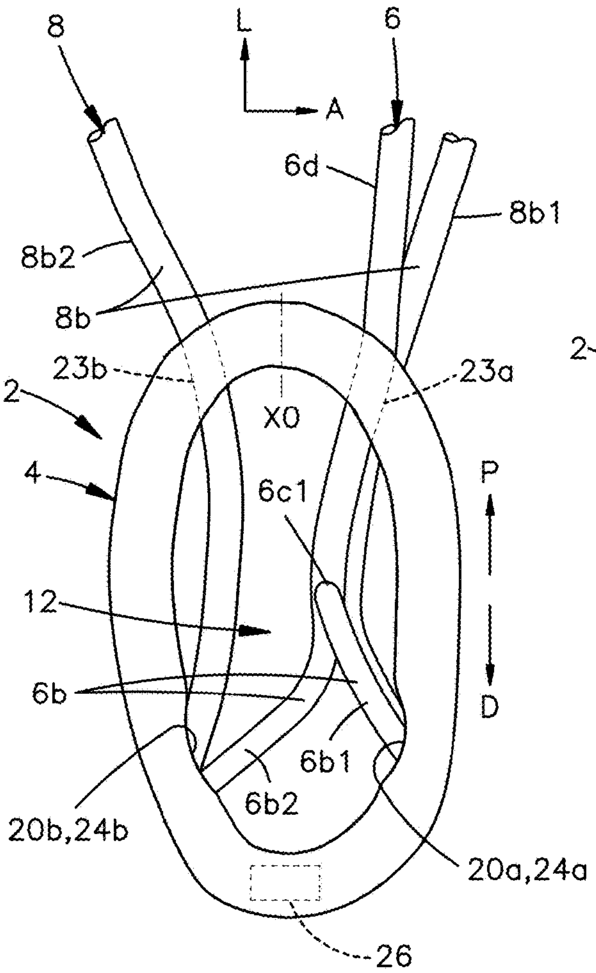
FIGS. 4A and 4B are respective front and back plan views of the soft anchor illustrated in FIG. 2A.
Figure 4B:
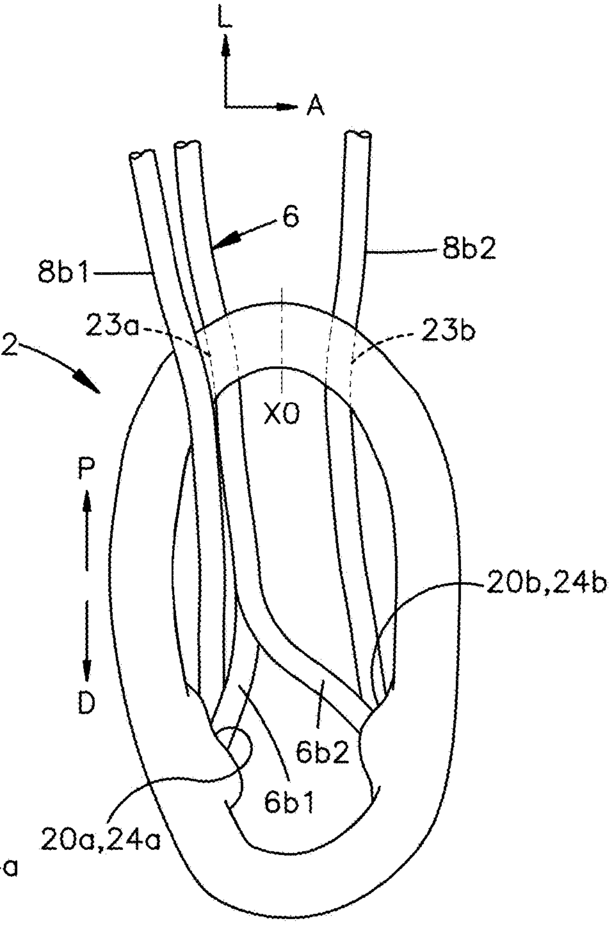
Figure 4C:
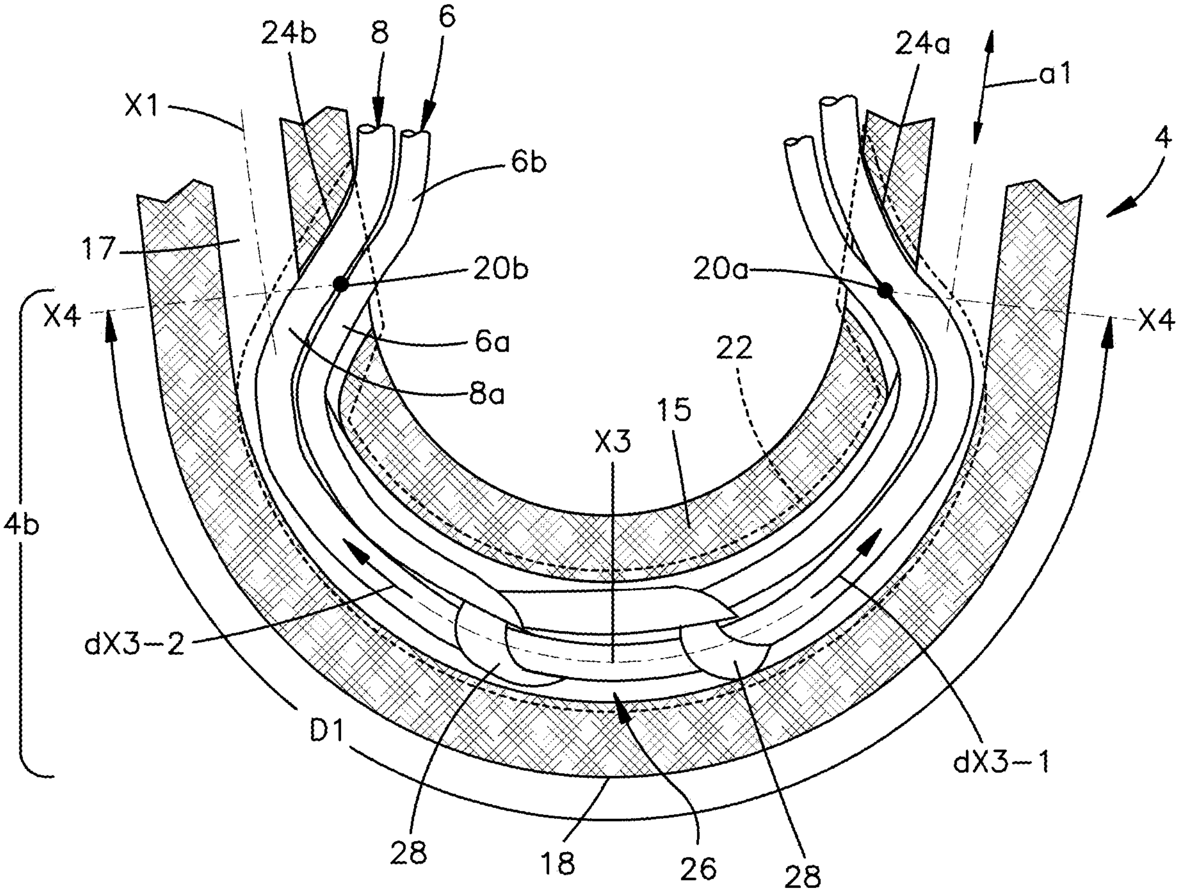
FIG. 4C is an enlarged, partial section view of a distal portion of the soft anchor illustrated in FIG. 4A.

Referring now to FIGS. 4A-4C, one or both of the actuation member 6 and the snake member 8 can be coupled with the distal portion 4*b* of the anchor body 4 via being spliced with the distal portion 4*b*. For example, in the illustrated embodiment, both the actuation member 6 and the snake member 8 enter an interior passage 22 of the anchor body 4 at a first location 20*a* thereof and exit the interior passage at a second location 20*b* of the anchor body 4. In the illustrated embodiment, the interior passage 22 includes the interior core space 17 of the anchor body 4. In particular, as shown in FIG. 4C, the actuation member 6 and the snake member 8 enter the interior passage 22 through a first penetration 24*a* through the jacket 15 at the first location 20*a*, and extend alongside one another through a portion of the interior core space 17 along the axial direction al of the anchor body 4, and exit the interior passage 22 through a second penetration 24*b* through the jacket 15 at the second location 20*b*. Thus, in the illustrated embodiment, the first penetration 24*a* is positioned at the first location 20*a*, and the second penetration 24*b* is positioned at the second location 20*b*. Accordingly, the actuation member 6 and the snake member 8 can be said to penetrate the jacket 15 at the first and second locations 20*a,b*. In this example, the interior passage 22 includes the first and second penetrations 24*a,b* and the portion of the interior core space 17 extending therebetween.

For purposes of this disclosure, the distal portion 4*b* of the anchor body 4 is defined as the portion thereof that defines the interior passage 22 through which the actuation member 6 and the snake member 8 extend. Accordingly, the distal portion 4*b* of the anchor body 4 can be characterized as that portion that extends distally from a proximal-most one of the first and second locations 20*a,b* to the distal end 18 of the anchor body 4. Preferably, the first and second locations 20*a,b* are equidistantly spaced from the distal end 18 of the anchor body 4 along the longitudinal direction L, which facilitates a predictable bunching pattern for the anchor body 4 as it transitions to the anchored configuration. In other embodiments, however, the first and second locations 20*a,b* can be spaced from each other along the longitudinal direction L (i.e., the first and second locations 20*a,b* can be longitudinally non-equidistant from the distal end 18 of the anchor body 4).

Referring again to FIG. 2A, the distal portion 4*b* of the anchor body 4 defines a distal portion length L3 along the longitudinal direction L. The distal portion length L3 is preferably from about 80% to about 5.0% of the first maximum length L1 of the anchor body 4, and more particularly about 40% to about 20% of the first maximum length L1, and more particularly about 28% to about 32% of the first maximum length L1. Stated differently, a ratio of the distal portion length L3 to the first maximum length L1 (i.e., L3:L1) can be in a range from about 0.80:1 to about 0.05:1, and more particularly from about 0.40:1 to about 0.20:1, and more particularly from about 0.32:1 to about 0.28:1.

Referring again to FIG. 4C, the interior passage 22 has a passage length D1 (which, in this example, can also be referred to as a "splice length" D1) measured between the first and second locations 20*a,b* along the central body axis X1. For measurement purposes, the first and second locations 20*a,b* can be defined as the locations at which respective reference axes X4, which extend from the geometric centers of the first and second penetrations 24*a,b*, intersect the central body axis X1 in perpendicular fashion. The passage length D1 can be in a range of about 6.0 mm to about 16.0 mm, and more particularly in a range of about 11.0 mm to about 14.0 mm, and more particularly in a range of about 12 mm to about 13 mm.

Referring again to FIGS. 4A-4C, it should be appreciated that, when the repair assembly 1 is in the insertion configuration C1: the actuation member 6 includes at least one first portion 6*a* that resides within and extends along the interior passage 22 of the anchor body 4 and at least one second portion 6*b* that is exterior of the anchor body 4; and the snake member 8 includes at least one first portion 8*a* that resides within and extends along the interior passage 22 of the anchor body 4 and at least one second portion 8*b* that is exterior of the anchor body 4. These first portions 6*a*, 8*a* of the actuation member 6 and the snake member 8 can be referred to as the "first actuation portion" 6*a* and the "first snake portion" 8*a*, respectively, and those second portions 6*b*, 8*b* of the actuation member 6 and the snake member 8 can be referred to as the "second actuation portion" 6*b* and the "second snake portion" 8*b*, respectively. The second actuation portion 6*b* and the second snake portion 8*b* can each include a pair of tails 6*b*, 8*b*, which can be referred to as "actuation tails" 6*b* and "snake tails" 8*b*, respectively, and which extend proximally from the distal portion 4*b* of the anchor body 4. The actuation tails 6*b* and the snake tails 8*b* extend proximally from the first and second penetrations 24*a,b* to respective proximal actuation tail ends (at least one of which defines the free end 6*e*) and respective first and second snake tail ends 8*e*1, 8*e*2, which are shown in FIG. 1A, and are described in more detail below.

As shown in FIGS. 4A-4B, the pair of actuation tails 6*b* includes a first actuation tail 6*b*1 and a second actuation tail 6*b*2; and the pair of snake tails 8*b* includes a first snake tail 8*b*1 and a second snake tail 8*b*2. In the illustrated embodiment, the first actuation tail 6*b*1 and the first snake tail 8*b*1 extend proximally from the first penetration 24*a*; and the second actuation tail 6*b*2 and the second snake tail 8*b*2 extend proximally from the second penetration 24*b*. It should be appreciated that the first and second actuation tails 6*b*1, 6*b*2 and the first and second snake tails 8*b* extend proximally from the first and second penetrations 24*a,b*, and within the anchor eyelet 12 (or at least within a profile of the anchor eyelet 12 in a reference plane extending along the longitudinal and lateral directions L, A (which reference plane can be referred to as an L-A reference plane)). From the anchor eyelet 12 (or at least from the profile thereof), the first and second actuation tails 6*b*1, 6*b*2 and the second snake tail 8*b*2 pass through the proximal portion 4*a* of the anchor body 4, and the first snake tail 8*b*1 passes alongside the proximal portion 4*a* of anchor body 4. In the illustrated embodiment, the first and second actuation tails 6*b*1, 6*b*2 pass through a first proximal penetration 23*a* through the proximal portion 4*a* of the anchor body 4; the second snake tail 8*b*2 passes through a second proximal penetration 23*b* through the proximal portion 4*a* of the anchor body 4; and the first snake tail 8*b*1 passes alongside the proximal portion 4*a* of the anchor body 4. In this embodiment, the first and second proximal penetrations 23*a,b* are at opposite lateral positions about the insertion axis X0. Preferably, the first and second proximal penetrations 23*a,b* are substantially equidistant from the insertion axis X0 along the lateral direction A, although alternatively the first and second proximal penetrations 23*a,b* need not be equidistantly laterally spaced from the insertion axis X0. Moreover, in the illustrated embodiment, the first snake tail 8*b*1 passes alongside the proximal portion 4*a* of the anchor body 4 at a location substantially adjacent the first proximal penetration 23*a*. In other embodiments, the first snake tail 8*b*1 can pass through the first proximal penetration 23*a* together with the actuation tails 6*b*1, 6*b*2. In yet other embodiments, the second snake tail 8*b*2 can pass alongside the proximal portion 4*a* of the anchor body 4 (instead of through a penetration through the proximal portion 4*a*). In yet additional embodiments, two or more and up to all of the actuation tails 6*b*1, 6*b*2 and the snake tails 8*b*1, 8*b*2 can pass alongside the proximal portion 4*a* of the anchor body 4.

With continued reference to FIGS. 4A-4B, the actuation tails 6*b* can be coupled together to provide a joined actuation tail 6*d* that extends to the free end 6*e* of the actuation member 6. In the illustrated embodiment, the actuation tails 6*b* are coupled together via splicing from a first or distal joint location 6*c*1 to a second or proximal joint location 6*c*2 (shown in FIG. 4E). For example, one of the actuation tails 6*b*1, 6*b*2 can be bury spliced into the other of the actuation tails 6*b*2, 6*b*1 so as to provide a spliced actuation portion 6*g*, which extends proximally from the first joint location 6*c*1 (see FIG. 4A), which is a splice insertion point, to the second joint location 6*c*2 (see FIG. 4E), which is the end of the splice. Accordingly, the first joint location 6*cl* can be referred to as the "splice insertion point" 6*c*1, and the second joint location 6*c*2 can also be referred to as the "splice end" 6*c*2. It should also be appreciated that, as used herein, the term "bury splice" and derivatives thereof (e.g., "bury spliced" and "bury splicing") refers to a suture construct in which a first length of suture penetrates the jacket of a second length of suture and extends longitudinally within and along an interior of the second length of suture in a substantially parallel arrangement, and in which the first length of suture terminates within the interior of the second length. The aforementioned substantially parallel arrangement of the bury splice can include co-axial alignment of the first and second lengths of suture (such as when the first length of suture extends within and along the core space of the second length of suture). In the illustrated embodiment, the first actuation tail 6*b*1 penetrates within the jacket 19 of the second actuation tail 6*b*2 at the splice insertion point 6*c*1. Thus, along the spliced actuation portion 6*g*, the jacket 19 of the first actuation tail 6*b*1 resides in an interior of the jacket 19 of the second actuation tail 6*b*2 (such as within the core space 21 of the second actuation tail 6*b*2). Accordingly, along the spliced actuation portion 6*g*, the jackets 19 of the first and second actuation tails 6*b*1 can be referred to as the "interior" and "exterior" jackets 19, respectively. It should be appreciated that, in the illustrated embodiment, the terminal end of the first actuation tail 6*b*1 defines the splice end 6*c*2.

The first joint location 6*c*1 (i.e., the splice insertion point) of the actuation member 6 is preferably located within the anchor eyelet 12 (or at least within a profile of the anchor eyelet 12) with respect to the longitudinal and lateral directions L, A when in the insertion configuration C1. Preferably the first joint location 6*c*1 is substantially positioned at the longitudinal midpoint of the anchor body 4 (i.e., at about one-half of the first maximum length L1, or at a ½ L1 position). The first joint location 6*c*1 is also preferably laterally offset toward a first one of the snake tails 8*b*1 (also referred to as the "first snake tail" 8*b*1) and away from a second one of the snake tails 8*b*2 (also referred to as the "second snake tail" 8*b*2). Stated differently, the first joint location 6*c*1 is preferably proximate the first snake tail 8*b*1 and remote from the second snake tail 8*b*2. This allows the joined actuation tail 6*d* to extend alongside the first snake tail 8*b*1 in the proximal direction P, which can be advantageous when the repair assembly 1 is loaded onto an insertion instrument, as described in more detail below. The splice end 6*c*2 of the actuation member 6 is preferably located distal of the free end 6*e* of the actuation member 6 (see FIG. 4E), as described in more detail below.

Figure 4D:
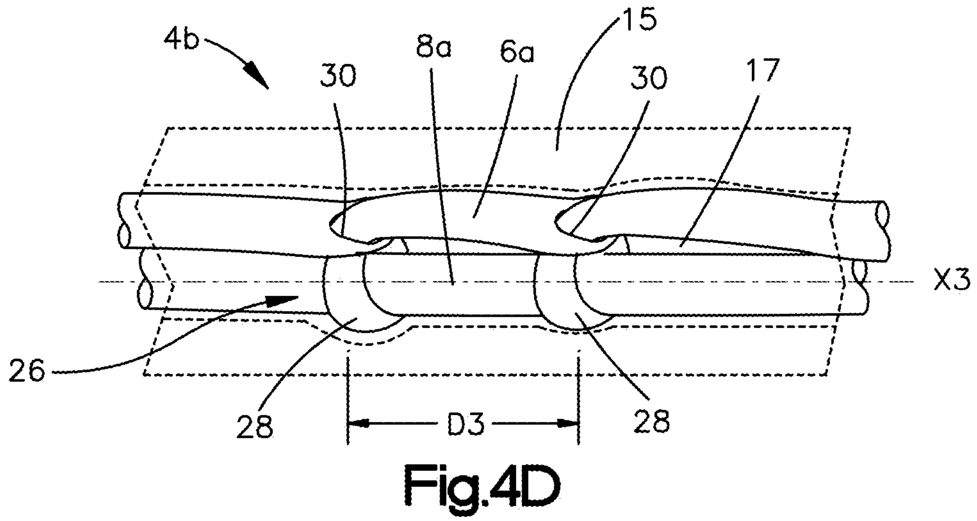
FIG. 4D is an enlarged diagram view of a one-way locking mechanism disposed within the distal portion of the soft anchor illustrated in FIG. 4C.

Referring now to FIGS. 4A-4D, the repair assembly 1 includes a retention or "locking" mechanism 26 that is configured to retain the actuation member 6 in place relative to the anchor body 4 when in the approximated configuration C3, thereby maintaining the approximated position of the second anatomical structure 7 with respect to the first anatomical structure 5. In the present embodiment, the locking mechanism 26 is disposed within the anchor body 4, particularly within the distal portion 4*b* thereof. Additionally, the locking mechanism 26 of the present embodiment is defined by the actuation member 6, particularly by the first actuation portion 6*a*, and is configured to couple with the first snake portion 8*a* when the repair assembly 1 is in the insertion configuration C1, as shown in FIGS. 4C-4D. The locking mechanism 26 is particularly configured so that the snake member 8 can shuttle the free end 6*e* of the actuation member 6 into engagement with the locking mechanism 26 when forming an approximation loop around (or through) the second anatomical structure 7. For this purpose, the locking mechanism 26 is configured to facilitate one-way axial sliding of the snake member 8 and thereafter the joined actuation tail 6*d* relative to the locking mechanism 26 as the repair assembly 1 transitions from the anchored configuration C2 to the approximated configuration C3. Accordingly, the locking mechanism 26 can also be referred to as a "one-way" locking mechanism 26. In the illustrated embodiment, the locking mechanism 26 is particularly configured to allow the snake member 8 and thereafter the joined actuation tail 6*d* to slide relative to the locking mechanism 26 in a first axial snake direction dX3-1 along the central snake member axis X3 toward the first snake tail end 8*e*1, but thereafter to prevent (or at least significantly impede) the joined actuation tail 6*d* from sliding relative to the locking mechanism 26 in a second axial snake direction dX3-2 along the central snake member axis X3 opposite the first axial snake direction dX3-1 (i.e., the second axial snake direction dX3-2 extends toward the second snake tail end 8*e*2). Thus, the "one-way" sliding direction provided by the locking mechanism 26 of the present embodiment is the first axial snake direction dX3-1 shown in FIG. 4C.

In the illustrated embodiment, the locking mechanism 26 includes one or more knot loops 28 that are defined by the first actuation member 6. For example, the locking mechanism 26 can include first and second knot loops 28 that are defined by respective portions of the first actuation portion 6*a* that are bent or otherwise manipulated into loops 28 that double back and penetrate the first actuation portion 6*a* at first and second penetrations 30 of the first actuation portion 6*a*. In the insertion configuration C1, the first snake portion 8*a* extends through the eyelets defined by the knot loops 28. Thereafter, in the approximated configuration C3, the second actuation portion 6*b* (e.g., the joined actuation tail 6*d*) extends through the eyelets of the knot loops 28 (see FIG. 5F), which occurs after the free end 6*e* of the actuation member 6 has been pulled by the snake member 8 through the knot loops 28, as described in more detail below. The knot loop 28 configuration disclosed herein has been observed to provide the one-way sliding of the actuation tail 6*d* discussed above. The locking mechanism 26 of the illustrated embodiment defines a knot loop spacing distance D3 measured between geometric centerpoints of the first and second knot loops 28 along the central body axis X1. The knot loop spacing distance D3 can be in a range of about 1.0 mm to about 12 mm, and more particularly in a range of about 2.0 mm to about 7.0 mm, and more particularly in a range of about 3.5 mm to about 4.5 mm. In other embodiments, the locking mechanism 26 can consist of a single knot loop 28 or can comprise more than two knot loops 28. In yet other embodiments, the locking mechanism 26 can employ other grip structures for providing one-way sliding for the joined actuation tail 6*d*.

Figure 4E:
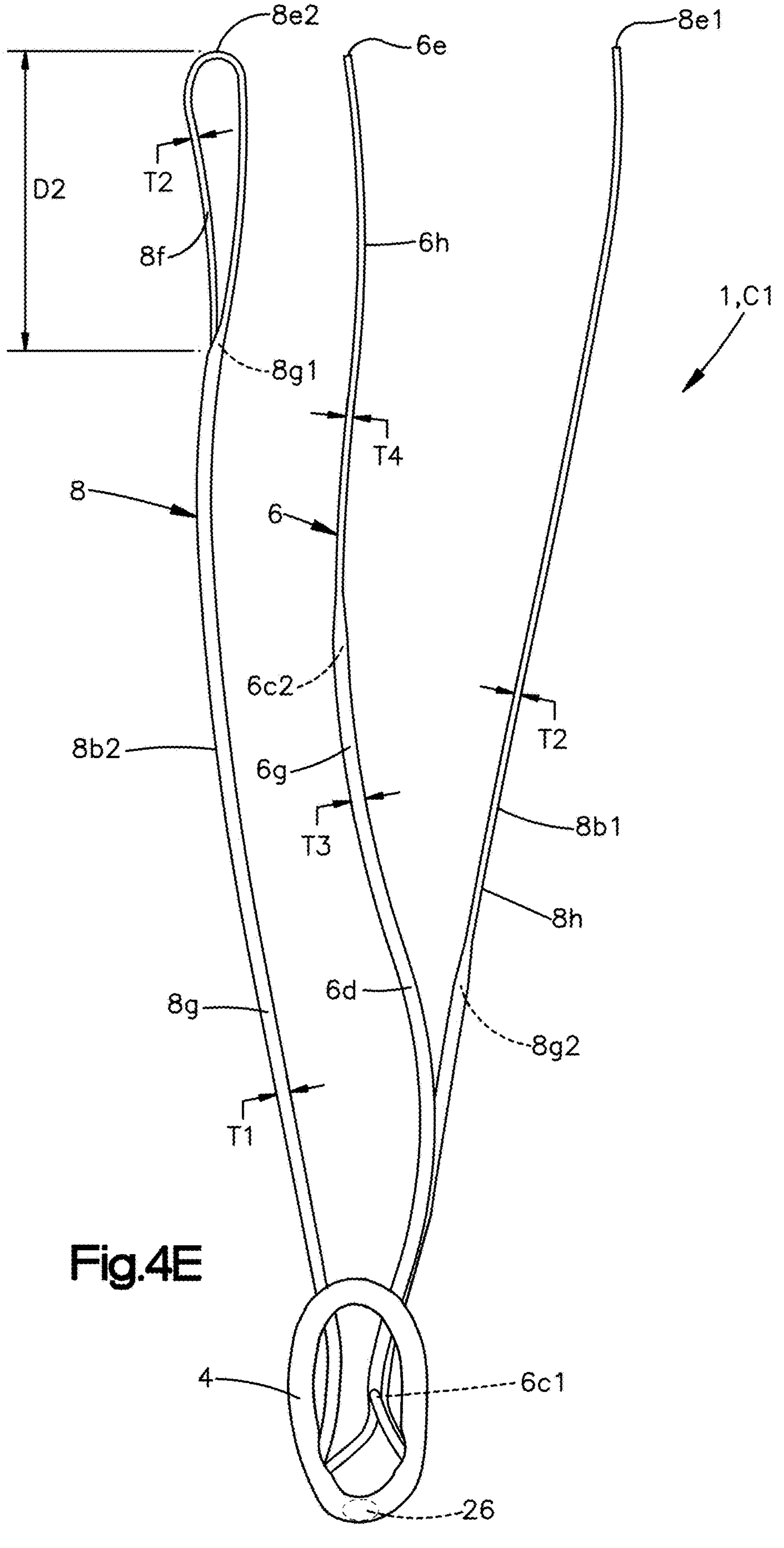
FIG. 4E is another front plan view of the tissue repair assembly illustrated in FIG. 1A.

Referring now to FIG. 4E, the second snake tail end 8*e*2 defines a coupling formation for coupling with a proximal portion 6*h* of the actuation member 6, thereby allowing the snake member 8 to shuttle the actuation member 6 into engagement with the locking mechanism 26 to form an approximation loop. Preferably, the coupling formation of the second snake tail 8*b*2 is defined along a free end region thereof (i.e., a region that extends to the second snake tail end 8*e*2). In the illustrated embodiment, the coupling formation is a loop 8*f*, which can be referred to as a "snake loop" 8*f*, and which is configured to receive a free end region of the actuation member 6 (i.e., a region that extends to the free end 6*e*). In particular, when the free end 6*e* of the joined actuation tail 6*e* is threaded through the snake loop 8*f*, the first snake tail end 8*e*1 is configured to be pulled to draw the free end region of the joined actuation tail 6*d* through the interior passage 22 of the anchor body 4 so that, in the approximated configuration, the joined actuation tail 6*d* defines an approximation loop located exterior of the anchor body 4 for approximating tissue, as described in more detail below. The snake loop 8*f* has a length D2 that is preferably sized to facilitate coupling with the joined actuation tail 6*d*.

The snake loop 8*f* is preferably constructed as an eye splice, by which one portion of the snake member 8 is doubled back at the second snake tail end 8*e*2 and spliced into and along a portion of the second snake tail 8*b*2 and optionally along a portion of the first snake tail 8*b*L. In the illustrated embodiment, the eye splice that provides the snake loop 8*f* extends from a splice insertion point 8*g*1 to a splice end 8*g*2. In this manner, the snake member 8 has a spliced snake portion 8*g* that extends from the splice insertion point 8*g*1 to the splice end 8*g*2. It should be appreciated that the splice insertion point 8*g*1 defines the distal end of the snake loop 8*f*. The spliced snake portion 8*g* has a first or "spliced" snake thickness T1, which is greater than a second or "non-spliced" snake thickness T2 of the remainder of the snake member 8, which remainder includes the portion of the second snake tail 8*b*2 that defines the snake loop 8*f*, and a narrow portion 8*h* of the snake member 8 extending from the splice end 8*g*2 to the first snake tail end 8*e*1). The spliced snake thickness T1 can be about twice (2×) that of the non-spliced snake thickness T2, which results because the spliced snake region 8*g* contains two (2) snake jackets 25 therein, while the narrow snake portion 8*h* contains one (1) snake jacket 25 therein.

The proximal portion 6*h* of the actuation member 6 (which portion can also be referred to as the "proximal actuation portion" 6*h*) extends from the splice end 6*c*2 to the free end 6*e* of the actuation member 6 and is configured to thread through the snake loop 8*f* for coupling therewith, thereby allowing the snake member 8 to shuttle the actuation member 6 through the knot loops 28 of the locking mechanism 26. In the illustrated embodiment, the joined actuation tail 6*d* includes both the spliced actuation portion 6*g* and the proximal actuation portion 6*h*. Stated differently, in the illustrated embodiment, the spliced actuation portion 6*g* and the proximal actuation portion 6*h* are constituent parts of the joined actuation tail 6*d*. The spliced actuation portion 6*g* has a first or "spliced" actuation thickness T3, which is greater than a second or "non-spliced" actuation thickness T4 of the proximal actuation portion 6*h*. The spliced actuation thickness T3 can be about twice (2×) that of the non-spliced actuation thickness T4, which results because the spliced actuation portion 6*g* has two (2) actuation jackets 19 (the interior and exterior jackets 19), while the proximal actuation portion 6*h* has one (1) actuation jacket 19.

It should be appreciated that the splice ends 6*c*2, 8*g*2 of the actuation member 6 and the snake member 8 can be respectively located to facilitate smooth shuttling of the actuation member 6 through the knot loops 28 of the locking mechanism 26. For example, the location of the splice end 8*g*2 of the snake member 8 can be tailored to set preferential initial conditions in the knot loops 28. In the illustrated embodiment, the splice end 8*g*2 of the snake member 8 is located on the opposite side of the locking mechanism 26 from the splice insertion point 8*g*1, such that the spliced snake portion 8*g* extends through the knot loops 28 when in the insertion configuration C1. Thus, when the repair assembly 1 is in the insertion configuration C1, the sizes of the knot loops 28 can be dressed (i.e., constricted) to the spliced snake thickness T1, which is greater than the non-spliced snake thickness T2. Stated differently, when in the insertion configuration C1, the inner diameters of the knot loops 28 can be substantially equivalent to the spliced snake thickness T1. When the spliced snake thickness T1 is about twice (2×) that of the non-spliced snake thickness T2 (i.e., when T1≈2×T2, the spliced snake region 8*g* will result in initial knot loops 28 having inner diameters about twice (2×) what their value would be had the knot loops 28 been assembled around the narrow snake portion 8*h*. The foregoing size differences between T1 and T2 (i.e., T1>T2) reduces mechanical impedance as the snake loop 8*f* shuttles the actuation member 6 through the knot loops 28.

Additionally, the splice end 6*c*2 of the actuation member 6 can be located to maximize the performance of the tissue repair assembly 1. For example, the splice end 6*c*2 of the actuation member 6 is preferably located remote from the free end 6*e* so as to be located along the actuation post during an after tissue approximation. Additionally, the splice end 6*c*2 of the actuation member 6 is preferably sufficiently distally located from the free end 6*e* so that the proximal actuation portion 6*h* can thread through the snake loop 8*f* and double back on itself as the snake loop 8*f* pulls the proximal actuation portion 6*h* toward the knot loops 28 (see FIG. 5D). The size difference between the spliced actuation thickness T3 and the non-spliced actuation thickness T4 (i.e., T3>T4) further reduces mechanical impedance as the snake loop 8*f* shuttles the proximal actuation portion 6*g* through the knot loops 28. The size difference of T3 being greater than T4 provides a significant advantage to the repair assembly 1 because, when the proximal actuation portion 6*h* is threaded through the snake loop 8*f* and doubled back on itself, the coupled construct (i.e., the doubled-back proximal actuation portion 6*h* and the snake loop 8*f*) has a local maximum thickness at the second snake end 8*e*2 that can be the sum of about twice (2×) the non-spliced snake thickness T2 and about twice (2×) the non-spliced actuation thickness T4 (i.e., the local maximum thickness≈(2×T2)+(2×T4)). When thicknesses T2 and T4 are less than T1 and T3, respectively, the coupled construct experiences less impedance as it shuttles through the knot loops 28, thereby requiring a comparatively lower shuttling force. For example, when T2 is about ½ T1 and when T4 is about ½ T3, the coupled construct can have a local maximum thickness that is about ¼ (about 25%) of what it would be if there were no thickness differences between T1 and T2 and between T3 and T4, respectively. Thus, the spliced snake portion 8*g* and the spliced actuation portion 6*g* can provide significant reductions to impedance experienced by the actuation member 6 as it shuttles through the knot loops 28, thereby also requiring a lower shuttle force. In this manner, the presence of the spliced snake portion 8*g* and the spliced actuation portion 6*g* facilitates a smooth transition as the snake member 8 pulls the actuation member 6 into the interior passage 22 of the anchor body 4 and through the knot loops 28 during shuttling.

Another benefit derived from the presence of the spliced actuation portion 6*g*, and the location of the spliced end 6*c*2, is that the bury splice thereof expands the local thickness to T3, which also increases the pick count (i.e., the quantity of fibers along a given length of suture) of the spliced actuation portion 6*g*. The expanded thickness T3 and the increased pick count of the spliced actuation portion 6*g* enhances the locking force provided by the locking mechanism 26 when the spliced actuation portion 6*g* passes through the knot loops 28. It should be appreciated that a tradeoff can be made between increasing the initial size of the knot loops 28 (e.g., to reduce the required shuttle force) versus increasing the extent to which the knot loops 28 must constrict to dress to the joined actuation tail 6*d* with sufficient force to perform the one-way locking during and after tissue approximation. It should also be appreciated that the thickness(es) of the snake member 8 (e.g., T1 and T2) and the actuation member 6 (e.g., T3 and T4) can be altered locally to provide desired conditions for the intended application, which conditions can include initial conditions (such as in the insertion configuration C1), anchoring conditions (such as during and after transition to the anchored configuration C2), shuttling conditions, and approximation conditions (such as during and after transition to the approximated configuration C3).

Referring now to FIGS. 5A-5H, the manner in which the repair assembly 1 is adapted for approximating tissue will now be described according to an exemplary technique.

Figures 5A, 5B, 5C, 5D:
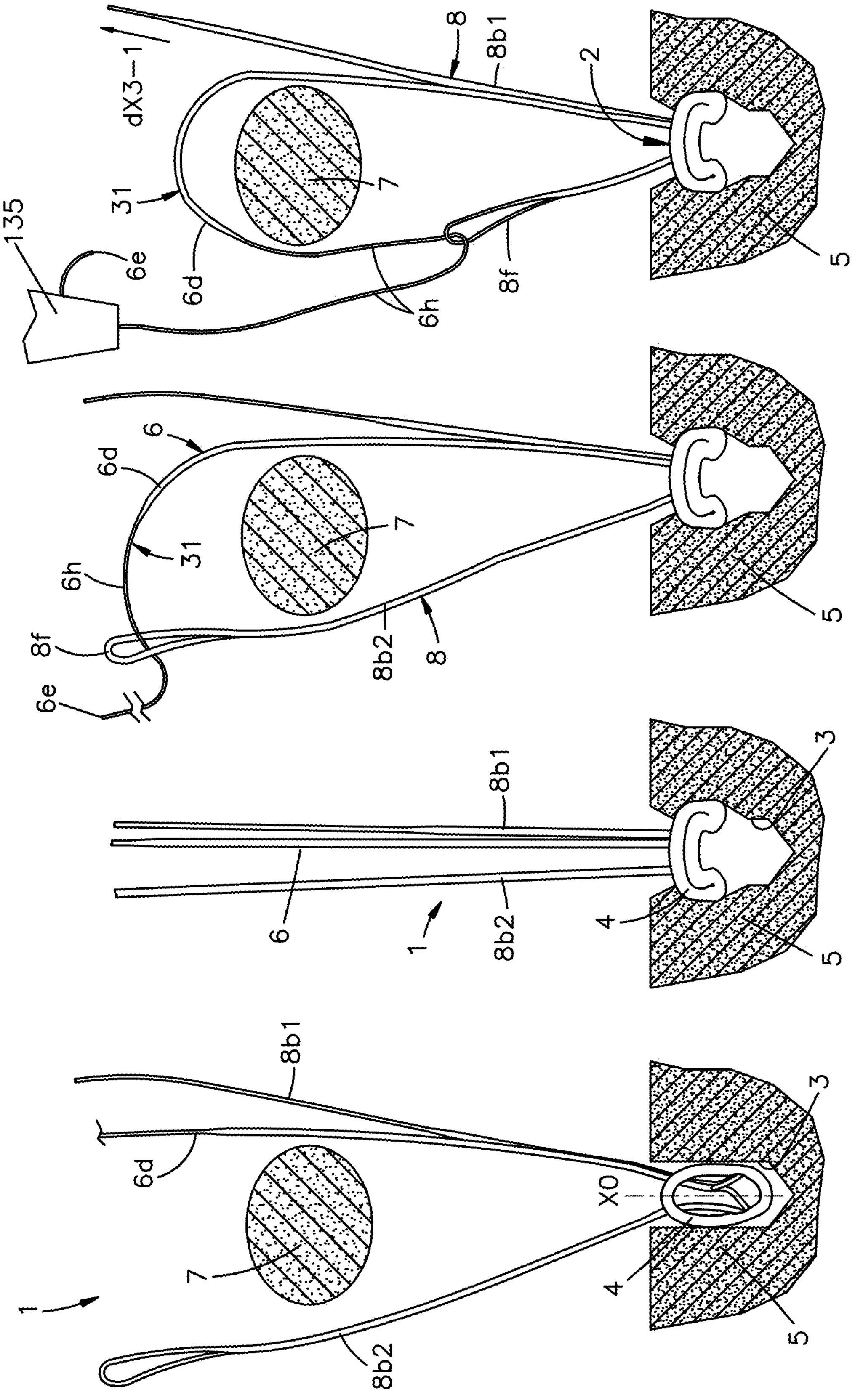
FIGS. 5A-5E and 5G-5H are front plan views of the tissue repair assembly illustrated in FIG. 1A, showing the tissue repair assembly in various stages of a process for approximating tissue, according to an embodiment of the present disclosure.

As shown in FIG. 5A, the anchor body 4 is inserted, in the insertion configuration C1, within a target location 3 of a first anatomical structure 5 along the insertion axis X0. In this example, the first anatomical structure 5 is bone and the target location 3 is a pre-drilled hole 3 in the bone 5. The joined actuation tail 6*d* and the first and second snake tails 8*b*1, 8*b*2 extend generally proximally from the anchor body 4. As shown in FIG. 5B, the repair assembly 1 is actuated into the anchored configuration C2 by applying tensile forces simultaneously to the joined actuation tail 6*d* and to the first and second snake tails 8*b*1, 8*b*2, causing the anchor body 4 to bunch up and affix to bone along the sides of the hole 3.

As shown in FIG. 5C, the second snake tail 8*b*2 and the joined actuation tail 6*d* are positioned on opposite sides of the second anatomical structure 7. From this position, the free end 6*e* of the joined actuation tail 6*d* is positioned proximally around the second anatomical structure 7 and the proximal actuation portion 6*h* is threaded through and coupled with the snake loop 8*f*, so that the second anatomical structure 7 is captured by the joined actuation tail 6*d* and the second snake tail 8*b*2. At this stage, the actuation member 6 and the snake member 8 join together to form a closed shuttle loop 31 around the second anatomical structure 7. In particular, the shuttle loop 31 includes the first snake portion 8*a* (which extends through the knot loops 28 of the locking mechanism 26, as shown in FIG. 4D), the second snake tail 8*b*2, and the joined actuation tail 6*d* coupled thereto (via the snake loop 8*f*). The shuttle loop 31 facilitates the formation of an approximation loop 32 that will be defined by the actuation member 6 extending around the second anatomical structure 7 and through the locking mechanism 26, as described in more detail below. Thus, the shuttle loop 31 can be characterized as a precursor to the approximation loop 32.

Figure 5E:
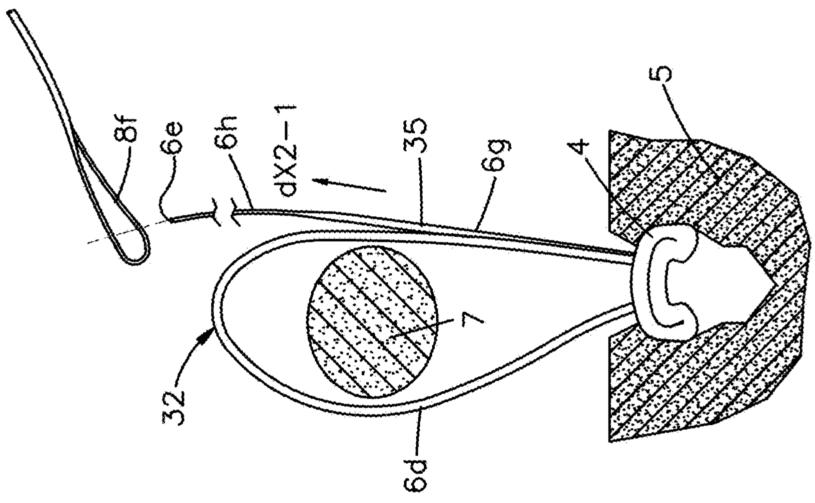
Figure 5F:
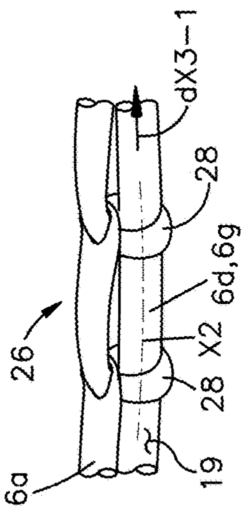
FIG. 5F is an enlarged diagram view of the one-way locking mechanism at the stage illustrated in FIG. 5E.

As shown in FIG. 5D, tension is applied to the first snake tail 8*b*1 in the first axial snake direction dX3-1. This causes the snake loop 8*f* to pull the joined actuation tail 6*d* in the first axial snake direction dX3-1, thereby shuttling the joined actuation tail 6*d* toward the locking mechanism 26 in the anchor 2. During shuttling, the free end 6*e* of the joined actuation tail 6*d* can optionally be secured via a tool 135, such as a grasper or the like, to prevent the joined actuation tail 6*d* from decoupling from the snake loop 8*f*. Securing the free end 6*e* of the joined actuation tail 6*d* also allows the proximal actuation portion 6*h* to double back over itself in the snake loop 8*f* during shuttling, as described above. The shuttling continues so that the proximal actuation portion 6*h* of the joined actuation tail 6*d* is pulled by the snake loop 8*f* into, through, and out the opposite side of the locking mechanism 26 along the first axial snake direction dX3-1, as shown in FIGS. 5E-5F. In particular, this shuttling results in the spliced actuation portion 6*g* of the joined actuation tail 6*d* being threaded through the knot loops 28 of the locking mechanism 26, as shown in FIG. 5F. At this stage, the snake member 8 has exited the anchor body 4 and no longer extends through the knot loops 28 of the locking mechanism 26 and thus the snake loop 8*f* can be decoupled from the joined actuation tail 6*d*.

Figure 5G:
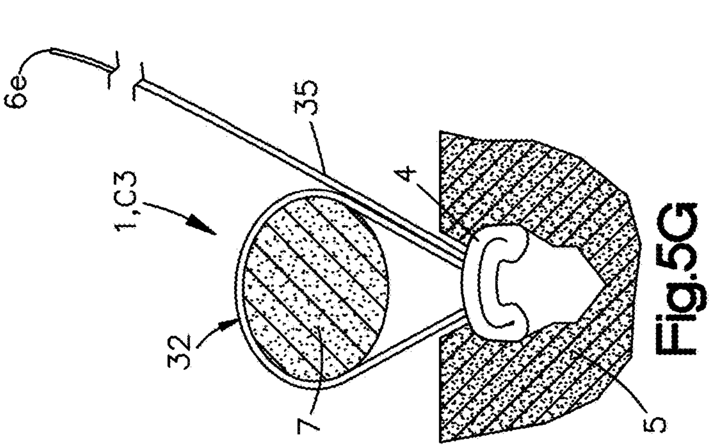

As shown in FIG. 5E, the joined actuation tail 6*d* at this stage defines an approximation loop 32, which extends from the locking mechanism 26 in the anchor body 4, around the second anatomical structure 7, and back into the locking mechanism 26. In particular, the spliced actuation portion 6*g* of the joined actuation tail 6*d* defines the approximation loop 32. Additionally at this stage, the joined actuation tail 6*d* also has a free portion 35 that extends from the locking mechanism 26 to the free end 6*e* of the joined actuation tail 6*d*. The free portion 35 can also be referred to herein as the "actuation post" 35 of the actuation member 6, and is employed to pull the actuation member 6 in a manner reducing a circumference of the actuation loop 32 to approximate the second anatomical structure with respect to the first anatomical structure, as shown in FIG. 5G. In particular, to reduce the circumference of the approximation loop 32 to approximate the second anatomical structure 7, the actuation post 35 is pulled away from the anchor body 4 in a first axial actuation direction dX2-1 toward the free end 6*e* of the post 35. During approximation, the spliced actuation portion 6*g* slides through the knot loops 28 of the locking mechanism 26, which engage the braided exterior jacket 19 of the spliced actuation portion 6*g* in a manner that provides one-way sliding therethrough (i.e., along the first axial actuation direction dX2-1) but prevents (or at least substantially resists) sliding in the opposite direction, as described above.

Figure 5H:
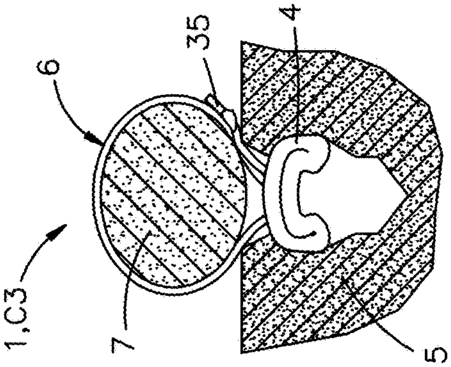

As shown in FIG. 5H, when the second anatomical structure 7 is satisfactorily approximated with respect to the first anatomical structure 5, the free end 6*e* of the post 35 is preferably trimmed to remove the excess suture material at the treatment site. It should be appreciated that the locking mechanism 26 substantially locks the approximation loop 32 in the fully approximated configuration, thereby obviating the need to further tie-off the free portion of the joined actuation tail 6*d*. Optionally, the post 35 can be tied-off, as shown, to provide a secondary locking structure to the approximation loop 32. It should be appreciated that numerous additional and/or alternative steps can be performed to facilitate the foregoing exemplary technique for approximating tissue.

Figure 6A:
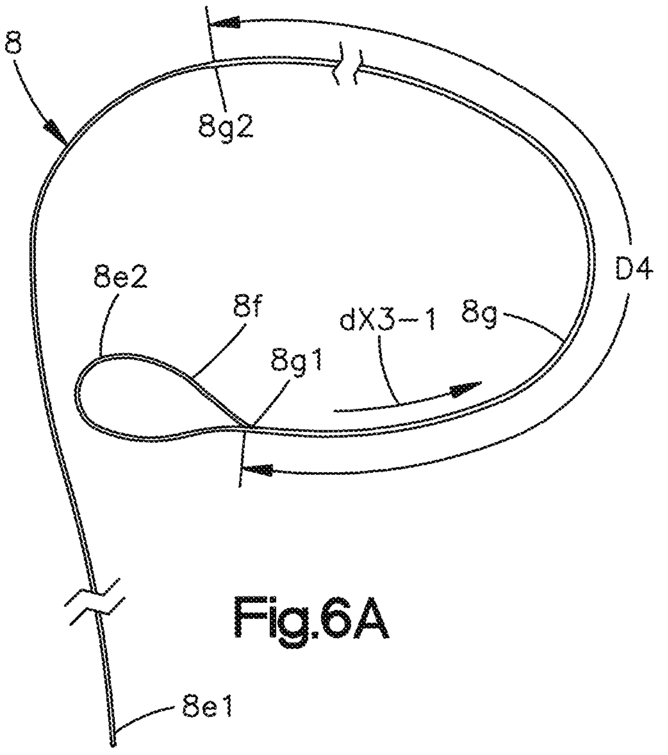
FIGS. 6A-6M are respective plan views of the tissue repair assembly illustrated in FIG. 1A, shown at various stages of constructing the tissue repair assembly and the soft anchor thereof, according to an embodiment of the present disclosure.

With reference to FIGS. 6A-6N, an exemplary method will be described for constructing the repair assembly 1, which can also be referred to as a method for preparing the repair assembly 1 for use. Accordingly, the repair assembly 1 discussed in FIGS. 6A-6P can be characterized as being in various stages of a preparatory configuration.

As shown in FIG. 6A, the snake loop 8*f* is formed at the second snake tail end 8*e*2, preferably by forming an eye splice, by which one portion of an end region of the snake member 8 is doubled back and spliced into and along another portion of the end region, thereby defining a spliced snake portion 8*g* of the snake member 8, as described above with reference to FIG. 4E. The spliced snake portion 8*g*, which provides the snake loop 8*f*, can extend from a splice insertion point 8*g*1, which defines the distal end of the snake loop 8*f*, to a splice end 8*g*2 that is spaced away from the splice insertion point 8*g*1 in the first axial snake direction dX3-1. The spliced snake portion 8*g* can be formed, for example, by bury splicing the end region of the snake member 8 into itself from the splice insertion point 8*g*1 to the splice end 8*g*2. The spliced snake portion 8*g* has a splice length D4, measured from the splice insertion point 8*g*1 to the splice end 8*g*2. Preferably, the splice length D4 is greater than half (½) the total length of the snake member 8, which facilitates subsequently positioning the spliced snake portion 8*g*2 through the knot loops 28 of the locking mechanism 26 in the insertion configuration C1, as discussed above with reference to FIG. 4E, and which step is discussed in more detail below.

Figure 6B:
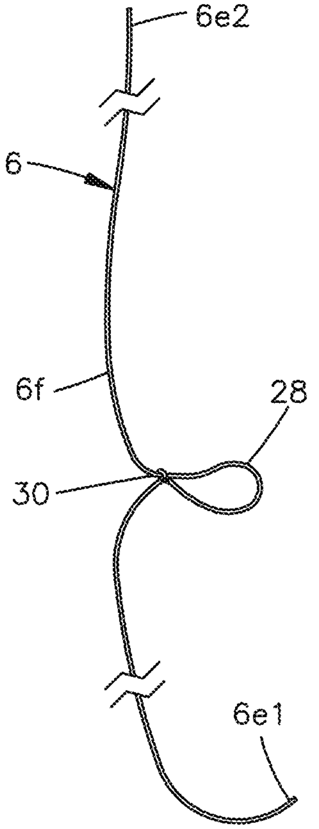
Figure 6C:
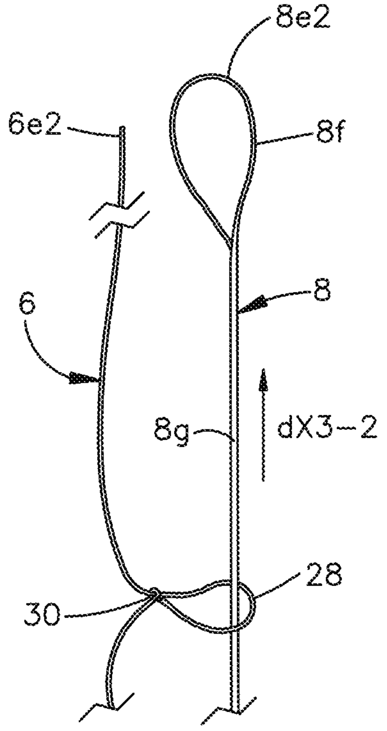
Figure 6D:
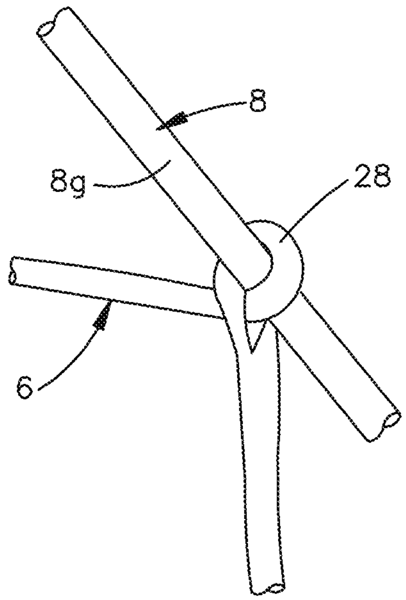
Figure 6E:
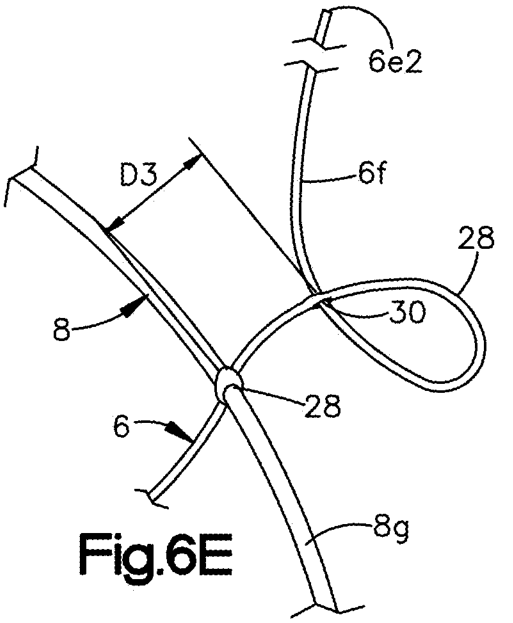
Figure 6F:
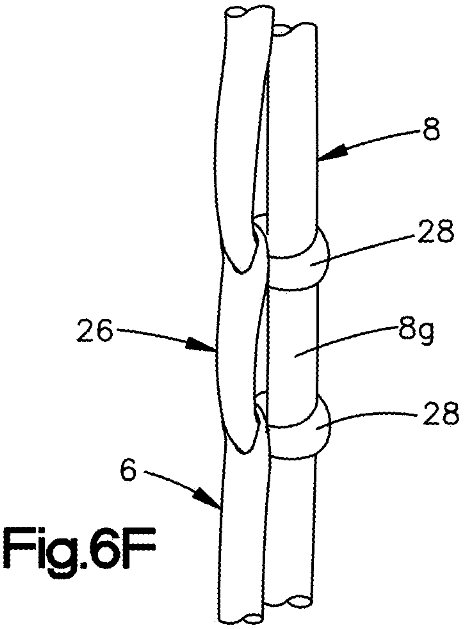

As shown in FIG. 6B, formation of the locking mechanism 26 of the actuation member 6 is commenced by piercing a second end 6*e*2 of the actuation member 6 (opposite a first end 6*e*1 thereof) through a central portion 6*f* of the actuation member 6 at the first penetration 30. This forms the first knot loop 28, which is collapsible for subsequently dressing to the snake member 8. Preferably, the second end 6*e*2 of the actuation member 6 pierces substantially perpendicularly through the central actuation axis X2 of the actuation member 6 at the first penetration 30. As shown in FIG. 6C, the second snake tail end 8*e*2 and the snake loop 8*f* are threaded through the first knot loop 28 in the second axial snake direction dX3-2. Subsequently, as shown in FIG. 6D, the first knot loop 28 is collapsed around dressed to the portion of the snake member 8 extending therethrough, which in the illustrated embodiment is the spliced snake portion 8*g*. As shown in FIG. 6E, formation of the locking mechanism 26 continues by piercing the second end 6*e*2 of the actuation member 6 through the central portion 6*f* of the actuation member 6 at the second penetration 30 to form the second knot loop 28, which is collapsible. As with the first penetration, the second end 6*e*2 of the actuation member 6 pierces substantially perpendicularly through the central actuation axis X2 of the actuation member 6 at the second penetration 30. The second penetration 30 is spaced from the first penetration 30 at the knot loop spacing distance D3 discussed above. Subsequently, the second snake tail end 8*e*2 and the snake loop 8*f* are threaded through the second knot loop 28 in the second axial snake direction dX3-2, and, as shown in FIG. 6F, the second knot loop 28 is collapsed around and dressed to the portion of the snake member 8 extending therethrough (i.e., the spliced snake portion 8*g*). At this stage, the locking mechanism 26 has been formed having the knot loops 28 that constrict against and thereby grip the snake member 8. As described above with reference to FIG. 4E, the portion of the snake member 8 that is gripped by the knot loops 28 at this stage is the spliced snake portion 8*g*.

Figure 6G:
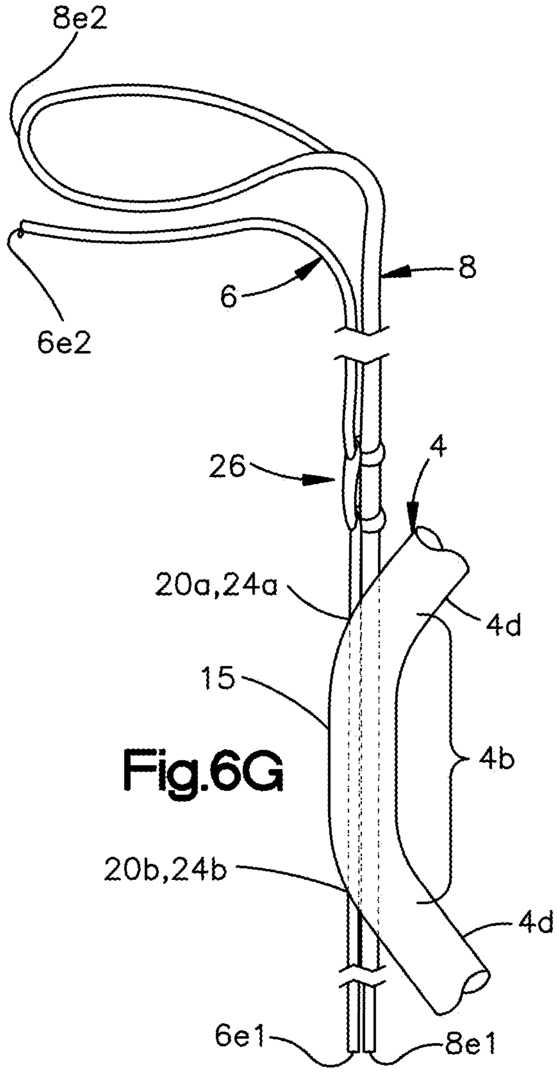
Figure 6H:
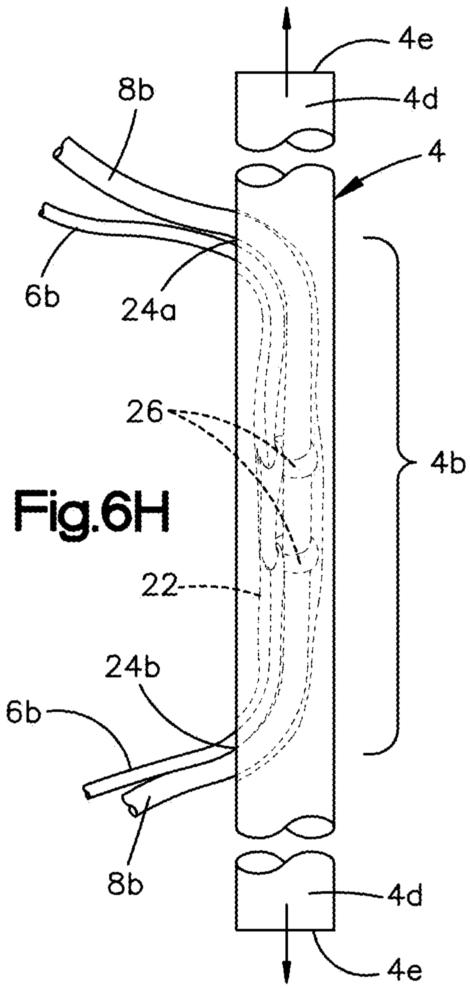

As shown in FIG. 6G, the actuation member 6 and the snake member 8 are coupled with the anchor body 4, particularly by being spliced with the anchor body 4. In particular, the first end 6*e*1 of the actuation member 6 and the first snake tail end 8*e*1 pierce the jacket 15 of the anchor body 4 at the second penetration 24*b* (positioned at the second location 20*b*), from which the first end 6*e*1 and the first snake tail end 8*e*1 enter the interior passage 22 of the anchor body 4. From there, the first end 6*e*1 and the first snake tail end 8*e*1 are drawn into and along the core space 17 of the anchor body 4, and pierce the anchor body 4 to exit therefrom at the first penetration 24*a* (positioned at the first location 20*a*). Preferably, the first end 6*e*1 of the actuation member 6 and the first snake tail end 8*e*1 are drawn simultaneously together into, through, and out of the interior passage 22 of the anchor body 4, which can ensure that the actuation member 6 and the snake member 8 enter the anchor body 4 together at the same location (i.e., the second penetration 24*b*) and exit the anchor body 4 together at the same location (i.e., the first penetration 24*a*). It should be appreciated that, to pierce the jacket 15 of the anchor body 4 at the first and second penetrations 24*a,b*, the first end 6*e*1 of the actuation member 6 and the first snake tail end 8*e*1 can both be coupled to a piercing instrument, such as a needle, which pierces the jacket 15 at the first and second penetrations 24*a,b* and pulls the actuation member 6 and the snake member 8 therethrough. The first end 6*e*1 of the actuation member 6 and the first snake tail end 8*e*1 are further pulled until the locking mechanism 26 is positioned inside the interior passage 22 of the anchor body 4 between the first and second penetrations 24*a,b*, as shown in FIG. 6H. Preferably, the locking mechanism 26 is laterally centered between the first and second penetrations 24*a,b*. It should be appreciated that the portion of the anchor body 4 extending between the first and second penetrations 24*a,b* will become the distal portion 4*b* of the anchor body 4 when the anchor body 4 is further prepared and arranged into the insertion configuration C1. In the preparatory configurations, such as those shown in FIGS. 6G-6H, the portions of the anchor body 4 extending oppositely away from the distal portion 4*b* can be referred to as anchor body tails 4*d*. With the locking mechanism 26 positioned as desired within the interior passage 22 of the anchor body 4, tension is applied to the anchor tails 4*b*, such as at ends 4*e* thereof, to collapse the jacket 15 around the locking mechanism 26 in snug fashion, as shown in FIG. 6H. At this stage, the portions of the actuation member 6 and the snake member 8 that are located exterior of the anchor body 4 are the respective actuation tails 6*b* and snake tails 8*b* described above with reference to FIGS. 4A-4C.

Figure 6I:
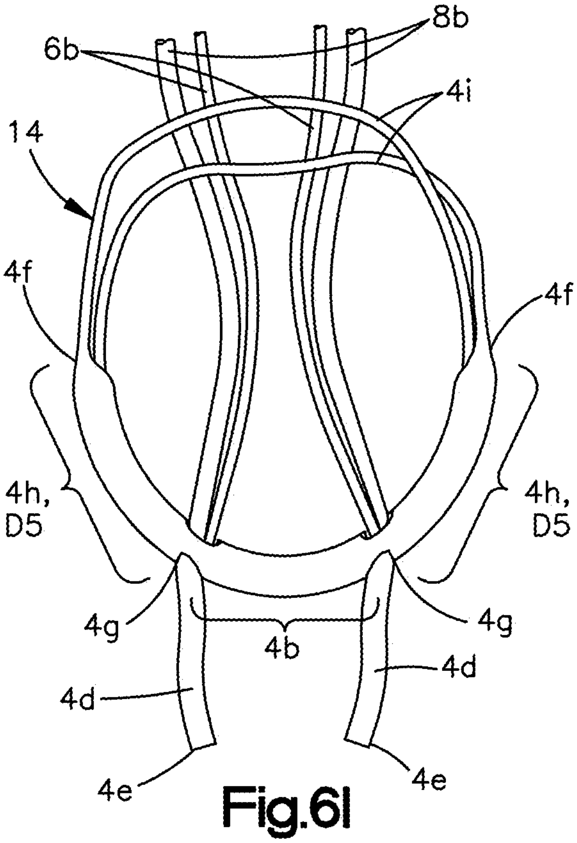

As shown in FIG. 6I, a process for arranging the anchor body 4 into the anchor loop 14 includes coupling the anchor body tails 4*d* together. For example, at least one of the anchor body tails 4*d* can be spliced into the other of the anchor body tails 4*d*. In the illustrated example, each of the anchor body tails 4*d* is spliced with the opposite anchor body tail 4*d*, beginning at a splice insertion point 4*f*, extending therefrom along a splice region 4*h* of the respective opposite anchor body tail 4*d*, and exiting therefrom at a splice exit point 4*g*. The splice exit point 4*g* of each anchor body tail 4*d* can be adjacent the locking mechanism 26 embedded within the distal portion 4*b* of the anchor body 4. The splice regions 4*h* of the anchor body tails 4*d* each have a splice length D5, measured between the splice insertion point 4*f* and the splice exit point 4*g*, which can be in a range of about 3.0 mm to about 30 mm, and mor particularly in a range of about 8.0 mm to about 16.0 mm, and more particularly in a range of about 11.5 mm to about 13.5 mm. At the presently depicted stage of construction, the actuation tails 6*b* and snake tails 8*b* preferably bypass unspliced portions 4*i* of the anchor body tails 4*d* opposite the distal portion 4*b* of the anchor body 4 at the same side of the unspliced portions 4*i*. Stated differently, the actuation tails 6*b* and snake tails 8*b* preferably do not extend through an opening or gap between the unspliced portions 4*i* of the anchor body tails 4*d* at the depicted stage of construction.

Figure 6J:
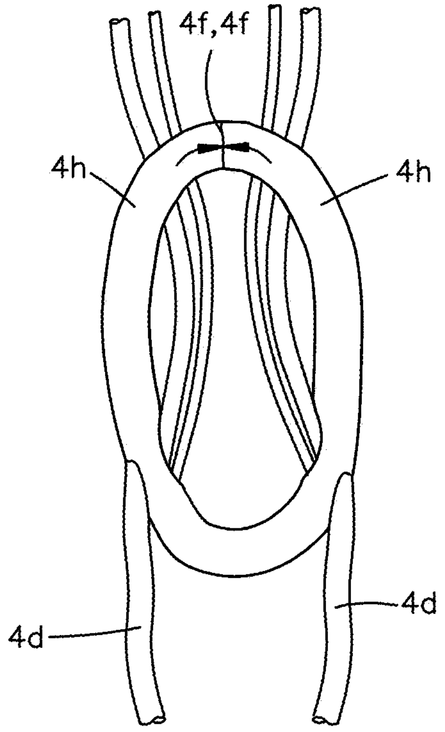
Figure 6K:
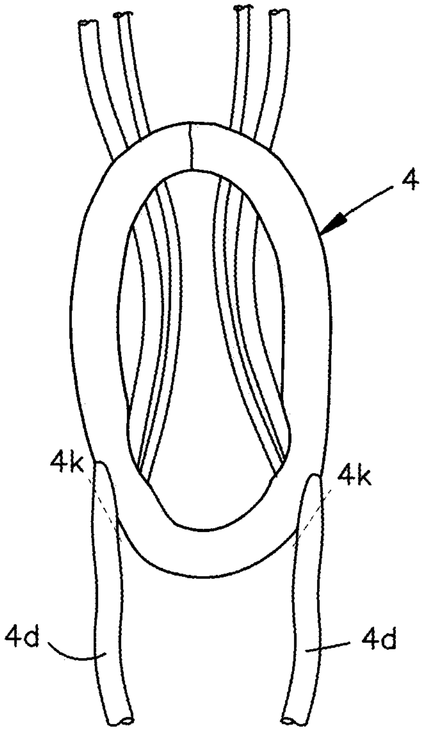
Figure 6L:
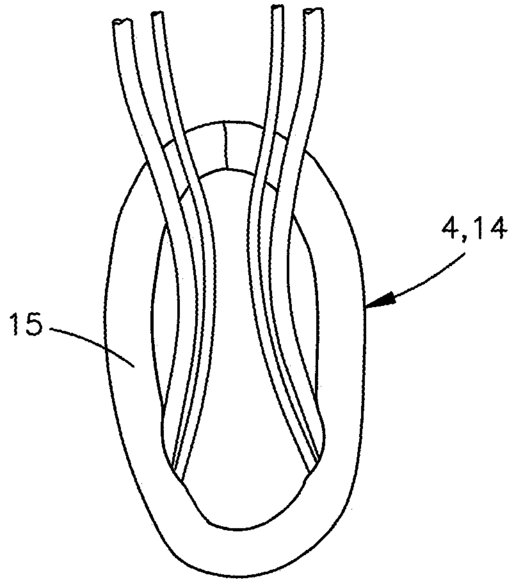

As shown in FIG. 6J, the ends 4*e* of the anchor body tails 4*d* are tensioned to pull the anchor body tails 4*d* through the spliced regions 4*h* and to draw the splice insertion points 4*f* toward each other, preferably until the splice insertion points 4*f* are substantially drawn together (i.e., substantially co-localized). Subsequently, as shown in FIG. 6K, the anchor body 4 can be tensioned to stretch the outer braid of the jacket 15 of the anchor body 4 until the outer jacket 15 constricts against the inner anchor body tails 4*d*. The portions of the anchor body tails 4*d* extending outwardly from the anchor loop 14 can be trimmed (e.g., cut) at trim locations 4*k*. Subsequently, the circumference of the anchor loop 14 can be marginally increased such that the trimmed ends of the anchor body tails 4*d* are pulled inside the jacket 15 of the anchor body 4, resulting in the construct shown in FIG. 6L.

Figure 6M:
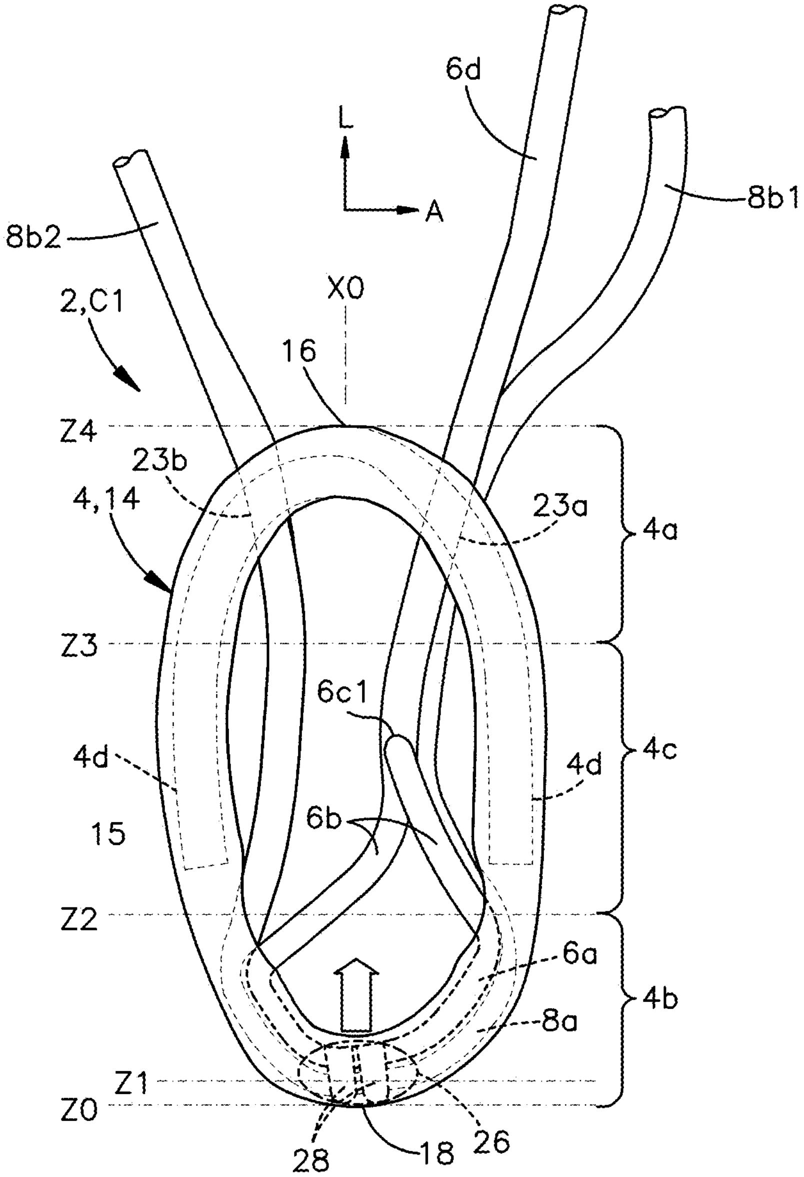

As shown in FIG. 6M, the actuation tails 6*b* are coupled together, such as by bury splicing one of the actuation tails 6*b* into the other actuation tail 6*b* from the splice insertion point 6*c*1 to the splice end 6*c*2, as described above with reference to FIGS. 4A-4B and FIG. 4E. As described above, this provides a joined actuation tail 6*d* extending from the splice insertion point 6*c*1 to the free end 6*e* of the actuation member 6, as shown in FIG. 4E. A step for removing unwanted laxity in the joined actuation tail 6*d* can include pushing the laxity in the jacket 19 of the exterior actuation tail 6*b*2 proximally, starting at the splice insertion point 6*c*1 toward the free end 6*e*. This effectively tensions the braid of the exterior jacket 19 along its length until the exterior jacket 19 constricts against the jacket 19 of the inner actuation tail 6*b*1, thereby synchronizing the braid structures of the exterior and interior jackets 19. As shown in FIG. 6M, and as described above with reference to FIGS. 4A-4B the joined actuation tail 6*d* and one or both of the snake tail 8*b*1, 8*b*2 can be pierced through the proximal portion 4*a* of anchor body 4. In the illustrated embodiment, the joined actuation tail 6*d* and the second snake tail 8*b*2 pierce through the proximal portion 4*a* of the anchor body 4 at respective proximal penetrations 23*a,b*, which are located on opposite lateral sides of the insertion axis X0 axis. It should be appreciated that the locations of the proximal penetrations 23*a,b* can be respectively selected to substantially align with the distal penetrations 24*a,b* along the longitudinal direction L. After piercing through the proximal portion 4*a* of the anchor body 4, the joined actuation tail 6*d* and second snake tail 8*b*2 are preferably tensioned to remove any slack in their respective jackets 19, 25 within the anchor eyelet 12. As this stage, the repair assembly 1 is constructed and ready for loading onto an assertion instrument.

It should be appreciated that the foregoing exemplary techniques for constructing the repair assembly 1 of the illustrated embodiment provide the anchor 2 with a particularly advantageous design for anchoring within a pre-drilled hole in bone. With reference again to FIG. 6M, some of these advantages will now be described. One such advantage is that the elongated, elliptical profile of the anchor loop 14 provides the distal portion 4*b* with a tapered profile (particularly a taper that progressively narrows distally) when in the insertion configuration C1, which facilitates ease of insertion into the hole. This tapered profile can be accentuated when the anchor 2 is loaded on an insertion instrument, such as an inserter fork, as described in more detail below. Another advantage is that, when in the anchored configuration C2 (see FIG. 2B), the anchor body 4 has been observed to present a broad proximal face 16*a* at or adjacent the proximal end 16, which combined with the increased second maximum width W2, enhanced affixation in bone and reduces the chances of pullout. The proximal portion 4*a* of the anchor body 4 also provides a proximal barrier-like formation that mechanically interferes with and thus resists migration of the locking mechanism 26 away from the anchor body 4 (such as during anchoring and/or tissue approximation) and thus also resists tenting affects and unwanted laxity in the approximation loop 32 that can result from such migration.

Yet another advantage is that, as the soft anchor 2 transitions from the insertion configuration C1 to the anchored configuration C2, the soft anchor 2 undergoes an actuation sequence (i.e., bunching up sequence) that provides enhanced tactile feedback to the user (e.g., a surgeon, physician, technician, or other medical professional). Because the maximum length of the anchor body 4 along the longitudinal direction L decreases from L1 to L2 during actuation to the anchored configuration, the longitudinal aspects of this actuation sequence can also be referred to herein as a "longitudinal anchor collapse sequence." Aspects of the longitudinal anchor collapse sequence will be described with reference to longitudinal reference locations Z0-Z4 of the soft anchor 2 in the insertion configuration C1, which are shown in FIG. 6N. Of these longitudinal reference locations: location Z0 is aligned with the distal end 18 of the anchor body 4; location Z1 is aligned with the locking mechanism 26, particularly where the first snake portion 8*a* extends through the knot loops 28; location Z2 is aligned with the first and second locations 20*a,b* described above; location Z3 is aligned with the boundary between the intermediate and proximal portions 4*c,b* of the anchor body 4; and location Z4 is aligned with the proximal end 16 of the anchor body 4.

In part because the trimmed anchor body tails 4*d* reside in the axial core space 17 of the anchor body 4 proximate the first and second locations 20*a,b*, the longitudinal regions of the soft anchor between locations Z2 and Z4 generally possess more material in their lateral-transverse cross-sections (i.e., cross-sections in respective planes extending along the lateral and transverse directions A, T) than the material in lateral-transverse cross-sections in the regions of the soft anchor between locations Z0 and Z2. Stated differently, the soft anchor 2 generally has more lateral-transverse cross-sectional bulk in the proximal and intermediate longitudinal regions (between Z2 and Z4) than in the distal region (between Z0 and Z2). Because the locking mechanism 26 is located at the distal extremities of the actuation member 6 and the snake member 8, which are positioned within the distal portion 4*b* of the anchor body 4, and because the locking mechanism 26 is substantially laterally centered within the distal portion 4*b* of the anchor body 4, when a user applies the actuating tensile forces to the free ends 6*e*, 8*e*1, 8*e*2 of the actuation member 6 and the snake tails 8*b*1, 8*b*2, respectively, those tensile forces are transmitted primarily to the locking mechanism 26 (i.e., the knot loops 28 and the first snake portion 8*a* extending therethrough) at location Z1. Thus, an initial phase of the longitudinal anchor collapse sequence involves the locking mechanism 26 being pulled proximally, and thereby pulling the distal portion 4*b* of the anchor body 4 (including the jacket 15 surrounding the locking mechanism 26) proximally toward location Z2. Accordingly, the locking mechanism 26 can be characterized as the leading structure of longitudinal anchor collapse. Thus, as the locking mechanism 26 moves proximally during the longitudinal anchor collapse sequence, the locking mechanism 26 carries progressively more surrounding bulk (i.e., material) of the soft anchor 2 along with it.

As the locking mechanism 26 advances proximally from location Z2 toward location Z3, the intermediate portion 4*c* of the anchor body 4 effectively folds inwardly upon itself and generally towards the locking mechanism 26. Subsequently, as the locking mechanism 26 withdraws proximally from location Z3 toward location Z4, the locking mechanism 26 pulls the distal portion 4*b* of the anchor body 4 proximally into mechanical interference with the proximal portion 4*a* of the anchor body 4. In this manner, the proximal portion 4*a* of the anchor body 4 effectively acts as a barrier preventing the distal portion 4*b* of the anchor body 4 from advancing proximally beyond the proximal portion 4*a*. Such mechanical interference with the proximal portion 4*a* of the anchor body 4 also effectively prevents the locking mechanism 26 from migrating proximally out of the interior passage 22 and away from the anchor body 4 during anchor actuation or subsequent tissue approximation. At the conclusion of the longitudinal anchor collapse sequence, the soft anchor 2 is in the anchored configuration C2, which has an anchor profile as shown in FIG. 2B. The inventors have observed, through testing, that the soft anchor 2 of the illustrated embodiment exhibits a rapid and smooth longitudinal anchor collapse sequence that terminates in a relatively sudden, secure stop, which altogether provides the user with a positive tactile feedback indicating the occurrence of anchor actuation (i.e., achieving the anchored configuration C2).

Figures 7A, 7B, 7C:
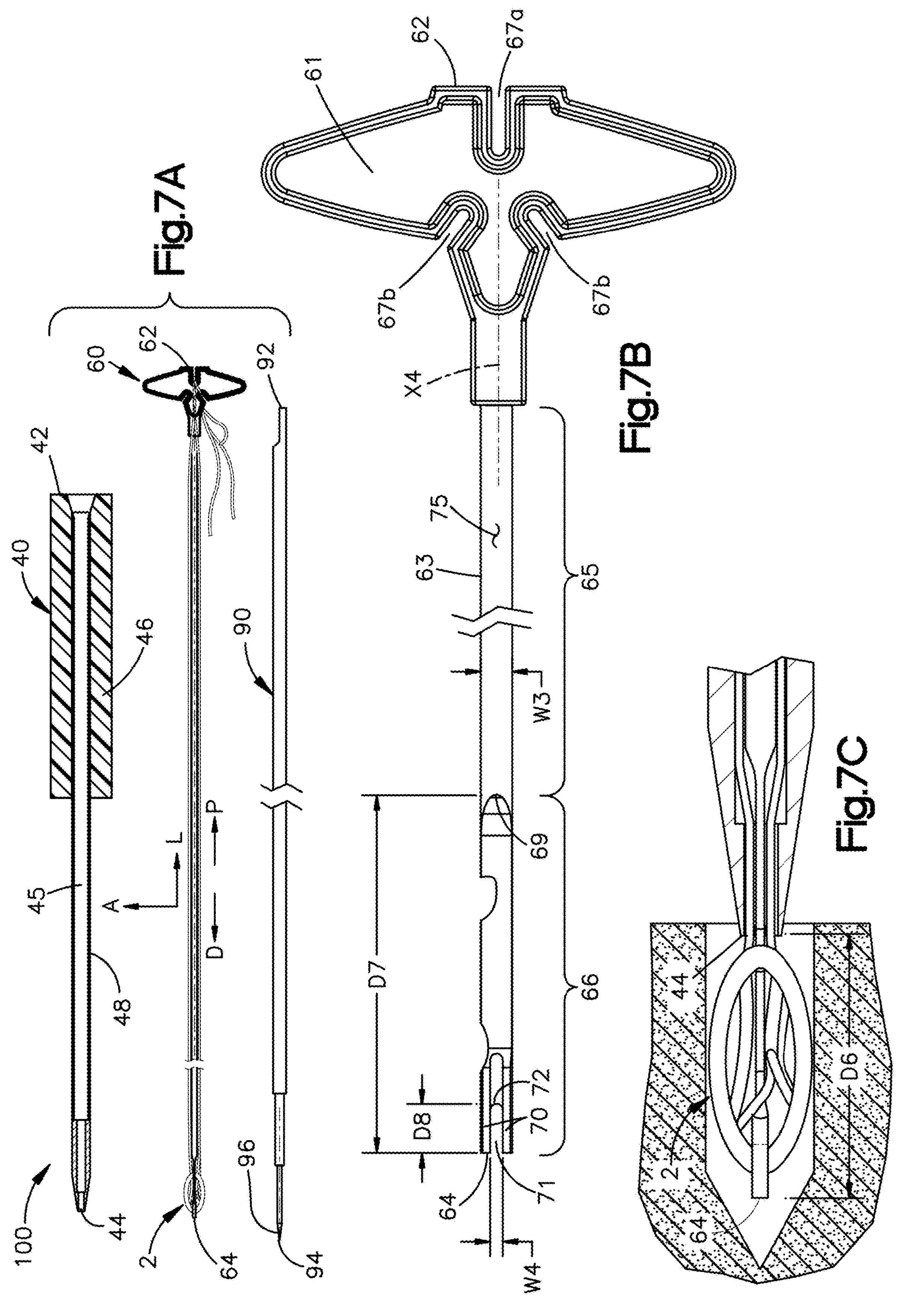
FIG. 7A is a plan assembly view of a surgical instrument assembly configured for deploying the tissue repair assembly illustrated in FIG. 1A to a treatment site of a patient, according to an embodiment of the present disclosure.
FIG. 7B is a side plan view of an inserter fork of the surgical instrument assembly illustrated in FIG. 7A.
FIG. 7C is a front plan view of a distal region of the inserter fork protruding from a distal portion of an access member of the surgical instrument assembly illustrated in FIG. 7A.
Figure 7G:
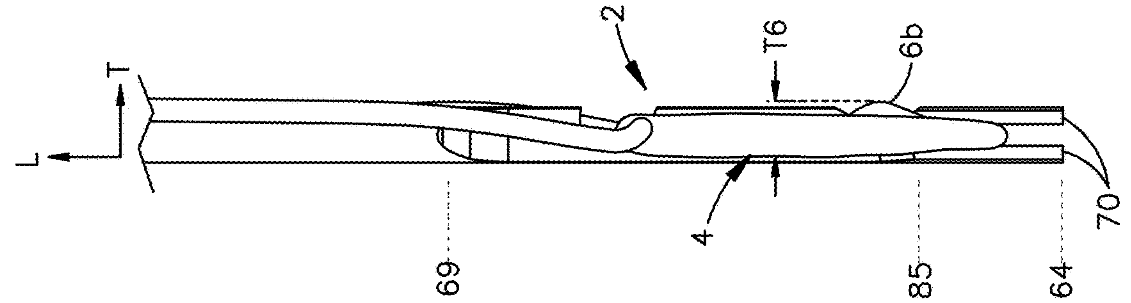
FIGS. 7F and 7G are respective front and side plan views of the distal region of the inserter fork, shown carrying the soft anchor illustrated in FIG. 2A.
Figure 7F:
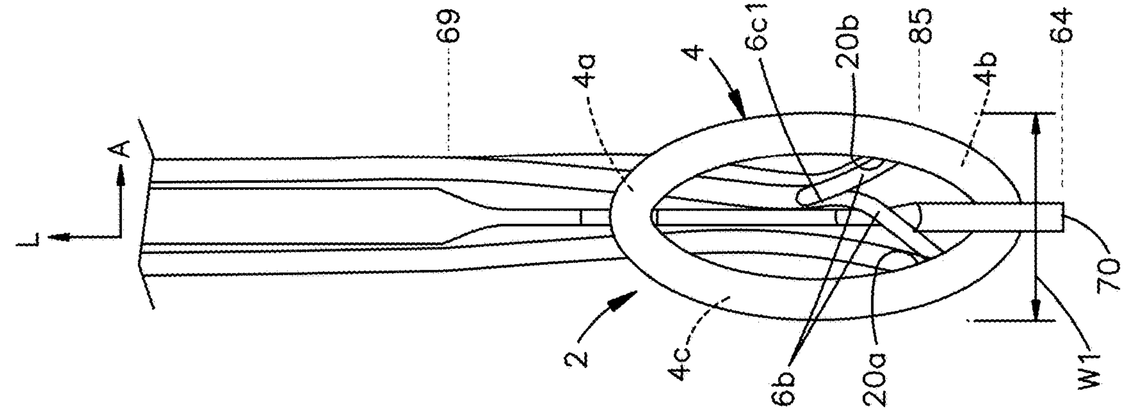

Referring now to FIGS. 7A-7G, an exemplary instrument assembly 100 for deploying the repair assembly 1 will now be described. As shown in FIG. 7A, the instrument assembly 100 includes an access member 40 and an insertion instrument or "inserter" 60 that is configured to carry and advance the repair assembly 1 through a cannulation 45 of the access member 40 and to the target site 3 of the first anatomical structure 5. The instrument assembly 100 also preferably includes an opening creating member 90, such as a drill member 90, that is configured to create an opening, such as a hole, in the first anatomical structure 5. In such instances, the opening (e.g., hole) becomes the target site 3 for insertion of the anchor body 4. The access member 40, inserter 60, and opening creating member 90 each have a respective proximal end 42, 62, 92 and a respective distal end 44, 64, 94 spaced from each other along a respective longitudinal direction. It should be appreciated that, because the respective longitudinal directions of the access member 40, inserter 60, and opening creating member 90 are configured to align with each other and with the longitudinal direction L of the repair assembly 1 during use, longitudinal direction L is also used herein to refer to the respective longitudinal directions of the access member 40, inserter 60, and opening creating member 90. Similarly, the lateral direction A and the proximal and distal directions P, D used above also apply to each of the access member 40, inserter 60, and opening creating member 90. It should be appreciated that the opening creating member 90 can be configured to advance through the cannulation 45 of the guide member 40 to create the opening 3 (e.g., hole 3), and to withdraw back out of the access member 40, prior to insertion of the inserter 50 through the cannulation 45 and into the target location 3. Thus, the access member 40 can be a multi-use instrument, in which one use is to provide passage for the opening creating member 60 to the first anatomical structure 5, and another use is to provide passage for the repair assembly 1 loaded on the inserter 60 to the target site 3. As shown, the opening creating member 90 can be a drill having a drill tip 96 at the distal end 94. In other embodiments, the opening creating member can be an awl or other hole-forming device.

The access member 40 includes a handle portion 46 (also referred to herein as an "access handle" 46) at the proximal end 42 and an elongate sleeve portion 48 (also referred to herein as a "sleeve" 48) that extends from the access handle 46 to the distal end 44. The cannulation 45 extends distally from the proximal end 44, through the access handle 46 and through the sleeve portion 48 to the distal end 44. The cannulation 45 can have a funnel-like lead-in portion at the proximal end 42. The distal end 44 of the access member 40 can configured to obtain and maintain purchase with the first anatomical structure 5. For example, the distal end 44 of the access member 40 can have a sawtooth configuration, a fish-mouth configuration, or other such configurations known in the art. The sleeve portion 48 can also include one or more visualization windows at or near the distal end 44 for providing a surgeon with a view of instrumentation within the cannulation 45 at or near the distal end 44 during use, such as the drill member 90 and/or the repair assembly 1. The sleeve portion 48 can be straight, as shown; alternatively, however, one or more regions of the sleeve portion 48, such as distal regions extending to or near the distal end 44, can extend along an arcuate pathway, which can be advantageous for accessing certain regions of patient anatomy.

Referring now to FIG. 7B, the inserter 60 has a handle portion 61 (also referred to herein as an "insertion handle" 61) at the proximal end 62 and an elongate portion 63 (also referred to herein as an "insertion rod" 63) extending distally from the insertion handle 61 to the distal end 64. A proximal region 65 of the insertion rod 63 has an outer surface 75, which can have a generally circular cross-sectional profile in a plane orthogonal to a longitudinal axis X5 of the inserter 60. The proximal region 65 defines a cross-sectional dimension or width W3, which can be substantially constant along the length of the proximal region 65 or can taper or otherwise narrow as it extends distally. A distal region 66 of the insertion rod 63 extends to the distal end 64 and has a fork-like geometry configured to carry the anchor body 4 thereon in the insertion configuration C1 during use. Accordingly, the distal region 66 can be referred to herein as a "fork" 66, and will be discussed in more detail below.

The insertion handle 61 preferably has grip formations for providing ease of grip and manipulation by a user during use. The insertion handle 61 also preferably includes one or more retention structures 67*a,b* configured to retain one or more proximal portions of the repair assembly 1 in desired configuration(s) during use while the anchor body 4 is loaded on the fork 66. As shown, the one or more retention structures can include a first retention recess or "cleat" 67*a* extending distally from the distal end 62 of the inserter 60, preferably centered along a longitudinal axis X5 of the inserter 60. The one or more retention structures can also include a pair of second retention recesses or cleats 67*b* extending generally proximally from a distal face of the insertion handle 61 toward the first cleat 67*a*. The first cleat 67*a* and one or both of the second cleats 67*b* can be employed as needed before and during use to retain the joined actuation tail 6*d* and the snake tails 8*b*1, 8*b*2 in a manner to provide a desired tension level on the tails 6*d*, 8*b*1, 8*b*2 during use while the anchor body 4 is loaded on the fork 66. A distal end 68 of the insertion handle 61 preferably defines a distal-facing shoulder configured to abut an associated structure of the access handle 46 to provide a predetermined protrusion distance D6 by which the distal end 64 of the inserter 60 (and thus the anchor body 4 loaded on the fork 66) extends distally beyond the distal end 44 of the access member 40 when the insertion rod 63 is fully inserted through the cannulation 45, as shown in FIG. 7C. It should be appreciated that the instrument assembly 100, including the access member 40, inserter 60, and opening creating member 90 thereof, can be generally configured based upon the VERSALOOPTM Soft Anchor Instrumentation design, distributed by DePuy Mitek, Inc., of Raynham, Massachusetts, U.S.A.

Referring now to FIGS. 7B-7F, the fork 66 is configured to carry the anchor body 4 securely through the cannulation 45 of the access member 40 (FIG. 7A) and to the target site 3 (such as a hole 3 predrilled into bone 5), and also to detach and withdraw cleanly from the anchor body 4 proximally out of the cannulation 45 so that the anchor body 4 remains at the target site 3 following fork withdrawal. For this purpose, the fork 66 described herein has various unique structural features that represent advancements over previous fork designs, specifically to accommodate the soft anchor 2 described above. The fork 66 is configured to carry the anchor body 4 thereon in the insertion configuration C1, particularly so that the anchor loop 14 is longitudinally elongated (e.g., tensioned or stretched, so to speak) on the fork 66 to reduce the maximum width of the anchor body 4 as it advances distally through the cannulation 45 and to/into the target site 3. This also presents the tapered distal portion 4*b* of the anchor body 4 as the leading anchor structure during anchor insertion, which reduces friction at the anchor-to-bone interface during anchor insertion into the pre-drilled hole 3, thereby facilitating smooth anchor insertion into the pre-drilled hole 3. To accommodate the soft anchor 2 in the insertion configuration C1, the fork 66 defines a fork length D7, measured longitudinally from a proximal fork end 69 to the distal end 64, that is preferably greater than the first maximum length L1 of the anchor body 4. The proximal fork end 69 can be located at an interface between the proximal region 65 and the fork 66. The fork 66 includes one or more tines 70, such as a pair of tines 70, that extend to and define the distal end 64 of the inserter 60. It should be appreciated that the distal end 64 of the inserter 60 can be referred to synonymously as the distal end of the insertion rod 63, of the fork 66, and/or of the tines 70. The tines 70 also define a gap 71 therebetween defining a gap width W4 measured between inner surfaces of the tines 70 along the lateral direction A. The gap 71 also has a gap depth D8 measured longitudinally from the distal end 64 to a proximal end surface 72 defined by the fork 66. The gap width W4 and depth D8 are sized to hold the distal portion 4*b* of the anchor body 4 securely in the gap 71 as the anchor body 4 through the cannulation 45 and to the target site 3, yet also to decouple and withdraw cleanly from the anchor body 4 while the anchor body 4 remains at the target site 3. According to non-limiting examples, the width W4 can be up to about 4.0 mm, and the gap depth D8 can be up to about 5.0 mm.

Additionally, the fork 66 of the illustrated embodiment has lateral and transverse profiles that are configured to facilitate secure attachment to, and clean detachment from, the anchor body 4. For example, FIG. 7D shows the transverse profile of the fork 66, i.e., the profile of the fork 66 in a plane extending along the transverse and longitudinal directions T, L. As viewed in this transverse profile, the fork 66 defines first and second outer surfaces 74, 76 transversely opposite each other, with a proximal recess 78 and a distal recess 80 each extending transversely from the second outer surface 76 toward the first outer surface 74. The proximal recess 78 is configured for part of proximal portion 4*a* of the anchor body 4 to reside therein when the anchor body 4 is loaded onto the fork 66. The proximal recess 78 has a proximal surface portion 78*a* and a distal surface portion 78*b*. The proximal surface portion 78*a* defines a first relief angle A1 with respect to the longitudinal axis X5 of the inserter 60. The distal surface portion 78*b* defines a second relief angle A2 with respect to the longitudinal axis X5. As shown, the second relief angle A2 can be greater than the first relief angle A1, which helps the fork 66 withdraw proximally from, and decouple from, the anchor body 4 after the anchor body 4 has been inserted to/in the target location 3. According to non-limiting examples, the first relief angle A1 can be in a range from about 70 degrees to about 135 degrees, and the second relief angle can be in a range of about 95 degrees to about 170 degrees. The distal recess 80 is configured for part of one or both of the actuation tails 6*b* to reside therein when the anchor body 4 is loaded onto the fork 66, particularly the part(s) of the actuation tails 6*b* extending proximally from the respective first or second location 20*a*,*b* to the first joint location 6*c*1. The distal recess 80 can have a radiused transverse profile, as shown. The distal recess 80 can have a shallower recess depth than that of the proximal recess 78, as shown in FIG. 7D. In the illustrated embodiment, the fork 66 has a substantially constant transverse fork thickness T5, as measured between the first and second outer surfaces 74, 76 along the transverse direction T, except at the proximal and distal recesses 78, 80. The transverse fork thickness T5 can be substantially equivalent to the width W3 of the insertion rod 63 along the proximal portion 65 thereof, such that the insertion rod 63 can have a substantially consistent transverse profile (except at the proximal and distal recesses 78, 80). It should be appreciated that, in other embodiments, the fork 66 need not have the proximal recess 78 and/or the distal recess 80.

Figure 7E:
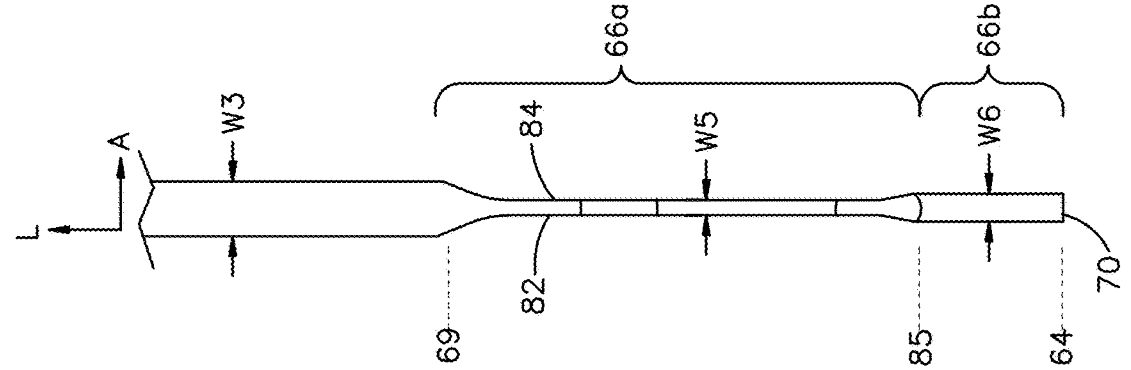
FIGS. 7D and 7E are respective side and front plan views of the distal region of the inserter fork illustrated in FIG. 7B.
Figure 7D:
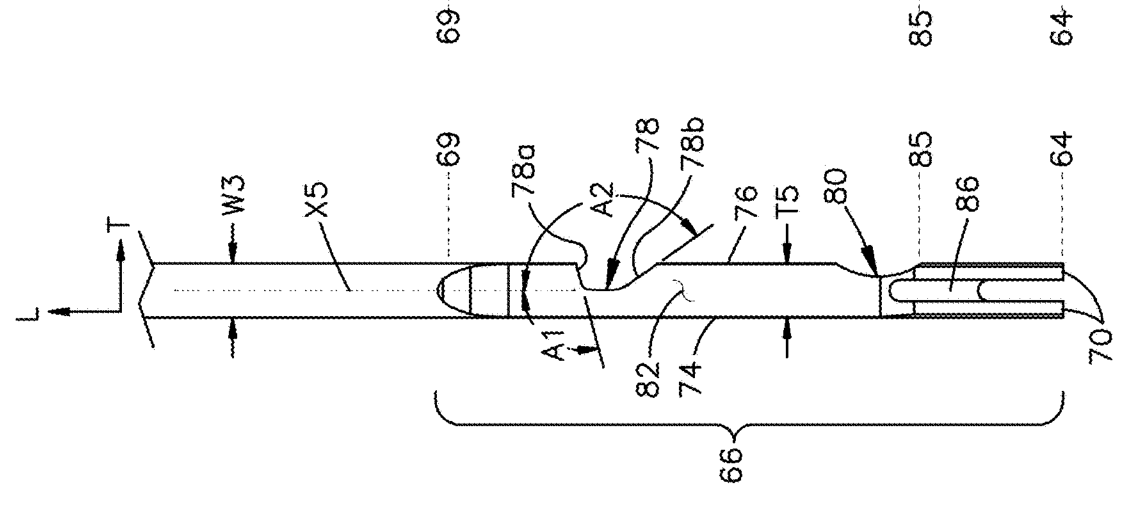

Referring now to FIG. 7E, which shows the lateral profile of the fork 66, i.e., the profile of the fork 66 in a plane extending along the lateral and longitudinal directions A, L. As viewed in this lateral profile, the fork 66 defines a third outer surface 82 and a fourth outer surface 84 that are laterally opposite each other. It should be appreciated that the fork 66 can have a proximal fork portion 66*a* and a distal fork portion 66*b* that are longitudinally spaced from each other. The proximal fork portion can extend from the proximal fork end 69 to a shared boundary 85 with the distal fork portion 66*b*, and the distal fork portion 66*b* can extend from the shared boundary 85 to the distal end 64 of the fork 66. The shared boundary 85 is preferably positioned to be substantially coincident with the boundary between the intermediate and distal portions 4*c*,4*d* of the anchor body 4 when the anchor body 4 is loaded on the fork 66. Accordingly, in the illustrated embodiment, the distal fork portion 66*b* is configured to accommodate the distal portion 4*b* of the anchor body 4 while the proximal fork portion 66*a* is configured to accommodate the intermediate and proximal portions 4*c*,*b* of the anchor body 4. Additionally, one or both of the proximal and distal fork portions 66*a,b* preferably has a narrower lateral profile (FIG. 7E) than the transverse profile of the fork 66 (FIG. 7D). In the illustrated embodiment, the proximal fork portion 66*a* defines a proximal fork width W5 along the lateral direction A, and the distal fork portion 66*b* defines a distal fork width W6 along the lateral direction A. It should be appreciated that the proximal and distal fork widths W5, W6 are each measured laterally between the third and fourth outer surfaces 82, 84 along the respective proximal and distal fork portions 66*a,b*. As shown, the proximal fork width W5 is narrower than the distal fork width W6, and both of which (W5 and W6) are narrower than the transverse fork thickness T5 and the width W3 of the proximal portion 65 of the insertion rod 63. In this manner, the third and fourth outer surfaces 82, 84 effectively define lateral cut-outs or recesses from outer surface 75, which allows the fork 66 to accommodate the anchor body 4 when loaded onto the fork 66. Additionally, as shown in FIG. 7D, the distal fork portion 66*b* can include lateral recesses or slots 86, which can be positioned between the tines 70 with respect to the lateral direction A and which can extend inwardly toward each other from the third and fourth outer surfaces 82, 84, respectively. Although only one such slot 86 is visible in FIG. 7D, it should be appreciated that another such slot 86 can be positioned transversely opposite therefrom on the distal fork portion 66*b*.

The foregoing features of the fork 66 provide the fork 66 with a geometry that is specifically tailored to the geometry of the repair assembly 1, particularly along the anchor body 4 thereof. This tailored fork geometry 66 helps reduce the first maximum width W1 along the lateral direction A (FIG. 7F), and also helps reduce a first maximum thickness T6 of the anchor body 4 along the transverse direction T (FIG. 7G), when the anchor body 4 is loaded on the fork 66. This advantageously facilitates anchor body 4 insertion through cannulation 45 of the access member 40 and to the target site 3. It should be appreciated that various adjustments to the fork 66 geometry described above are within the scope of the present disclosure.

Figure 8A:
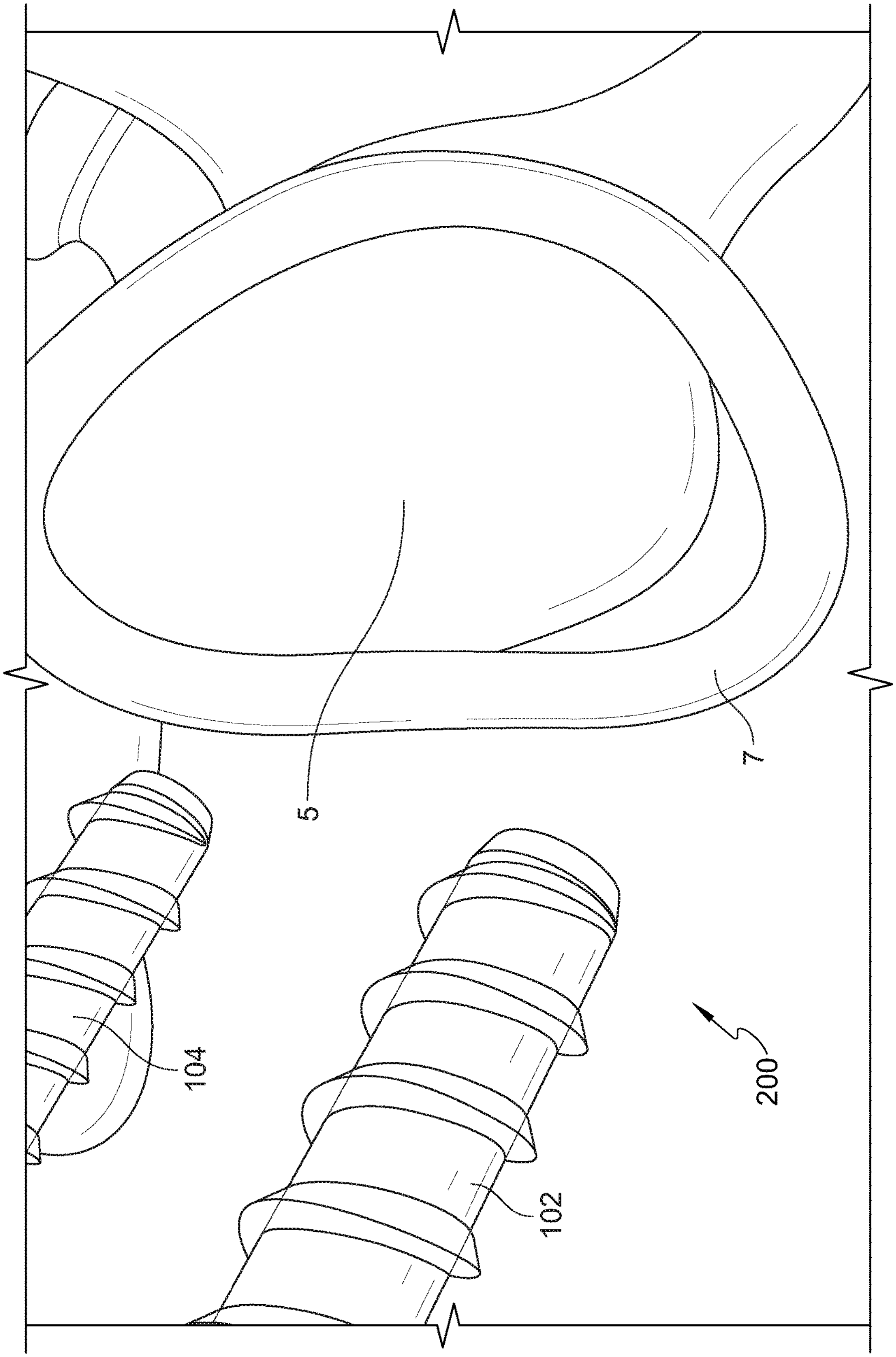
FIGS. 8A-8Q are perspective views of components of a surgical system, shown at various stages of a surgical method for a labrum glenoid repair that employs the tissue repair assembly illustrated in FIG. 1A, according to an embodiment of the present disclosure.
Figure 8E:
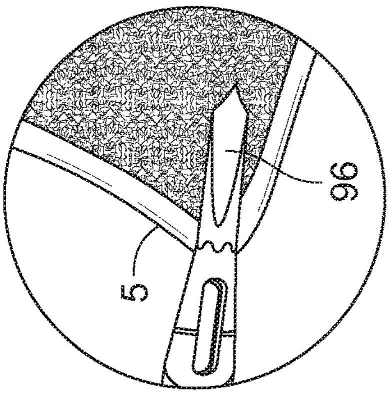
Figure 8F:
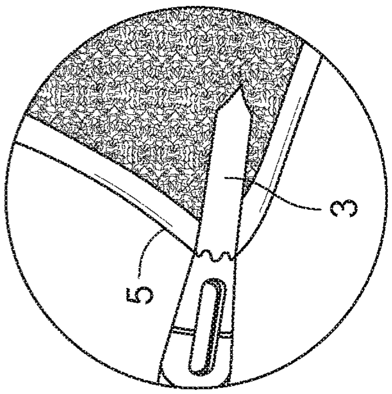
Figure 8C:
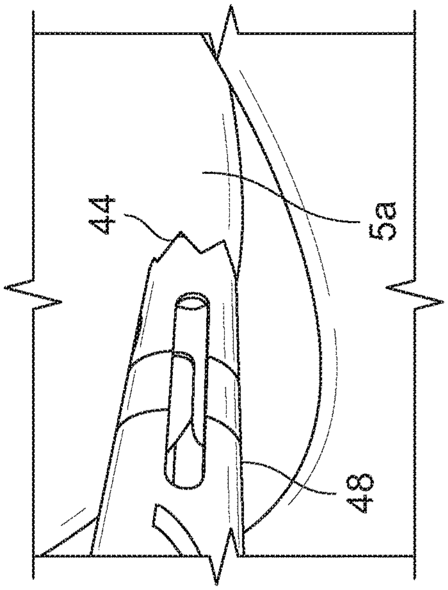
Figure 8D:
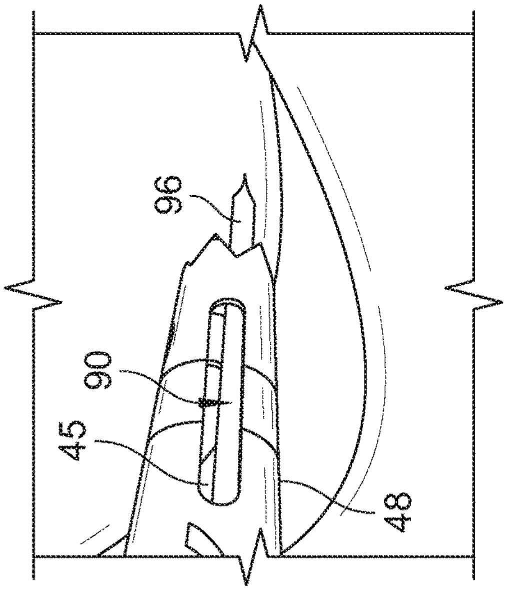
Figure 8B:
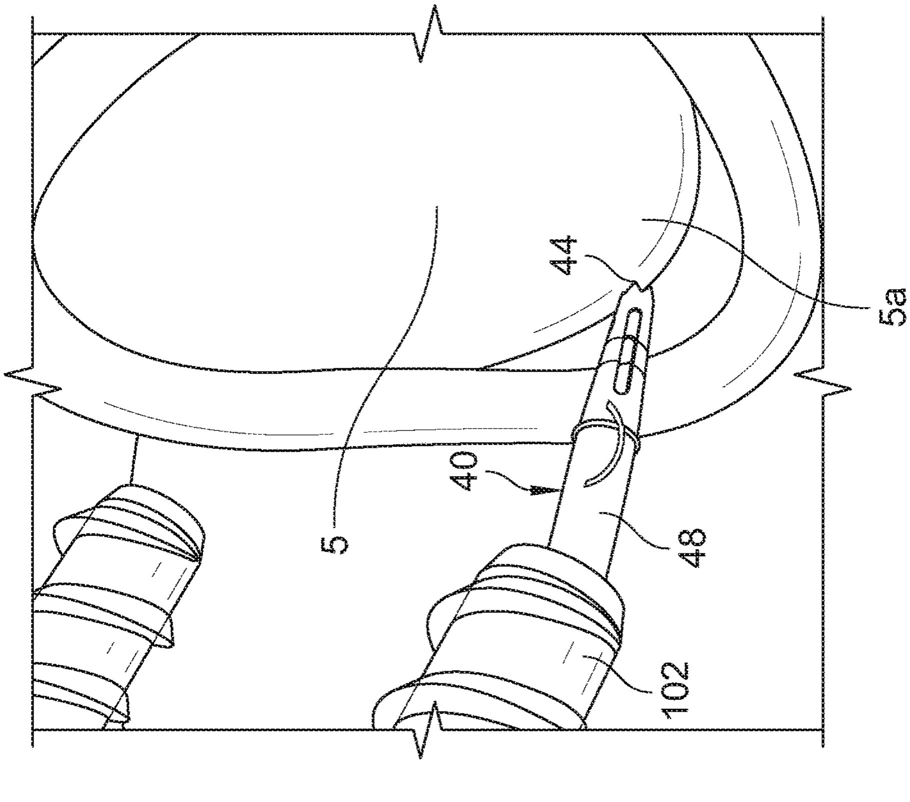
Figure 8G:
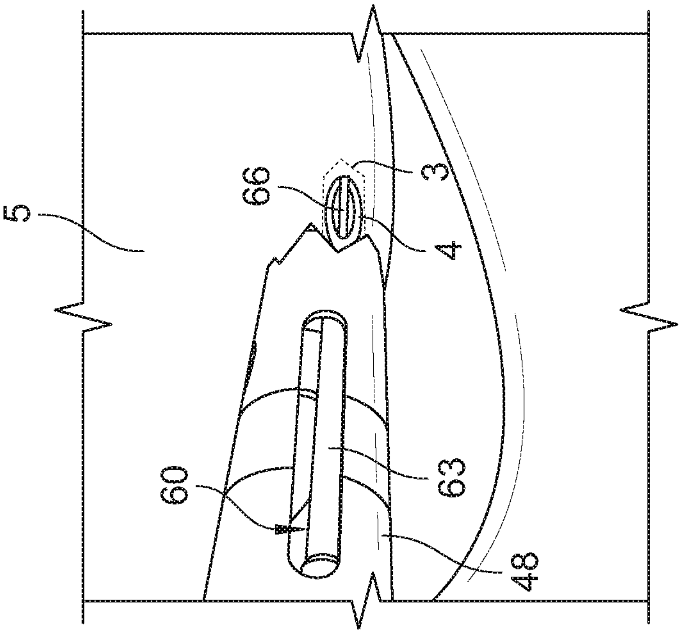
Figure 8H:
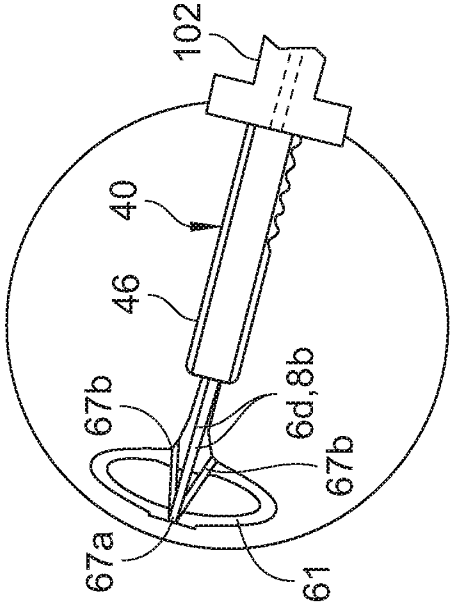
Figure 8I:
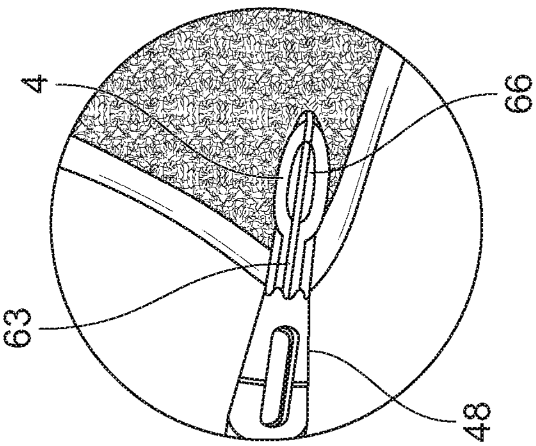
Figure 8J:
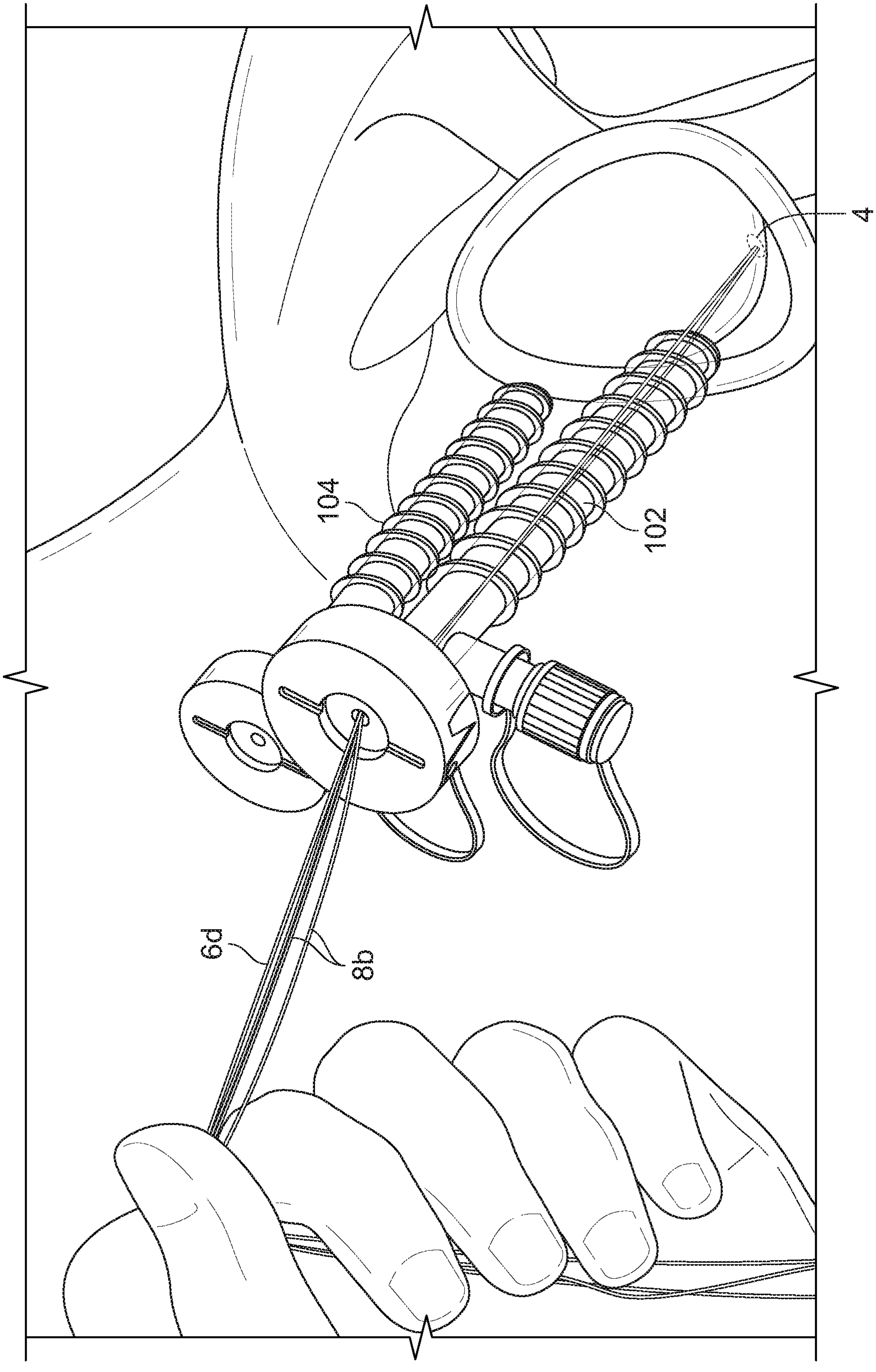
Figure 8L:
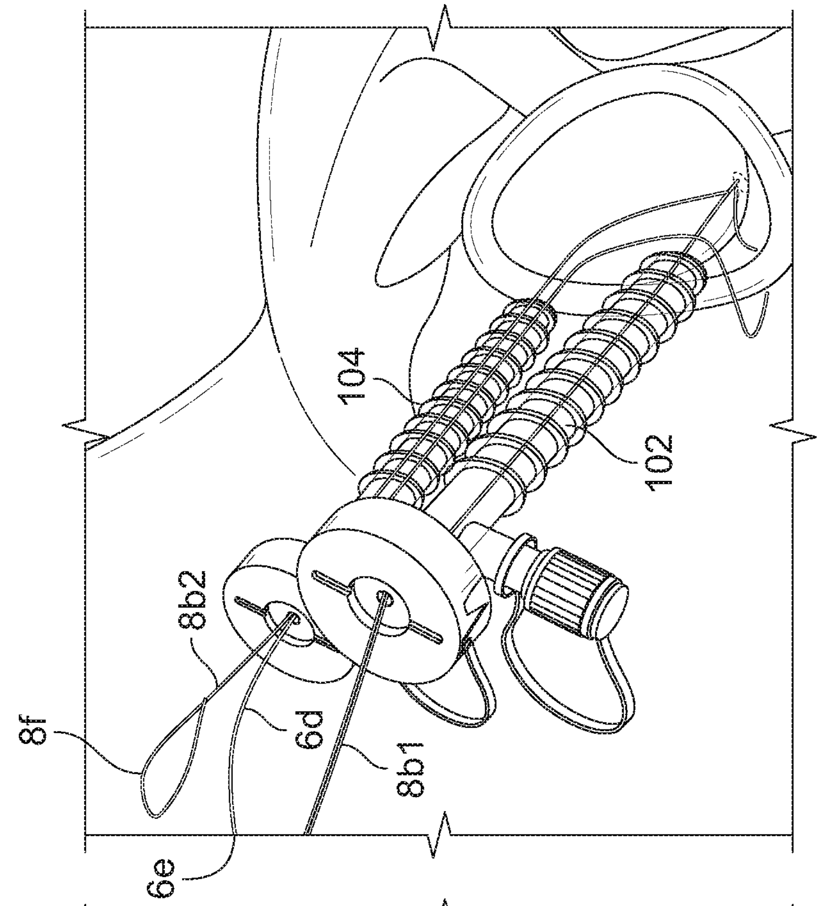
Figure 8K:
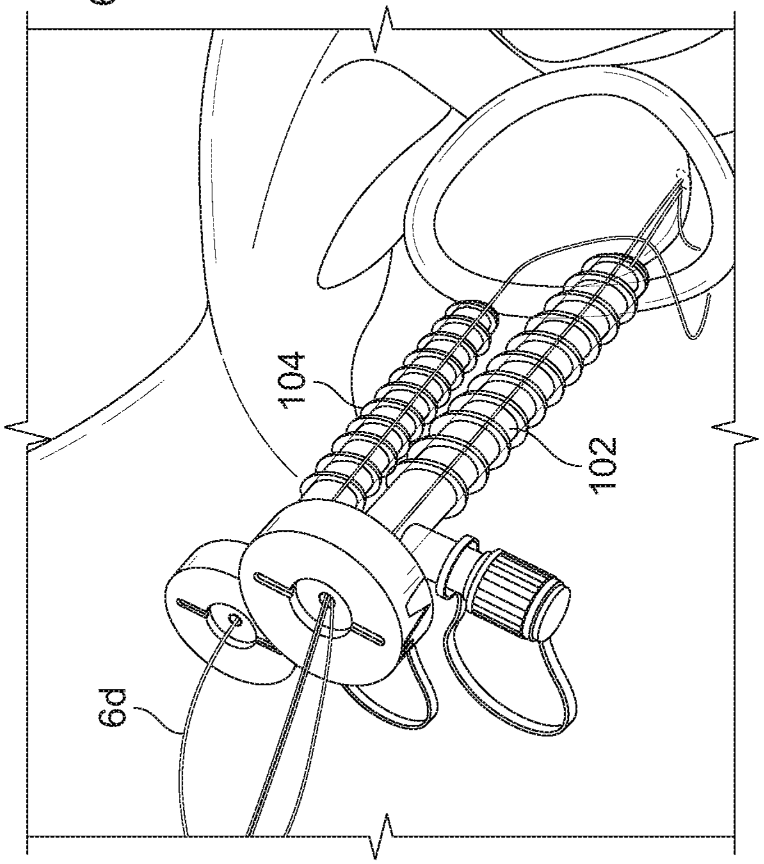
Figure 8N:
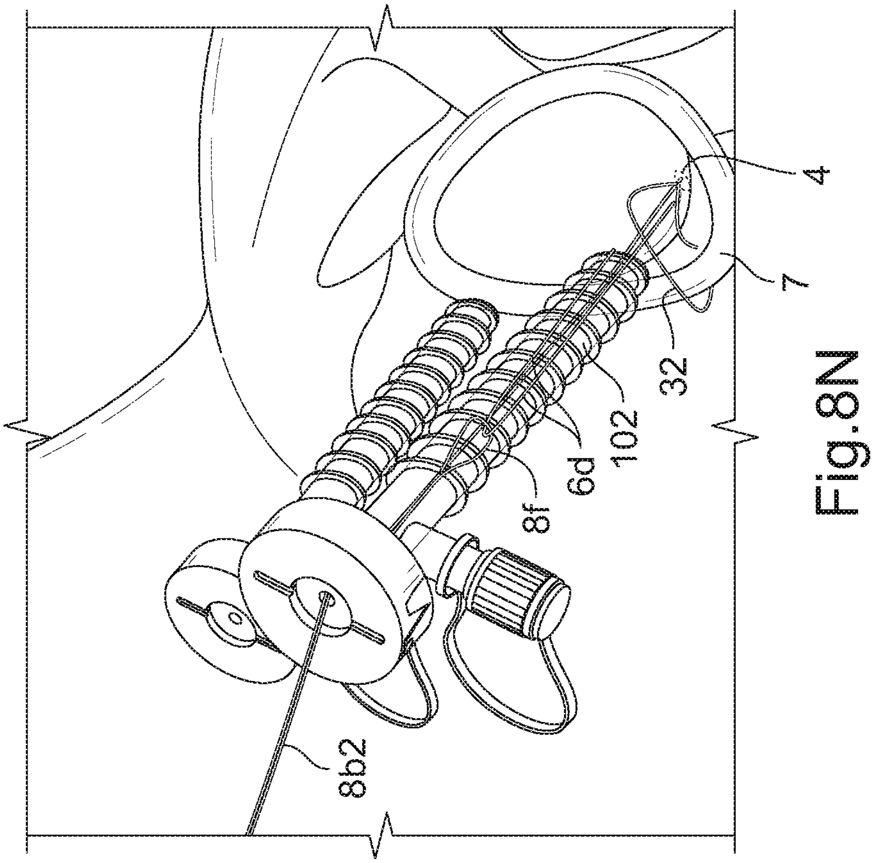
Figure 8M:
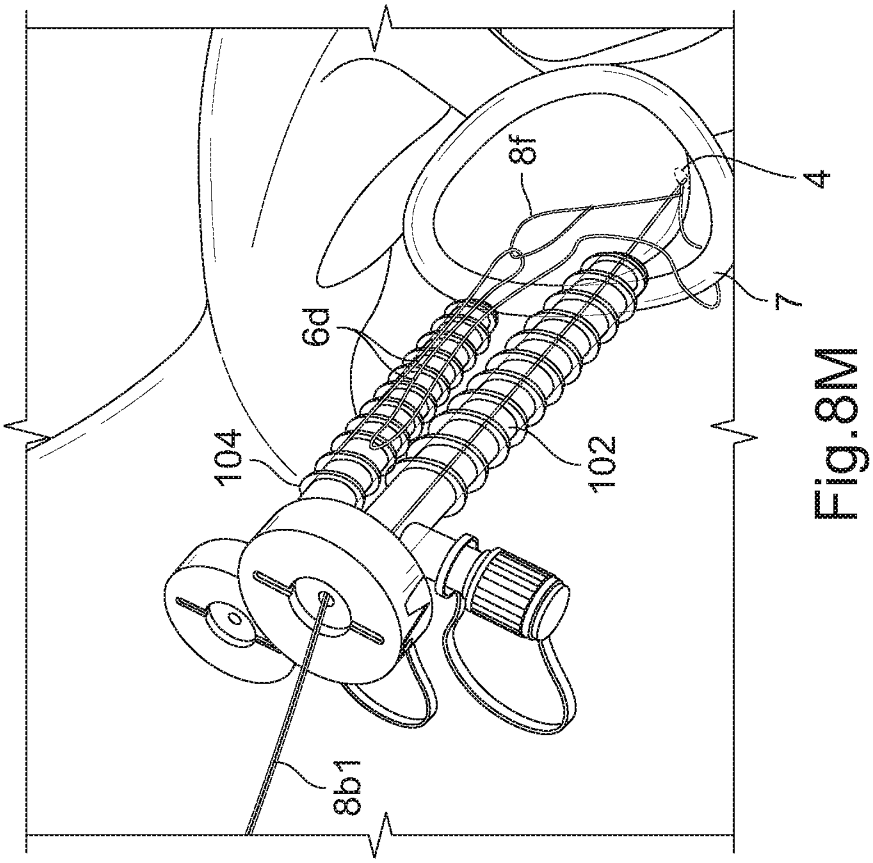
Figure 8P:
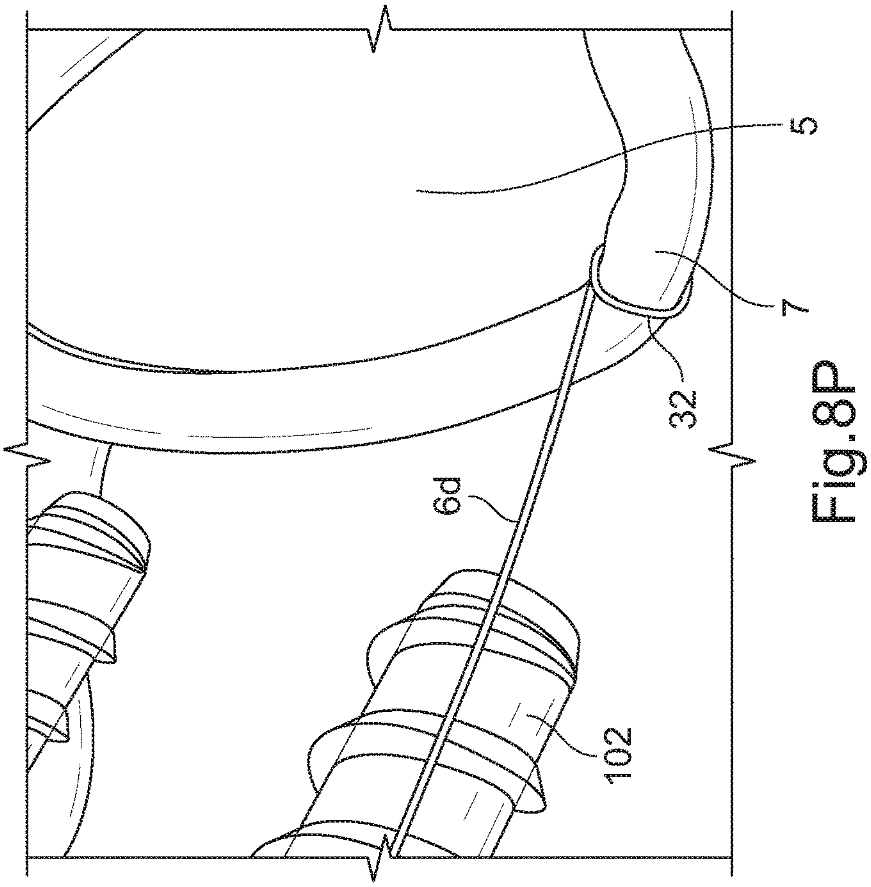
Figure 8O:
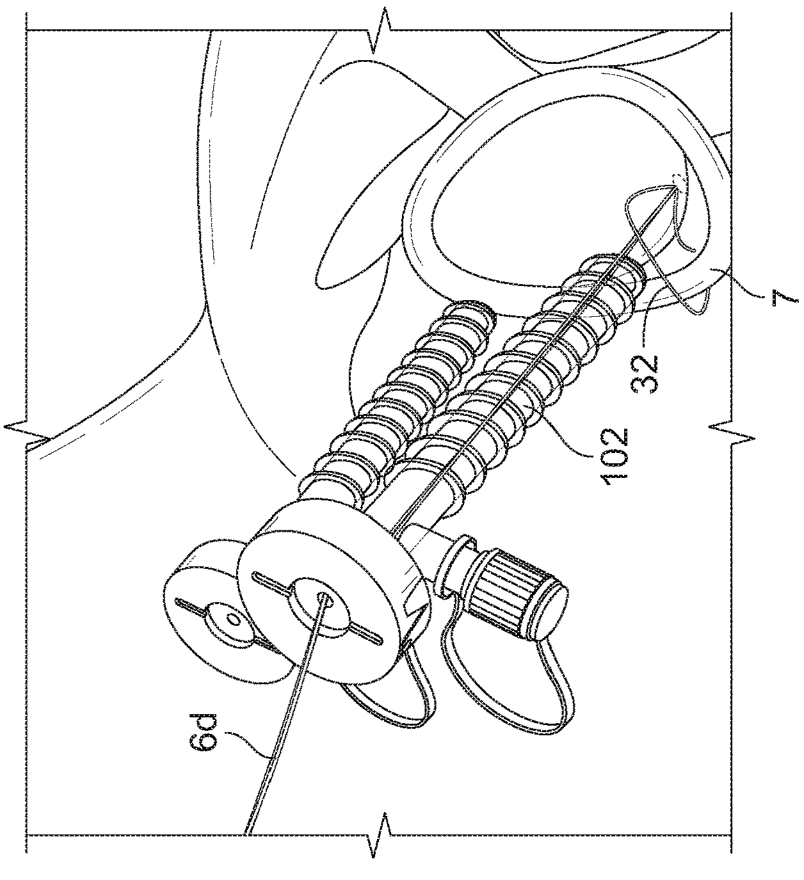
Figure 8Q:
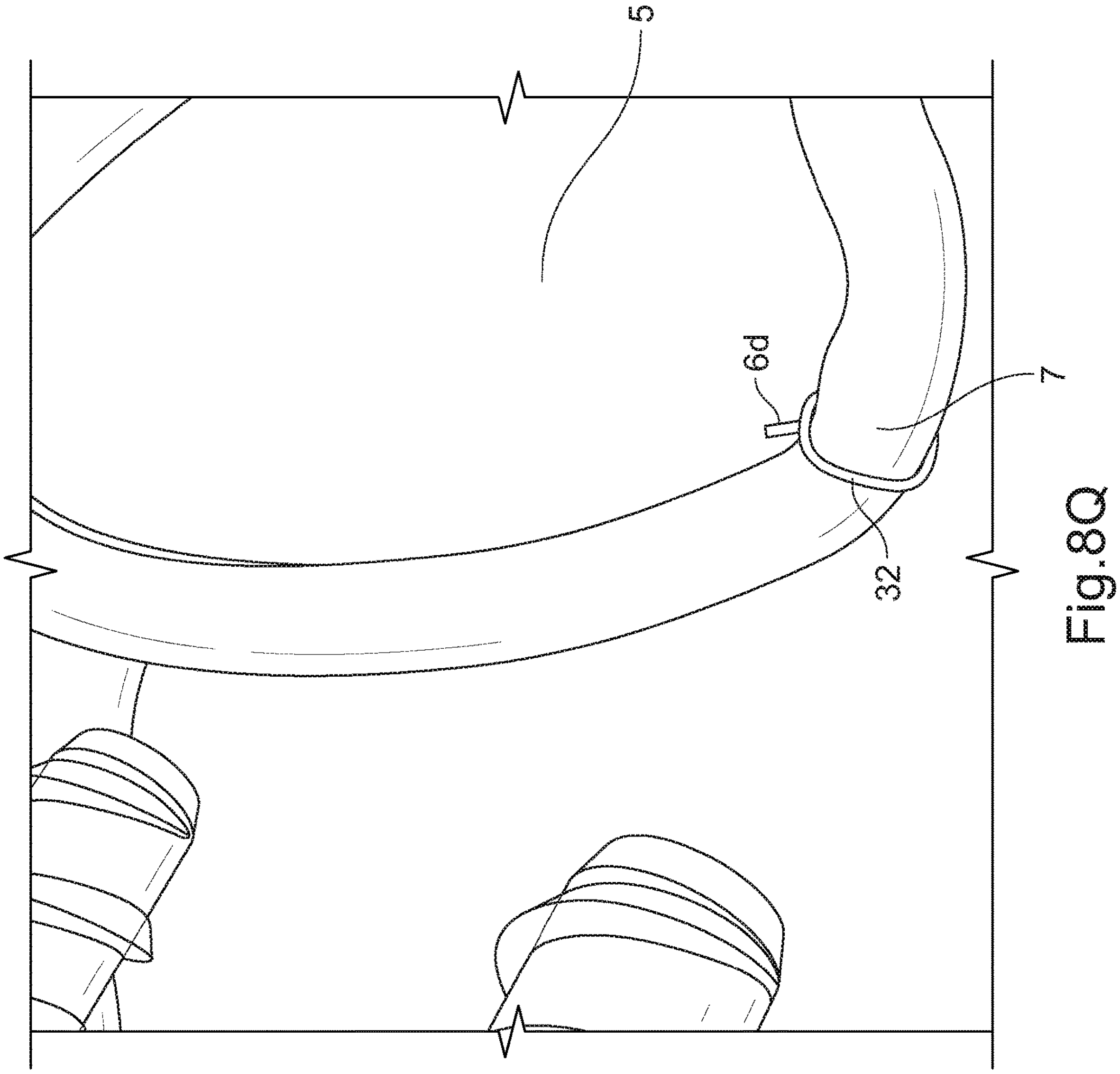

Referring now to FIGS. 8A-8Q, an exemplary method will be described for employing the instrument assembly 100 within a surgical system 200 to repair a labrum of a shoulder joint, particularly according to a labrum glenoid repair. In this exemplary method, the repair assembly 1 is employed to approximate a detached portion of the labrum to the glenoid. Using the terminology set forth above, in this example the glenoid represents the first anatomical structure 5 and the labrum represents the second anatomical structure 7. Although this exemplary method refers to actions or steps as being performed by a surgeon, it should be appreciated that one or more of these steps can be performed by a physician, technician, or other medical professional.

Referring now to FIG. 8A, a first cannula 102 and a second cannula 104 of the surgical system 200 are positioned through soft tissue along respective trajectories that extend toward the glenoid 5. The first cannula 102 can be positioned inferior with respect to the second cannula 104, which can therefore be positioned superior with respect to the first cannula 102.

As shown in FIG. 8B, the sleeve 48 of the access member 40 is inserted through the first cannula 102 and advanced distally so that the distal end 44 of the sleeve 48 advances toward the glenoid 5, preferably toward the glenoid rim 5*a*. The surgeon continues advancing the sleeve 48 until the distal end 44 purchases on the glenoid, particularly on the glenoid rim 5*a*, as shown in FIG. 8C. With the sleeve 44 purchased on the glenoid 5, the surgeon introduces the opening creating member 90 through the cannulation 45 of the access member 40 and advances the opening creating member 90 distally so that the drill tip 96 at the distal end 94 of the opening creating member 90 forms a hole 3 in the glenoid 5, as shown in FIGS. 8D-8E. Afterward, the opening creating member 90 is withdrawn proximally from the cannulation 45 of the access member 40, exposing the hole 3, as shown in FIG. 8F.

Subsequently, as shown in FIGS. 8G-8H, the insertion rod 63 of the inserter 60, with the repair assembly 1 coupled to the fork 66 thereof, is introduced into and advanced through the cannulation 45 of the access member 40 until the anchor body 4 is inserted at a desired depth within the hole 3 in the glenoid 5. When the insertion handle 61 is fully seated against the access handle 46, as shown in FIG. 8H, the desired anchor depth within the hole, shown in FIG. 8I, can be a function of the predetermined protrusion distance D6, which was described above with reference to FIG. 7C. After the anchor body 4 is inserted at the desired depth (or at least at a sufficient depth) within the hole 3, the surgeon decouples the snake tails 8*b* and the joined actuation tail 6*d* from the cleats 67*a,b*. Subsequently, the surgeon withdraws the access member 40 and the inserter 60 proximally from the first cannula 102, leaving the anchor body 4 positioned within the hole 3 at the desired (or at least sufficient) depth, and with the snake tails 8*b* and the joined actuation tail 6*d* extending proximally through and outwardly from the first cannula 102.

Referring now to FIG. 8J, the surgeon pulls the snake tails 8*b* and the joined actuation tail 6*d* proximally to actuate the anchor body 4 into the anchored configuration C2 (which configuration C2 is shown in FIGS. 1B, 2B, and 5B).

Referring now to FIG. 8K, the surgeon can employ the second cannula 104 to pass the joined actuation tail 6*d* through the labrum 7 and out proximally through the second cannula 104. Although a simple stitch of the joined actuation tail 6*d* through the labrum 7 is shown, it should be appreciated that more complex stiches can be formed. It should also be appreciated that various suture passer, suture shuttle, and/or suture grasper instruments can be employed to pass the jointed actuation tail 6*d* through the labrum 7 and proximally through the second cannula 104.

Referring now to FIG. 8L, the surgeon retrieves the second snake tail 8*b*2 (with the snake loop 8*f* at the end thereof) proximally through the second cannula 104. At this stage, the joined actuation tail 6*d* and the second snake tail 8*b*2 extend proximally from the second cannula 104, while the first snake tail 8*b*1 extends proximally from the first cannula 102. The surgeon can then insert the free end 6*e* of the joined actuation tail 6*d* through the snake loop 8*f* (e.g., in a manner analogous to that shown in FIG. 5C). With joined actuation tail 6*d* extending through the snake loop 8*f*, the surgeon can pull the first snake tail 8*b*1 proximally from the first cannula 102, which thereby pulls the snake loop 8*f* distally back through the second cannula 104, which action also shuttles the joined actuation tail 6*d* (which extends through the snake loop 8*f*) distally through the second cannula 104 and back towards the anchor body 4, as shown in FIG. 8M (which is analogous to FIG. 5D). The surgeon continues pulling the first snake tail 8*b* proximally so that the snake loop 8*f* pulls the joined actuation tail 6*d* successively into, through, and then outwardly from the anchor body 4 and proximally upward into the first cannula 102, as shown in FIG. 8N. During this step, the joined actuation tail 6*d* replaces the snake member 8 as the length of suture that is gripped by the locking mechanism 26 within the interior passage 22 of the distal portion 4*b* of the anchor body 4, as discussed above with reference to FIGS. 5E-5F.

Referring now to FIG. 8O, the surgeon continues pulling the snake member 8 until the joined actuation tail 6*d* extends proximally from the first cannula 102, at which stage the actuation member 6 has been fully passed through the labrum and forms an adjustable approximation loop 32 around the labrum 7. Referring now to FIG. 8P, the surgeon pulls the joined actuation tail 6*d* proximally through the first cannula 102, thereby reducing the circumference of the approximation loop 32, which in turn approximates the captured portion of labrum 7 toward the glenoid 5 (also analogous to FIG. 5G). Referring now to FIG. 8Q, after the labrum 7 is fully approximated as desired, the surgeon preferably trims the free portion of the joined actuation tail 6*d* near the approximation loop 32. As described above, the locking mechanism 26 substantially locks the approximation loop 32 in the fully approximated configuration, thereby obviating the need to further tie-off the free portion of the joined actuation tail 6*d*, although the surgeon can elect to tie-off the free portion of the joined actuation tail 6*d* prior to trimming for purposes of redundancy.

It should also be appreciated that the exemplary methods described above can include various additional and/or alternative steps. It should also be appreciated that these exemplary methods can be adapted to repair other parts of anatomy while remaining within the scope of the present disclosure. One non-limiting example of such other anatomical repair includes a lateral ankle instability repair.

With reference to FIGS. 9A-15E, addition embodiments of tissue repair assemblies will be described.

With reference to FIGS. 9A-9G, another embodiment of a tissue repair assembly 201 for anatomical fixation (e.g., anatomical approximation) will now be described. The repair assembly 201 of the present embodiment, and the methods of using it to repair tissue, can be generally similar to those of the repair assembly 1 described above with reference to FIGS. 1A-6N. For example, the repair assembly 201 of the present embodiment includes an anchor body 4 and an actuation member 6 and a snake member 8 coupled to the anchor body 4 and extending therefrom. Moreover, the anchor body 4 and portions of the actuation member 6 and snake member 8 coupled thereto define a soft anchor 202 of the repair assembly 201. Additionally, like the embodiment above, the anchor 202 is adapted for insertion to the target location 3 of a first anatomical structure 5 while in an insertion configuration C1 (FIGS. 9A-9B), and is configured to transition from the insertion configuration C1 to an anchored configuration C2 (FIGS. 9C-9G), and is further configured to transition to an approximated configuration C3 (FIG. 9G) in which the first anatomical structure 5 and a second anatomical structure 7 are approximated. For the sake of brevity, the following discussion focuses mainly on differences employed in the repair assembly 201 relative to the repair assembly 1 described above. In the following discussion, features having similar design and function to those described above can employ the same reference numbers.

Figure 9A:
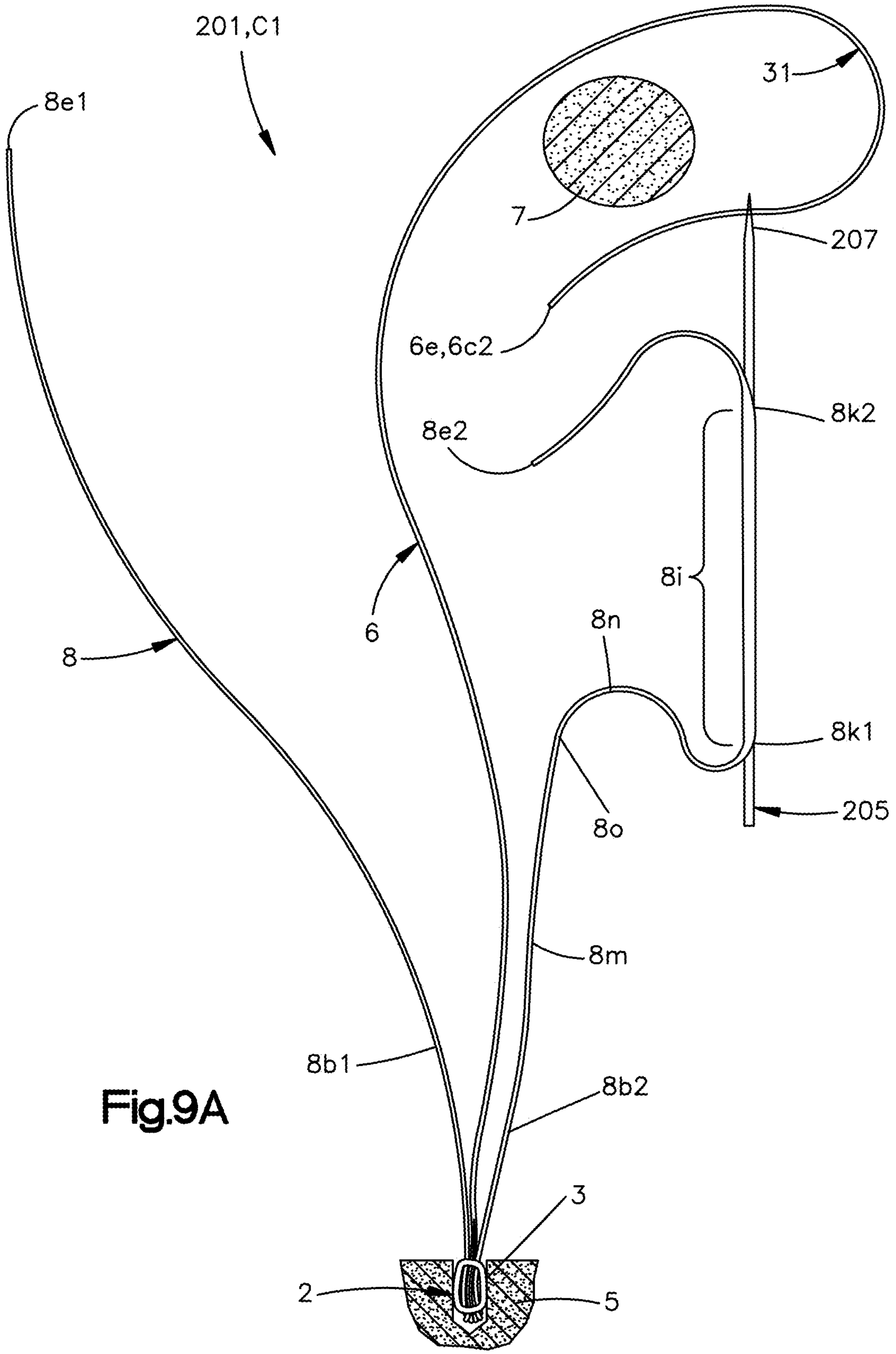
FIG. 9A is a front plan view of a tissue repair assembly according to another embodiment of the present disclosure, shown in an insertion configuration.
Figure 9B:
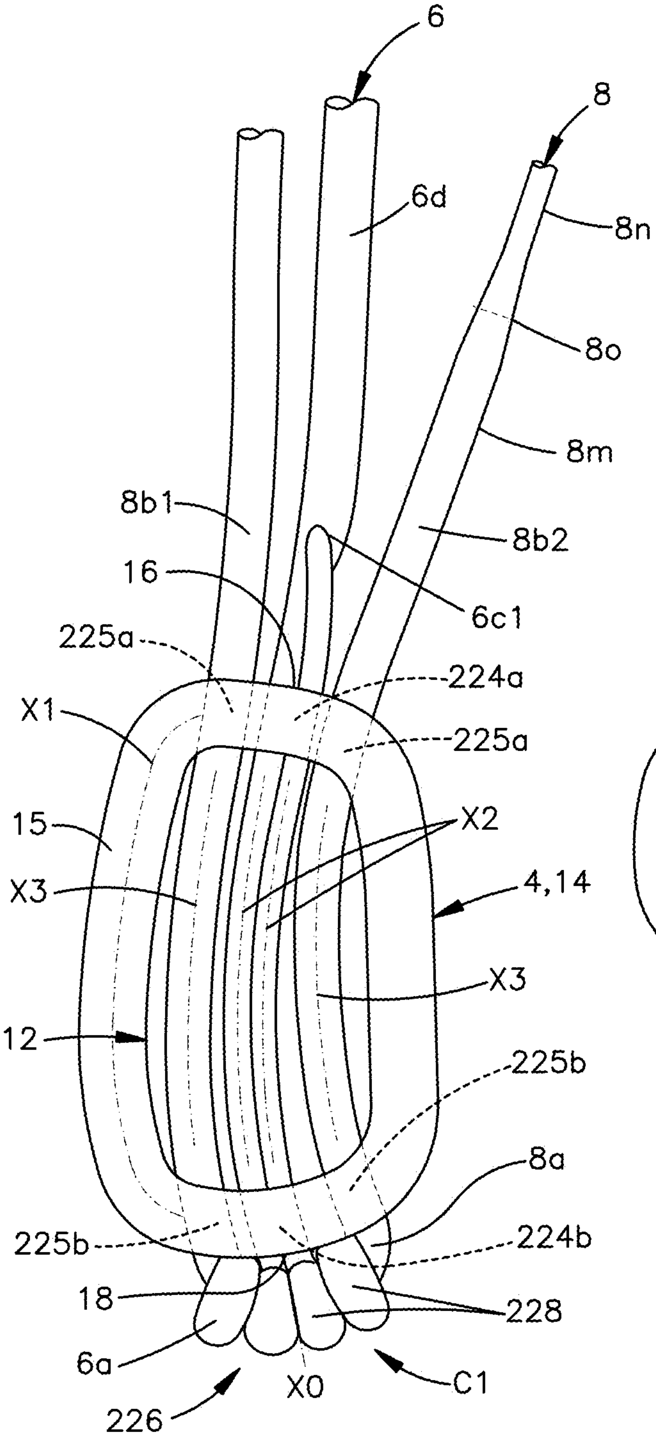
FIGS. 9B and 9C are front plan views of a soft anchor of the tissue repair assembly illustrated in FIG. 9A, shown in an insertion configuration (FIG. 9B) and in an anchored configuration (FIG. 9C)
Figure 9C:
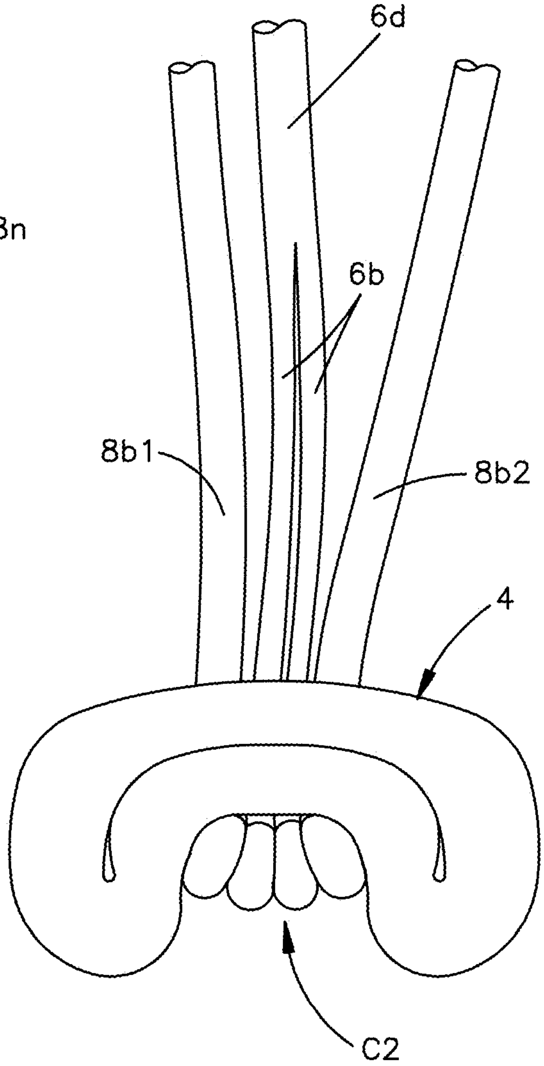

Referring now to FIG. 9B, the anchor body 4 can be configured into an anchor loop 14, which can be a closed loop, similar to the embodiment described above. In the present embodiment, the actuation member 6 and the snake member 8 can couple to each other in a manner defining a grip or "locking" mechanism 226 at a location that is distal of the distal end 18 of the anchor body 4. The actuation member 6 can extend proximally from the locking mechanism 226 through a distal penetration 224*b* through the anchor body 4, and through the anchor eyelet 12, and through a proximal penetration 224*a* through the anchor body 4. The snake member 8 can extend proximally from the locking mechanism 226 through respective distal penetrations 225*b* through the anchor body 4, and therefrom through the anchor eyelet 12, and through respective proximal penetrations 225*a* through the anchor body 4. Preferably, the proximal and distal penetrations 224*a,b* through which the actuation member 6 extends are coaxial with the insertion axis X0 of the anchor 2. Additionally, the proximal and distal penetrations 225*a,b* through which the snake member 8 extends are preferably equidistantly laterally spaced from the insertion axis X0. It should be appreciated that the proximal and distal penetrations 224*a,b*, 225*a,b* extend through respective segments of the anchor body 4 (i.e., between opposed sides of the jacket 15) along respective pathways that are substantially perpendicular to the central body axis X1 at their respective intersections therewith. Stated differently, the respective actuation member and snake member axes X2, X3 are substantially perpendicular to the central body axis X1 as they intersect it through the respective proximal and distal penetrations 224*a,b*, 225*a,b*.

The locking mechanism 226 of the presently illustrated embodiment is constructed as a two-turn prussik knot, in which the actuation member 6 defines the "turns" or loops 228 around the snake member 8. As a two-turn prussik knot, the actuation member 6 defines four (4) loops 228 around the snake member 8 at the location distal of the distal end 18 of the anchor body 4. Similar to the locking mechanism 26 described above, the locking mechanism 226 of the present embodiment provides one-way axial sliding of the snake member 8 (and thereafter the actuation member 6) through the loops 228 as the repair assembly 201 transitions from the anchored configuration C2 to the approximated configuration C3, and can thus be referred to as a "one-way locking mechanism" 226. It should be appreciated that the locking mechanism 226 can alternatively include any type of friction hitch knot such as a pile hitch or rolling hitch and can be scalable to any multitude of turns. By way of non-limiting examples, the locking mechanism 226 can include a one-turn prussik knot (having two (2) loops 228), a three-turn prussik knot (having six (6) loops 228), or a four-turn prussik knot (having eight (8) loops 228).

In the present embodiment, when in the insertion configuration C1, the portion of the snake member 8 that extends through the loops 228 of the locking mechanism 226 can be referred to as the "first snake portion" 8*a*, while the portions of the snake member 8 that extend away from the first snake portion 8*a* can be referred to as "snake tails," e.g., first and second snake tails 8*b*1, 8*b*2. Similarly, the portion of the actuation member 6*a* that defines the loops 228 of the locking mechanism 226 can be referred to as the "first actuation portion" 6*a*, while the portions of the actuation member 6 that extend away from the first actuation portion 6*a* can be referred to as "actuation tails", e.g., first and second actuation tails 6*b*. The first and second actuation tails 6*b* preferably extend side-by-side through the same proximal and distal penetrations 224*a,b* through the anchor body 4. The first and second actuation tails 6*b* can be coupled together in a manner defining a joined actuation tail 6*d*, such as via a bury splice, that extends proximally from a first joint location 6*c*1 (i.e., "splice insertion point" 6*c*1) to a second joint location 6*c*2 (i.e., "splice end" 6*c*2). In the present embodiment, the splice insertion point 6*c*1 is preferably located proximally of the proximal end 16 of the anchor body 4, as shown in FIG. 9B, and the splice end 6*c*2 can be at the free end 6*e* of the actuation member 6, as shown in FIG. 9A. Alternatively, the splice insertion point 6*c*1 of the present embodiment can be positioned with in the eyelet 12 of the anchor loop 14; and the splice end 6*c*2 can be spaced distally from the free end 6*e* of the actuation member 6. As the repair assembly 201 transitions to the approximated configuration C3, the second snake tail 8*b*2 pulls the joined actuation tail 6*d* through the loops 228 of the locking mechanism 226, as described in more detail below (and similar to the manner of the embodiment above).

The snake member 8 of the present embodiment preferably has a first diameter region 8*m* and a second, reduced diameter region 8*n* that extend oppositely from a transition location 8*o*. The transition location 8*o* and the reduced diameter region 8*n* are located along the second snake tail 8*b*2, particularly such that the reduced diameter region 8*n* extends from the transition location 8*o* to the free end 8*e*2 of the second snake tail 8*b*2. Accordingly, the reduced diameter region 8*n* can be characterized as a region of the second snake tail 8*b*2. In the illustrated embodiment, the first diameter region 8*m* extends from the transition location 8*o* to the free end 8*e*1 of the first snake tail 8*b*1. Alternatively, the first snake tail can also have a reduced diameter region extending to the free end 8*e*1 thereof. The difference in diameter of the first diameter region 8*m* and the reduced diameter region 8*n* can be provided by disposing material within the core space of the snake member 8 along the first diameter region 8*m* while the core space along the reduced diameter region 8*n* is devoid of material. Alternatively, the core space of the reduced diameter region 8*n* can also contain material therein but having a material thickness or diameter less than that in the core space of the first diameter region 8*m*. In one non-limiting example, the snake member 8 (including both the first and reduced diameter regions 8*m,n*) comprises #5 size ETHIBOND® suture, with the first diameter region 8*m* further comprising #2 size ETHIBOND® suture spliced within the axial core space thereof.

As the repair assembly 201 transitions from the insertion configuration C1 (FIG. 9B) to the anchored configuration C2 (FIG. 9C), the anchor body 4 is particularly configured to bunch-up such that its length decreases and its width increases, similar to the embodiment described above. In the present embodiment, the anchor body 4 can be actuated to transition to the anchored configuration C2 by pulling or otherwise tensioning the first and second snake tails 8*b*1, 8*b*2 in unison, which can optionally be achieved without also tensioning the actuation member 6. Additionally or alternatively, the anchor body 4 can be actuated by pulling or otherwise tensioning the actuation member 6 in unison with the first and second snake tails 8*b*1, 8*b*2, similar to the manner described above with reference to the soft anchor 2 shown in FIG. 2B.

Referring again to FIG. 9A, in the repair assembly 201 of the present embodiment, to initiate the formation of a shuttle loop 31 around the second anatomical structure 7, a proximal region of the actuation member 6 couples with a proximal region 8*i* of the second snake tail 8*b*2, such as via being spliced together. Accordingly, the coupled proximal region 8*i* of the second snake tail 8*b*2 can be referred to as the "proximal spliced region" 8*i* thereof. The proximal spliced region 8*i* of the second snake tail 8*b*2 is located along the reduced diameter region 8*n* thereof. It should be appreciated that the required splice distance 8*i* for the snake to pull the actuation tail through the assembly will be specific to the construction of the free end 6*e* of the actuation member 6 and the reduced snake diameter region 8*n* but will generally have a length in a range of about 10 mm to about 80.0 mm, more particularly about 40.0 mm to about 50.0 mm. To facilitate such spliced coupling, the assembly 201 can include a threading tool or "threader" 205, which can pierce the jacket of the second snake tail 8*e*2 at first and second penetrations 8*k*1, 8*k*2 and extends within the core space of the second snake tail 8*b*2 between the first and second penetrations 8*k*1, 8*k*2. The threader 205 extends outwardly from the second penetration 8*k*2 and includes a grasper 207, such as an eyelet 207, at the end thereof. The free end 6*e* of the joined actuation tail 6*d* can be threaded through the grasper 207, which can then be used to pull the free end 6*e* of the actuation member 6 into the core space of the second snake tail 8*b*2.

Figure 9E:
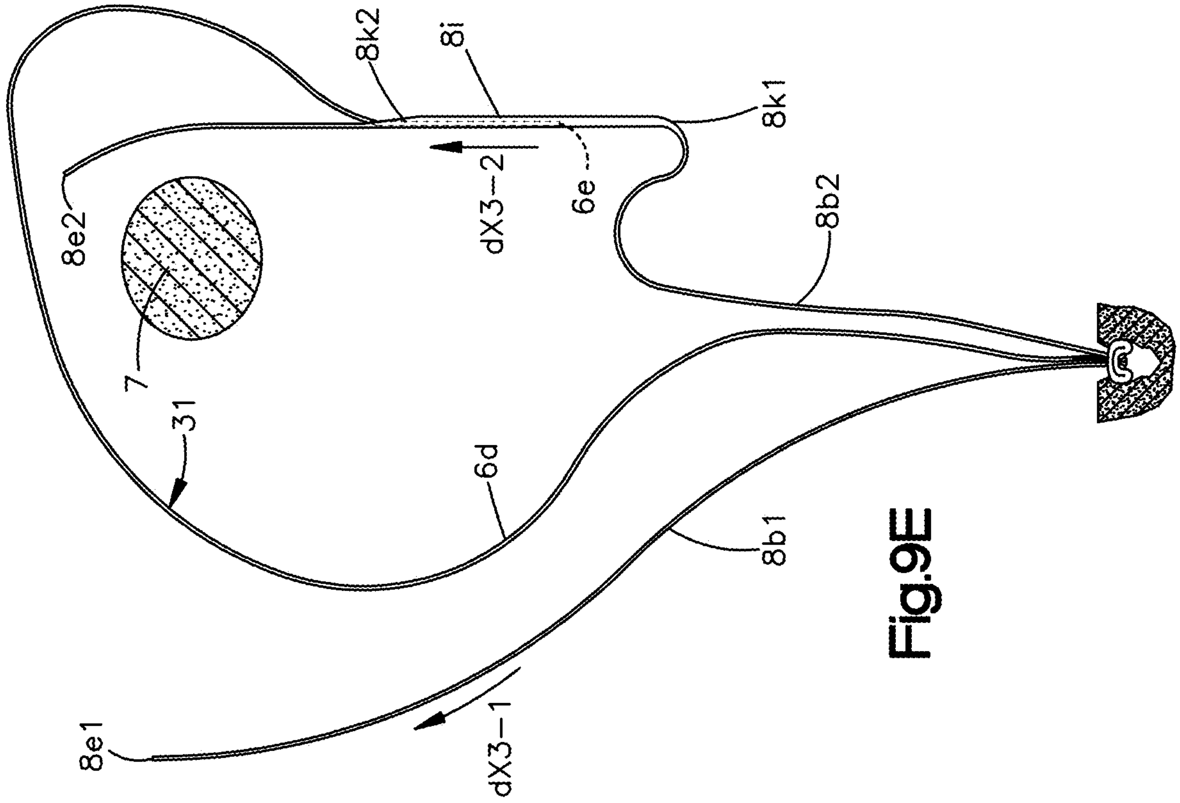
FIGS. 9D-9G are front plan views of the tissue repair assembly illustrated in FIG. 9A shown in various stages of a process for approximating tissue, according to an embodiment of the present disclosure.
Figure 9D:
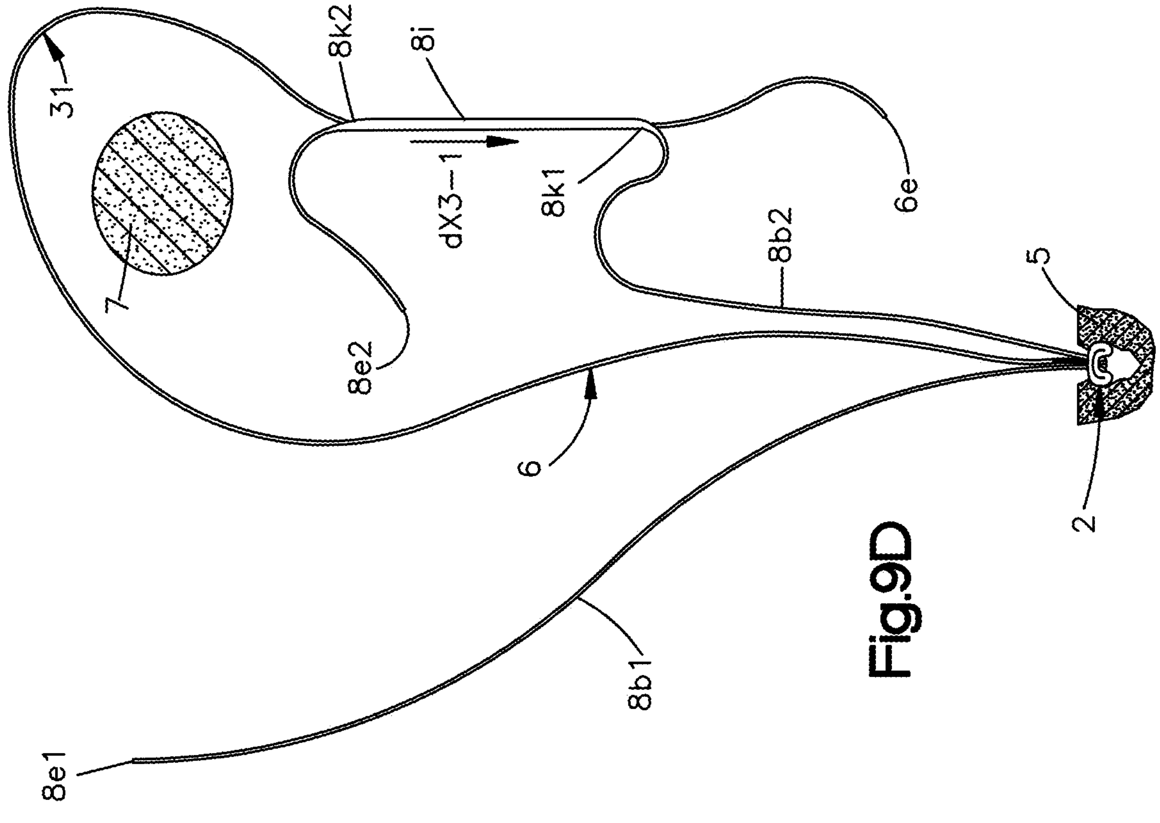

As shown in FIG. 9D, in a stage of forming the shuttle loop 31, the free end 6*e* of the actuation member 6 can be pulled through the core space of the second snake tail 8*b*2, from the second penetration 8*k*2 to the first penetration 8*k*1 in the first axial snake direction dX3-1, and can be pulled outwardly through, and distally beyond, the first penetration 8*k*1. As shown in FIG. 9E, in a subsequent stage of forming the approximation loop 32, the joined actuation tail 6*d* can be retracted along the second axial snake direction dX3-2 until the free end 6*e* of the actuation member 6 *us* pulled back inside the second snake tail 8*b*1 between the first and second penetrations 8*k*1, 8*k*2. This provides a smoother transition from the reduced diameter portion 8*n* to the spliced portion 8*i*. Additionally or alternatively, the portion of the joined actuation tail 6*d* that is shown in FIG. 9D as extending outwardly and distally from the first penetration 8*k*1 can be trimmed prior to retraction or as an alternative to retraction. It should be appreciated that the reduced diameter portion 8*n* of the second snake tail 8*b*2 preferably allows the diameter of the proximal spliced region 8*i* to be substantially equivalent to the diameter of the first region 8*m* of the snake member 8. This helps reduce impedance between the proximal spliced region 8*i* and the loops 228 of the locking mechanism 226 as the snake member 8 shuttles the proximal spliced region 8*i* through locking mechanism 226.

Figure 9F:
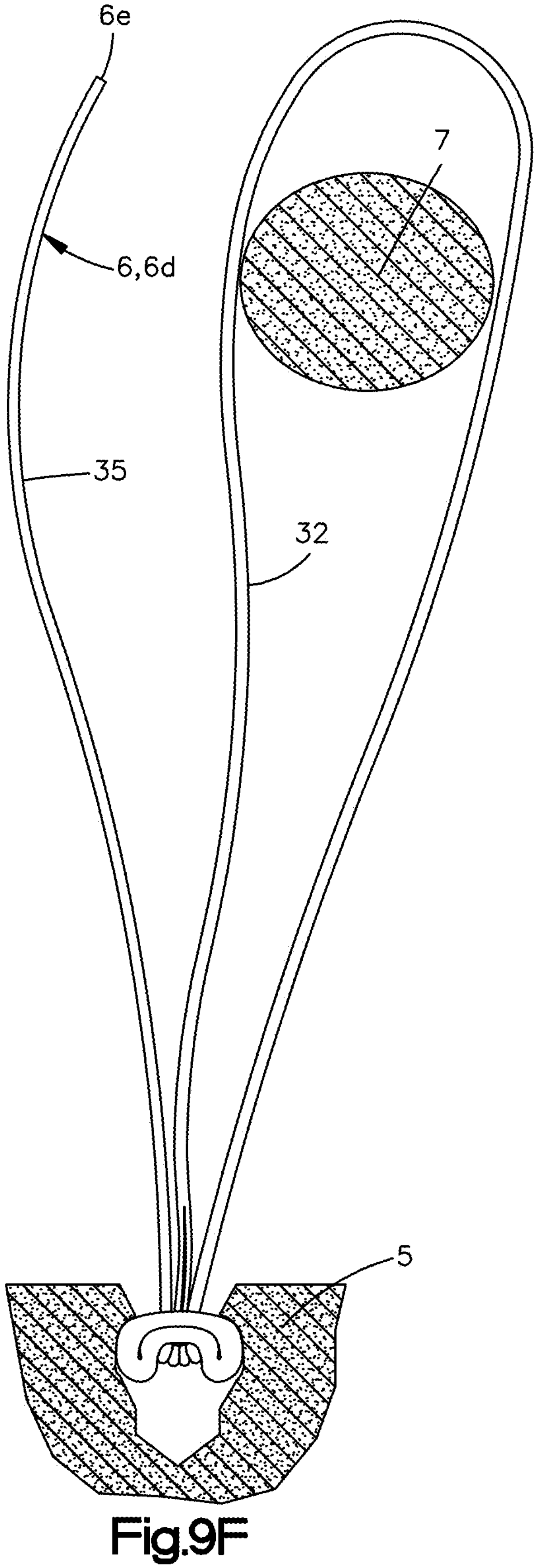
Figure 9G:
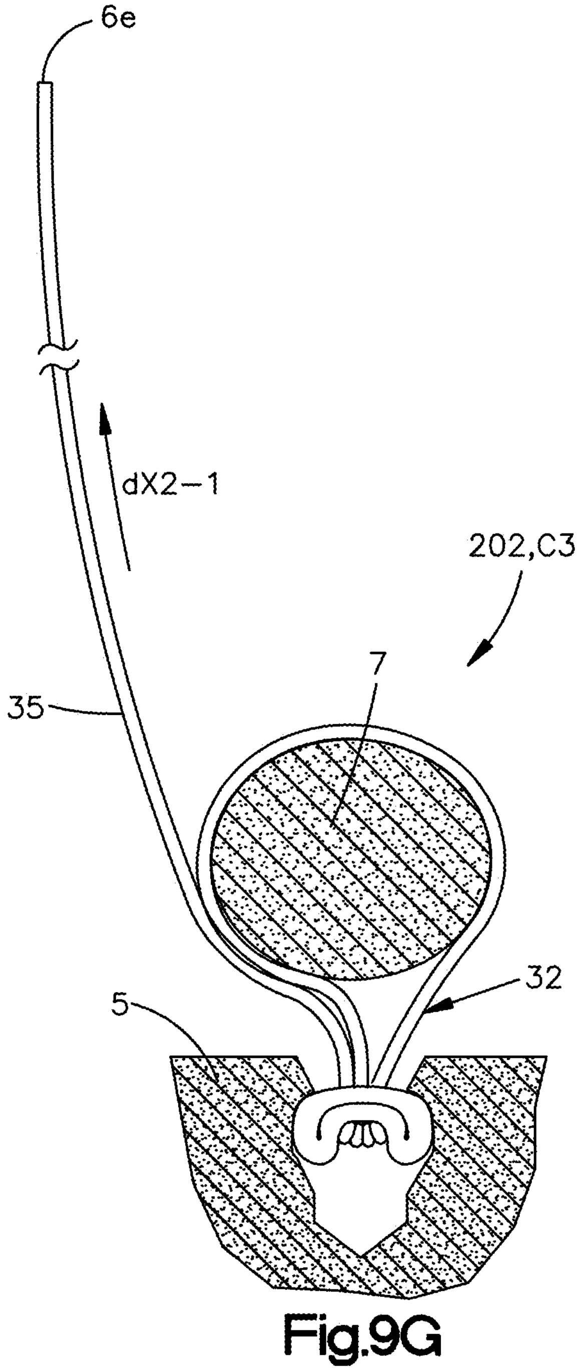

At the stage shown in FIG. 9E, the joined proximal regions of the joined actuation tail 6*d* and the second snake tail 8*b*2 provide a closed shuttle loop 31 around the second anatomical structure 7, at which stage the snake member 8 is ready to shuttle the joined actuation tail 6*d* into and through the locking mechanism 225. To do so, the surgeon pulls the first snake tail 8*b*1 in the first axial snake direction dX3-1, which in turn pulls the coupled second snake tail 8*b*2 and the joined actuation tail 6*d* toward, then into and through, and then away from the locking mechanism 226 along the first axial snake direction dX3-1, so that the actuation member 6 defines an approximation loop 32 around the second anatomical structure 7 and also defines an actuation post 35, as shown in FIG. 9F. At this stage, the snake member 8 can be decoupled from the actuation member 6, or can optionally remain coupled thereto. The actuation post 35 can be in the first axial actuation direction dX2-1 to reduce the circumference of the approximation loop 32 and approximate the second anatomical structure 7 with respect to the first anatomical structure, as shown in FIG. 9G. When the second anatomical structure 7 is satisfactorily approximated with respect to the first anatomical structure 5, the actuation post 35 can be trimmed to remove excess material at the treatment site. It should be appreciated that the locking mechanism 226 substantially locks the approximation loop 32 in the fully approximated configuration, thereby obviating the need to further tie-off the post 35. Optionally, the post 35 can be tied-off to provide a secondary locking structure to the approximation loop 32. It should be appreciated that numerous additional and/or alternative steps can be performed to facilitate the foregoing exemplary technique for approximating tissue.

It should be appreciated that the repair assembly 201 shown in FIGS. 9A-9G possesses many of the same advantages as those of the repair assembly 2 described above (see the foregoing discussion with reference to FIGS. 6M and 2B). For example, when in the anchored configuration C2 (see FIG. 9C), the anchor body 4 has been observed to present a broad proximal face, which combined with the increased maximum anchor width, enhances the anchor affixation within the bone. Additionally, the proximal portion 4*a* of the anchor body 4 provides a barrier-like formation that mechanically interferes with and thus resists migration of the locking mechanism 226 away from the anchor body 4 (such as during anchoring and/or tissue approximation) and thus also resists tenting affects and unwanted laxity in the approximation loop 32 that can result from such migration. Furthermore, because the locking mechanism 226 of the present embodiment is located distal of the distal end 18 of the anchor body 4 when in the insertion configuration C1, the distal portion 4*b* of the anchor body 4 provides yet an additional barrier-like formation impeding proximal migration of the locking mechanism 226. Moreover, a particular advantage of the present embodiment is that the spliced proximal regions of the second snake tail 8*b*2 and the actuation member 6 (i.e., along spliced portion 8*i* of the second snake tail 8*b*2) enhances smooth shuttling of the proximal region of the actuation member 6 into and through the locking mechanism 226 when forming the approximation loop 32.

Referring now to FIGS. 10A-10I, another embodiment of a tissue repair assembly 301 for anatomical fixation (e.g., anatomical approximation) will now be described. The repair assembly 301 of the present embodiment, and the methods of using it to repair tissue, can be generally similar to those of the repair assemblies 1, 201 described above. For example, referring now to FIG. 10A, the repair assembly 301 of the present embodiment includes an anchor body 304, and also includes a cannulated actuation member 306 and a snake member 8 coupled to the anchor body 304 and extending therefrom when in an insertion configuration C1. Moreover, the anchor body 304 and portions of the actuation member 306 and snake member 8 coupled thereto define a soft anchor 302 of the repair assembly 301. For the sake of brevity, the following discussion focuses mainly on differences employed in the repair assembly 301 relative to the repair assemblies 1, 201 described above. In the following discussion, features having similar design and function to those described above can employ the same reference numbers.

Figure 10A:
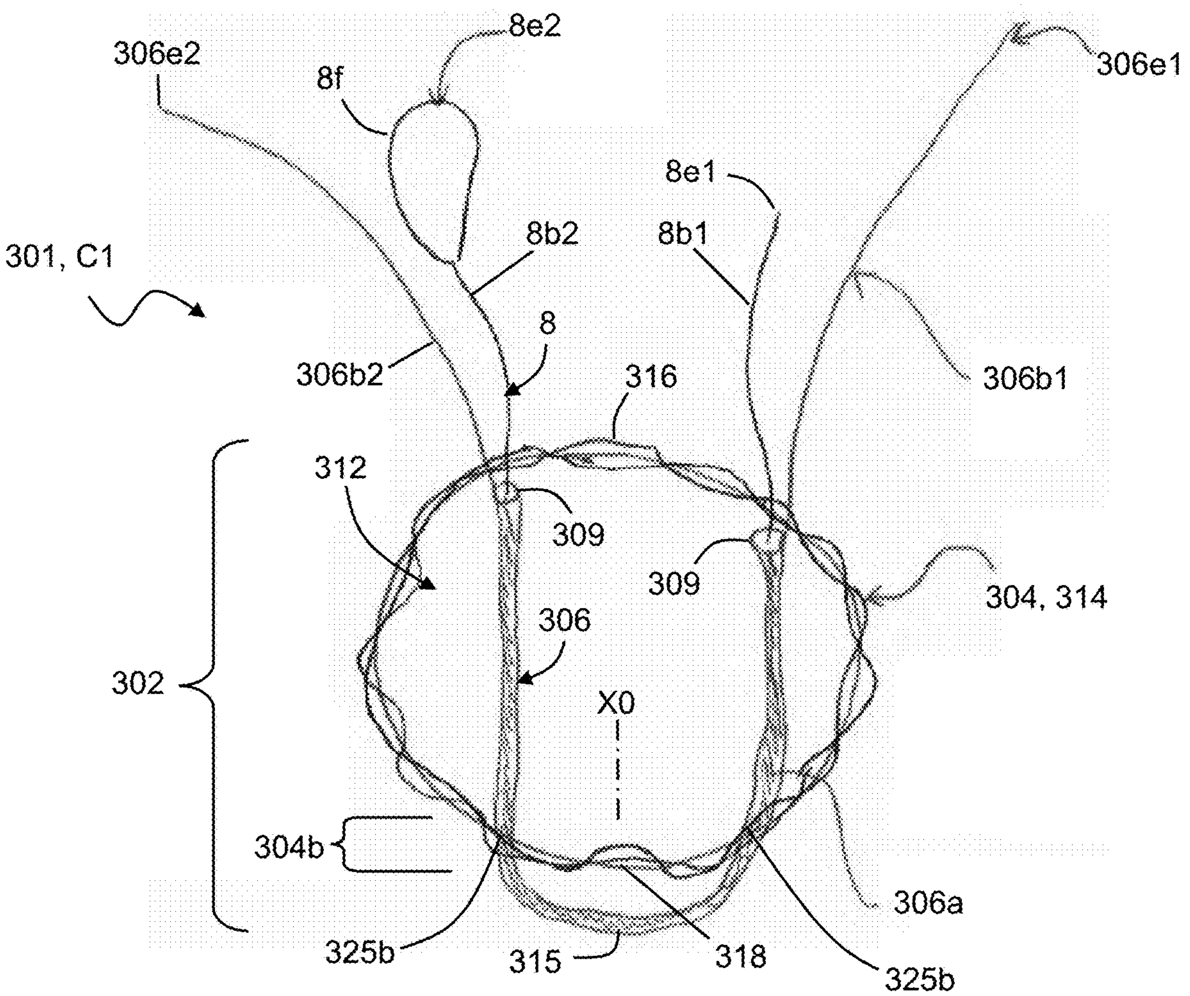
FIG. 10A is a front plan view of a tissue repair assembly having a cannulated actuation member, according to another embodiment of the present disclosure.

With continued reference to FIG. 10A, the anchor body 304 is arranged into an anchor loop 314 and is constructed of a continuous braid of suture material(s). In this regard, the anchor body 304 can be configured as more fully described in U.S. Pat. No. 9,284,668, issued Mar. 15, 2016, in the name of Johnson, et al. ("the '320 Reference"), the entire disclosure of which is hereby incorporated by reference herein. The actuation member 306 is constructed of textile suture material and has a first portion 306*a* that defines a cannulation 307 and a pair of actuation tails 306*b* extending oppositely away from the first portion 306*a*. Accordingly, the first portion 306*a* can be characterized as a "cannula" 306*a*. The actuation tails 306*b* can each have a flat or "tape"-like cross-geometry when in a neutral configuration, such as the tape-like geometries described more fully in the '320 Reference. In the insertion configuration C1, the snake member 8 extends through the cannulation 307 of the cannula 306*a*, with first and second snake tails 8*b*1, 8*b*2 extending outwardly from the openings 309 to first and second snake ends 8*e*1, 8*e*2, respectively. The second snake tail 8*b*2 defines a snake loop 8*f* at the second snake tail end 8*e*2, which snake loop 8*f* can be configured similar to the snake loop 8*f* described above with reference to FIGS. 1A and 6A.

Figure 10B:
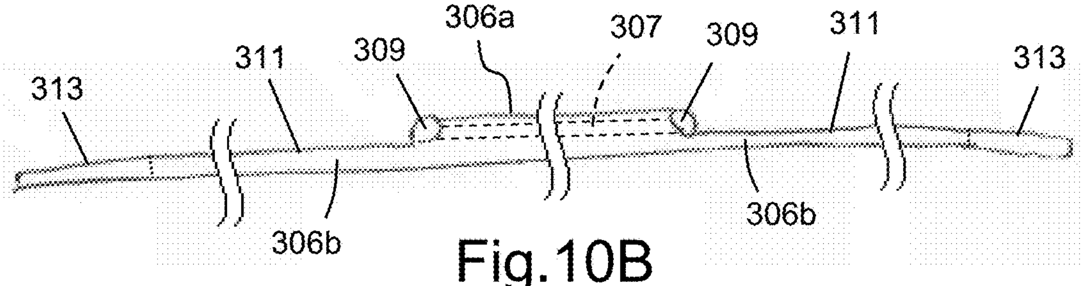
FIG. 10B is a front plan view of the cannulated actuation member of the tissue repair assembly illustrated in FIG. 10A, shown in a neutral configuration.
Figure 10C:
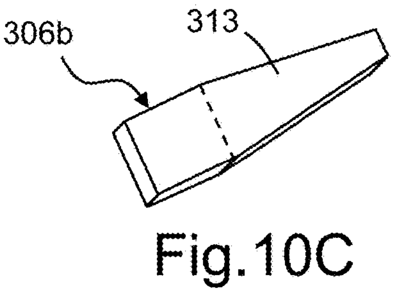
FIGS. 10C-10D are enlarged perspective, partial sectional end views of alternative configurations of end portions of the cannulated actuation member illustrated in FIG. 10B, according to embodiments of the present disclosure.
Figure 10D:
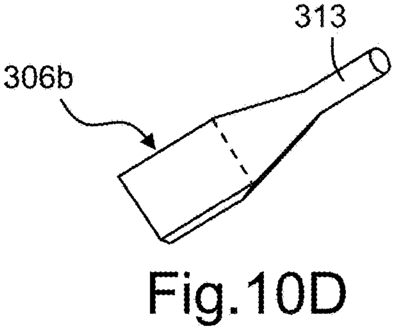

With reference to FIG. 10B, the actuation member 306 is shown in isolation in a neutral configuration. The actuation tails 306*b* can each have a first tail portion 311 adjacent the cannula 306*a* and an end tail portion 313 that is remote from the cannula 306*a* and defines a free end 306*e* of the respective actuation tail 306*b*. One or both of the end tail portions 313 can have geometries that deviate from those of the first tail portions 311 and facilitate threading one or both of the free ends 306*e* through a coupling structure, such as a snake loop 8*f*. For example, one or both of the end tail portions 313 can have a rounded cross-sectional geometry, as shown in FIG. 10C, or a tapered flat geometry, as shown in FIG. 10D. The cannula 306*a* defines first and second openings 309*a,b* at the ends thereof and in communication with the cannulation 307.

Referring again to FIG. 10A, the cannula 306 is coupled to a distal portion 304*b* of the anchor body 304. The cannulation 306 is bent so that a distal apex 315 of the cannulation 306*a* is located distally of a distal end 318 of the anchor body 304. Thus, in the present embodiment, the distal apex 315 of the cannulation 306 a defines a distal end of the soft anchor 302. Portions of the cannula 306*a* can extend through respective penetrations 325*b* through the distal portion 304*b* of the anchor body 304 and extend proximally within the eyelet 312 of the anchor loop 314 toward the proximal end 316 of the anchor body 304. As shown, the portions of the cannula 306*a* can extend through the anchor eyelet 312 substantially parallel with each other, although in other embodiments the portions of the cannula 306*a* can extend through the anchor eyelet 312 in non-parallel fashion. In the illustrated embodiment, the openings 309*a,b* at the ends of the cannulation 306*a* are positioned within the anchor eyelet 312 when in the insertion configuration C1, although in other embodiments, one or both of the openings 309*a,b* can be positioned proximally from the anchor body 304 when in the insertion configuration C1.

Figure 10E:
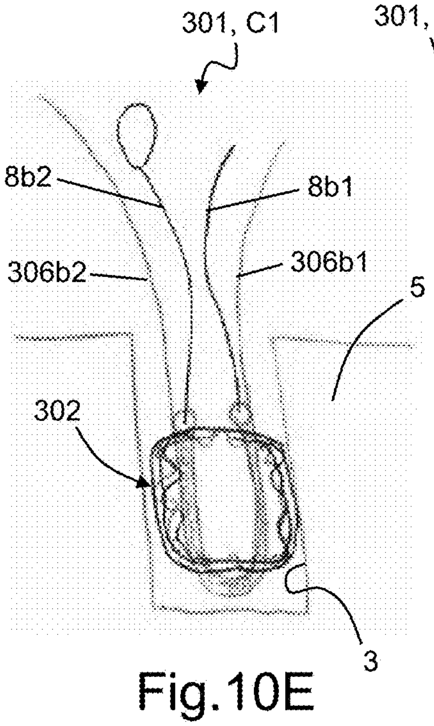
FIGS. 10E-10I are front plan views of the tissue repair assembly illustrated in FIG. 10A, shown in various stages of a process for approximating tissue, according to an embodiment of the present disclosure.
Figure 10F:
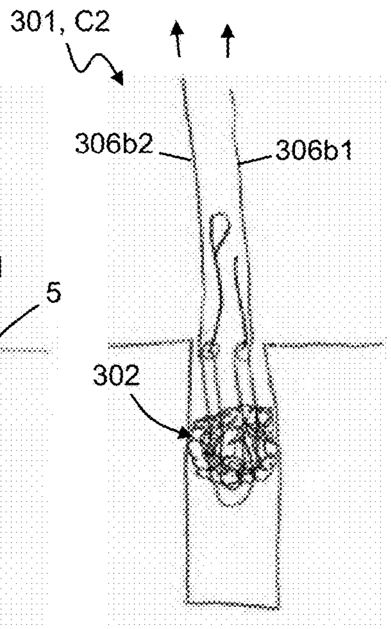
Figure 10G:
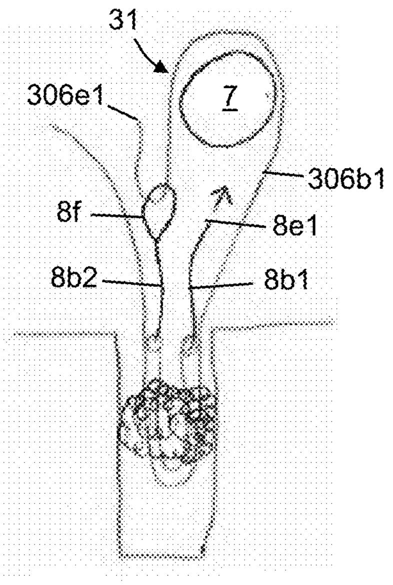
Figure 10H:
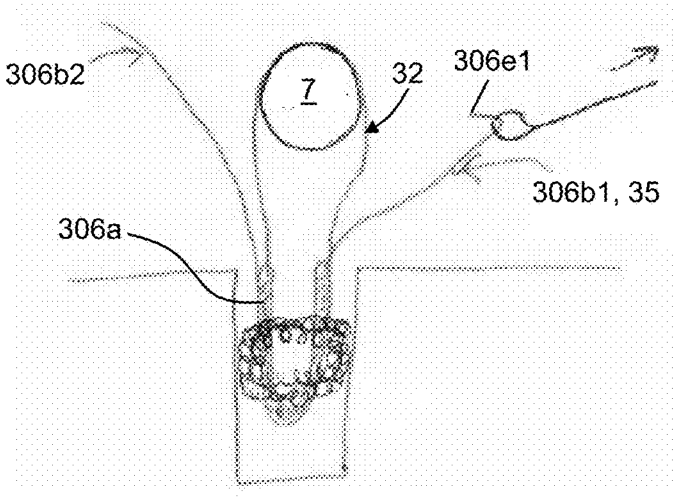
Figure 10I:
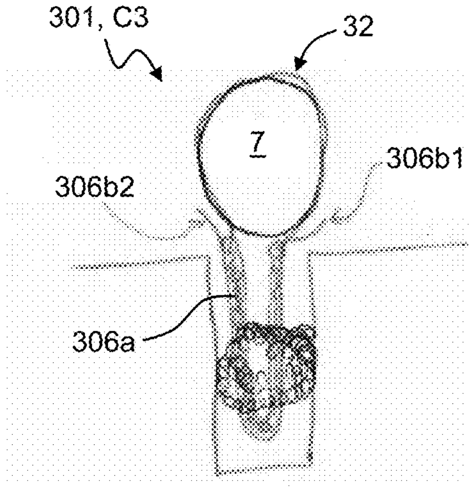

With reference to FIG. 10E-10I, an exemplary method will now be described of using the repair assembly 301 described above with reference to FIGS. 10A-10D to approximate tissue. As shown in FIG. 10E, the soft anchor 302 of the repair assembly 301 is inserted, while in the insertion configuration C1, to the target location 3 of a first anatomical structure 5, such as a pre-drilled hole 3 in bone 5. At this stage, the actuation tails 306*b*1, 306*b*2 and the snake tails 8*b*1, 8*b*2 extend generally proximally away from the target location 3. As shown in FIG. 10F, with the soft anchor 302 inserted at the target location 3, the surgeon can actuate the anchor 302 into the anchored configuration C2 by tensioning the actuation tails 306*b*1, 306*b*2 in unison. As shown in FIG. 10G, with the soft anchor 2 set, the surgeon can pass the free end 6*e*1 of the first actuation tail 306*b*1 around the second anatomical structure 7. Additionally, the surgeon threads the free end 6*e*1 of the first actuation tail 306*b*1 through the snake loop 8*f* at the end 8*e*2 of the second snake tail 8*b*2, thereby coupling the proximal regions of the first actuation tail 306*b*1 and the second snake tail 8*b*2 in a manner forming a shuttle loop 31 around the second anatomical structure 7. With the shuttle loop 31 formed, the surgeon can pull the free end 8*e*1 of the first snake tail 8*b*1 to shuttle the free end 306*e*1 of the first actuation tail 306*b*1 into and through the cannula 306*a*, thereby causing the actuation member 306 to form an approximation loop 32 around the second anatomical structure 7, as shown in FIG. 10H. With the approximation loop 32 formed, and with the free end 306*e*1 of the first actuation member 306*b*1 and the second end 8*e*2 of the second snake tail 8*b*2 exterior of the cannula 306*a*, the snake member 8 can be decoupled from the first actuation tail 306*b*1. At this stage (FIG. 10H), the portion of the first actuation tail 306*b*1 extending outwardly from the first opening 309*a* of the cannula 306*a* forms the post 35, and is subsequently tensioned to approximate the second anatomical structure 7 with respect to the first anatomical structure 5. Referring now to FIG. 101, the repair assembly 301 is shown in the approximated configuration C3, with the first and second actuation tails 306*b*1, 306*b*2 having been trimmed to remove excess material at the treatment site.

It should be appreciated that the respective configurations of the first actuation tail 306*b*1 and the cannula 306*a* (e.g., their size and shape) collectively form a locking mechanism, which, in the approximated configuration C3, retains the position of the first actuation tail 306*b*1 within the cannulation 307, thereby affixing the position of the approximated second anatomical structure 7 relative to the anchor 302 (and thus also to the first anatomical structure 5). In particular, during tissue approximation, the tension applied to the first actuation tail 306*b*1 is transmitted to the cannula 306*a*, which, due to the braiding configuration in which the cannula 306*a* is constructed, causes the cannula 306*a* to stretch lengthwise and constrict diameter-wise. This tension-responsive elongation-constriction behavior provides one-way locking against the portion of the first actuation tail 306*b*1 within the cannulation 307. Because tension along the first actuation tail 306*b*1 and the cannulation 306*a* is maintained after the second anatomical structure is satisfactorily approximated, the cannula 306*a* locks against the first actuation tail 306*b*1 with sufficient force to retain the approximated position of the second anatomical structure with respect to the first anatomical structure 5.

Figures 11A, 11B, 11C:
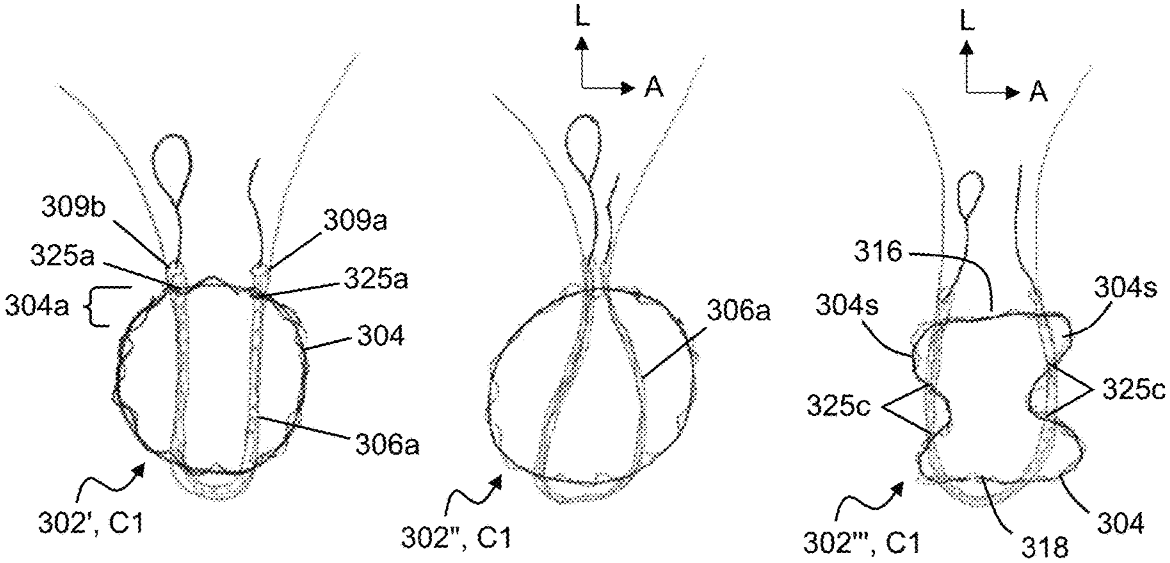
FIGS. 11A-11C are front plan views of additional tissue repair assemblies similar to the tissue repair assembly illustrated in FIG. 10A, showing alternative arrangements of the anchor body and/or the cannulated actuation member, according to additional embodiments of the present disclosure.

It should be appreciated that the soft anchor 302 discussed above with reference to FIGS. 10A-10I can have alternate arrangements and adaptations, some non-limiting examples of which are shown in FIGS. 11A-11C, each showing their soft anchor in the insertion configuration C1.

As shown in FIG. 11A, in another embodiment of the soft anchor 302', the cannula 306*a* can be configured so that the openings 309*a,b* thereof are located proximally from the proximal end 16 of the anchor body 304. In this embodiment, end portions of the cannula 306 can extend proximally through respective penetrations 325*a* through a proximal portion 304*a* of the anchor body 304. As shown in FIG. 11B, in another embodiment of the soft anchor 302'', the cannula 306*a* can be configured so that proximal portions thereof converge toward each other, such that a lateral spacing between the openings 309*a,b* is less than that in other embodiments of the soft anchor 302. As shown in FIG. 11C, in another embodiment of the soft anchor 302''', the anchor body 304 can be arranged into an hourglass-like shape. In this embodiment, the cannula 306*a* can extend through a pair of additional penetrations 325*c* through the anchor body 304 at each lateral side 304*s* thereof. Additionally, the proximal and distal ends 316, 318 of the anchor body 304 can be substantially straight in this embodiment.

It should be appreciated that numerous other variations and adaptations to the soft anchor 302 design are within the scope of the present disclosure.

Figure 12:
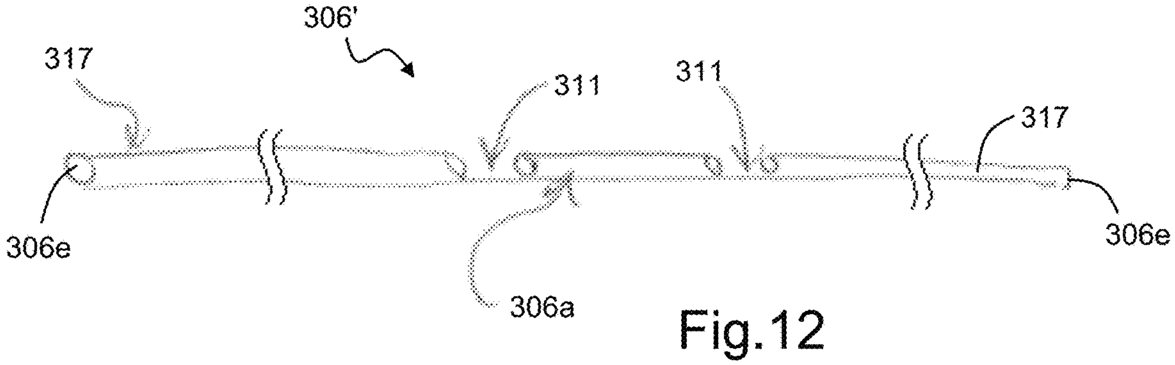
FIG. 12 is a front plan view of an alternative design of a cannulated actuation member for a tissue repair assembly, shown in a neutral configuration, according to another embodiment of the present disclosure.

For example, referring now to FIG. 12, in an additional embodiment, a soft anchor can employ a cannulated actuation member 306' having a central cannula 306*a* and a pair of actuation tails 306*b* extending oppositely therefrom. The illustrated example of the cannulated actuation member 306' is shown in a neutral configuration, and can be arranged with respect to the anchor bodies 4, 204, 304 described above in various shapes, including those shown above in FIGS. 10A and 11A-11C. The central cannula 306*a* defines a cannulation 307 extending therethrough. In the present embodiment, each actuation tail 306*b* includes a tape portion 311 extending outwardly from the central cannula 306 and an end portion 317 having a circular cross-section that extends from the tape portion 311 to a free end 306*e* of the actuation tail 306*b*. The circular cross-sections of the end portions 317 are configured to lock within the central cannula 306*a* when in the approximated configuration.

Figure 13A:
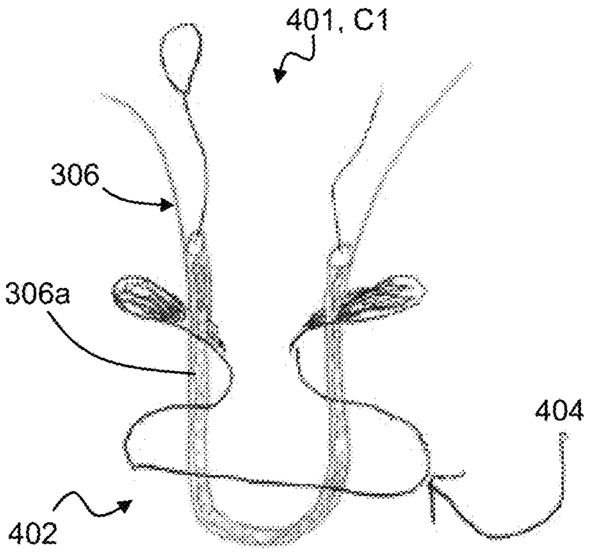
FIG. 13A is a front plan view of a tissue repair assembly having a cannulated actuation member and an alternative anchor body, according to another embodiment of the present disclosure.
Figure 13B:
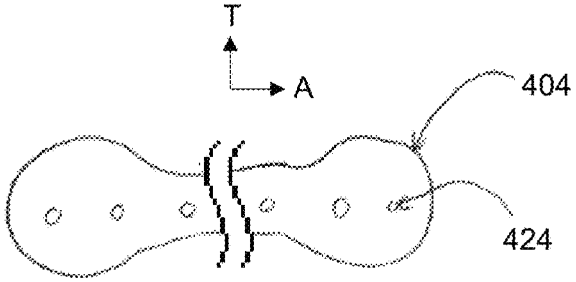
FIG. 13B is a top plan view of the anchor body illustrated in FIG. 13A, shown in a neutral configuration.

Referring now to FIGS. 13A-13B, in yet another embodiment, a tissue repair assembly 401 has a soft anchor 402 that can employ an alternative type anchor body 404 with a cannulated actuation member 306. In this embodiment, the anchor body 404 need not be arranged in a loop, and can instead be an elongate body, which can optionally be constructed of a felt material. The anchor body 404 can have a generally flat geometry when in a neutral configuration, which configuration is shown in FIG. 13B. The anchor body 404 can define apertures 424 that are configured to receive associated portions of the cannula 306*a* of the actuation member 306. The anchor body 404 can have a dogbone-like base shape when in the neutral configuration, although it should be appreciated that various other base shapes can be employed to achieve various anchor designs and shapes when in the insertion configuration C1. In the illustrated embodiment, the anchor body 404 defines six (6) apertures 424, which can facilitate the anchor body 404 having a shape similar to the bottom half of an hourglass, as shown in FIG. 13A, when coupled with the cannula 306*a* and in the insertion configuration C1. It should be appreciated that the anchor body 404 can define fewer or more than six (6) apertures, which can facilitate the anchor body 404 having various other arrangements and shapes when coupled to the cannulated actuation member 306. It should also be appreciated that the soft anchor 402 is actuated into an anchored configuration and an approximated configuration similar to the manner described above with reference to other embodiments.

Figure 14:
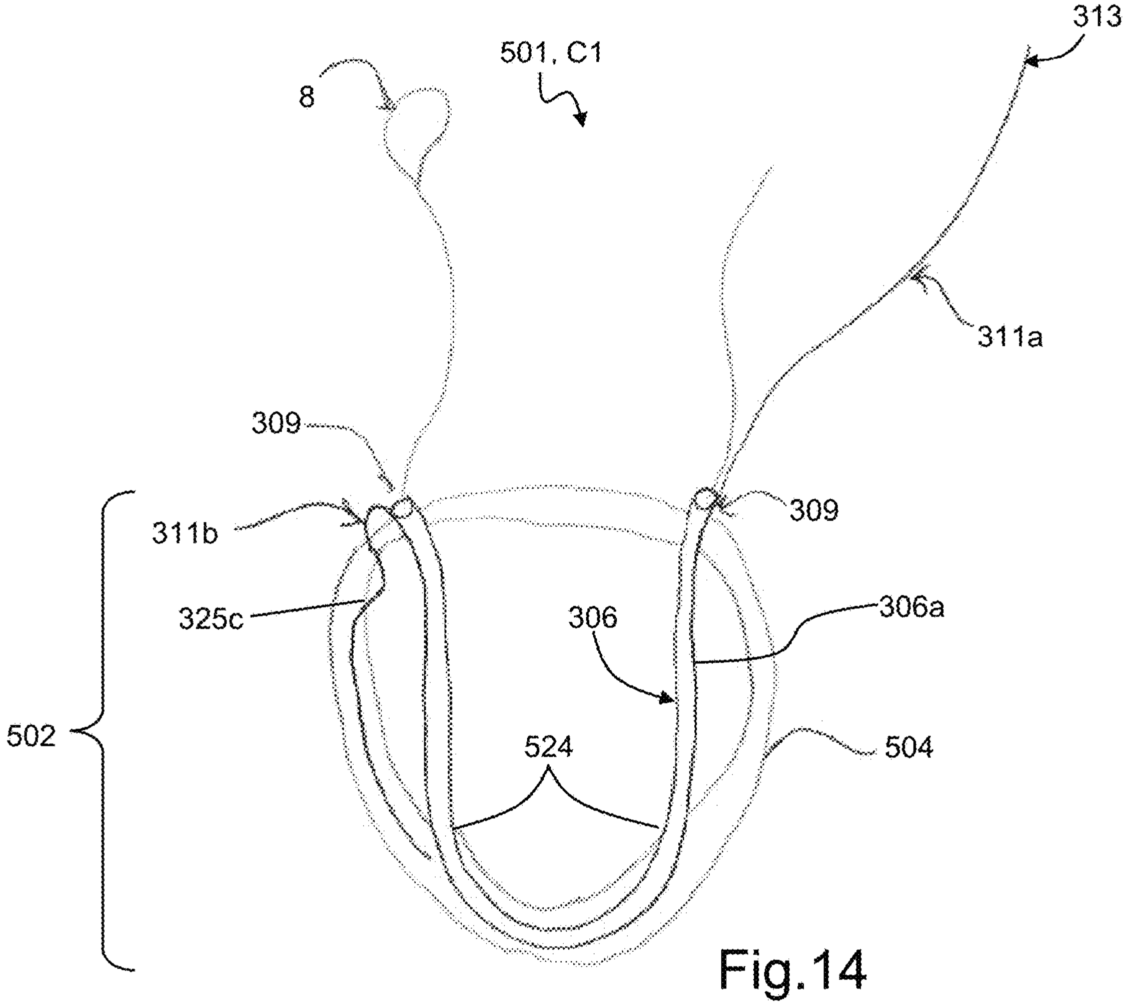
FIG. 14 is a front plan view of a tissue repair assembly having a cannulated actuation member, wherein a tail of the cannulated actuation member is spliced with the anchor body, according to another embodiment of the present disclosure.

Referring now to FIG. 14, an exemplary embodiment of a tissue repair assembly 501 is shown in which one of the actuation member tails 311*b* is anchored to the anchor body 504 when in the insertion configuration C1. The anchor body 504 can be similar to the anchor bodies 4, 304 described above. Moreover, the anchor body 504 and portions of the actuation member 306 and snake member 8 coupled thereto define a soft anchor 502 of the repair assembly 501. As shown, the anchor body 504 can be arranged into a closed anchor loop 514 having an elliptical shape. The repair assembly 501 can have a cannulated actuation member 306 having tape-like first and second actuation tails 311*a*, 311*b* extending outwardly from opposite ends of a cannula 306*a*, similar to the cannulated actuation member 306 described above with reference to FIGS. 10A-10I. When in the insertion configuration C1, a snake member 8 extends through, and outwardly from the cannula 306*a*, and is configured to shuttle the first actuation tail 311*a* into and through the cannulation 306*a* for forming an approximation loop 32 around a second anatomical structure 7, as described above in relation to other embodiments herein. Also similar to embodiments described above, the geometries and constructions of the first actuation tail 311*a* and the cannula 306*a* cooperatively form a one-way locking mechanism when the first actuation tail 311*a* extends within the cannulation 306*a* and is tensioned to approximate tissue.

In the present embodiment, a distal bent portion of the cannula 306*a* extends through laterally opposed penetrations 524 through the jacket 515 of the anchor body 504 and into an interior passage therein, which interior passage can include the axial core space of the anchor body 504. Additionally, the second actuation tail 311*b* of the present embodiment doubles back and extends through the jacket 515 and into the axial core space 504 of the anchor body 504 and is affixed therein. For example, the second actuation tail 311*b* can be stitched into and along the braid of the jacket 515. The stitching of the second actuation tail 311*b* along the braid of jacket 515 may be optionally augmented such as via a locking stitch. In this manner, when tension is applied to the first actuation tail 311*a* during tissue approximation, at least a portion of that tension is transmitted through the cannula 306*a* and the second actuation tail 311*b* to the portion of the anchor body 504 affixed thereto, which increases the locking force applied by the cannula 306*a* on the first actuation tail 311*a*. Additionally, the affixation of the second actuation tail 311*b* to the anchor body 504 can further secure the locking mechanism to the anchor body 504 and thus reduce the chances of the locking mechanism migrating from the anchor body 504 during or after tissue approximation. It should be appreciated that various modifications and adaptations can be applied to the repair assembly 501 of the present embodiment, including many of those from other embodiments described herein.

Referring now to FIGS. 15A-15E, another embodiment of a tissue repair assembly 601 for anatomical fixation (e.g., anatomical approximation) will now be described. The repair assembly 601 includes an anchor body 604 for affixing to a first anatomical structure 5, an actuation member 611 for forming an approximation loop that interconnects the anchor body 604 to a second anatomical structure 7, and a locking mechanism 626 for locking the approximation loop in place with respect to the anchor body 604 after the second anatomical structure is satisfactorily approximated with respect to the first anatomical structure. The distal portion of the repair assembly 601, particularly the portion along the anchor body 604, can be characterized as a soft anchor 602. The repair assembly 601 of the present embodiment, and the methods of using it to repair tissue, can be generally similar to those of repair assemblies 1, 201, 301, 501 described above.

Figure 15A:
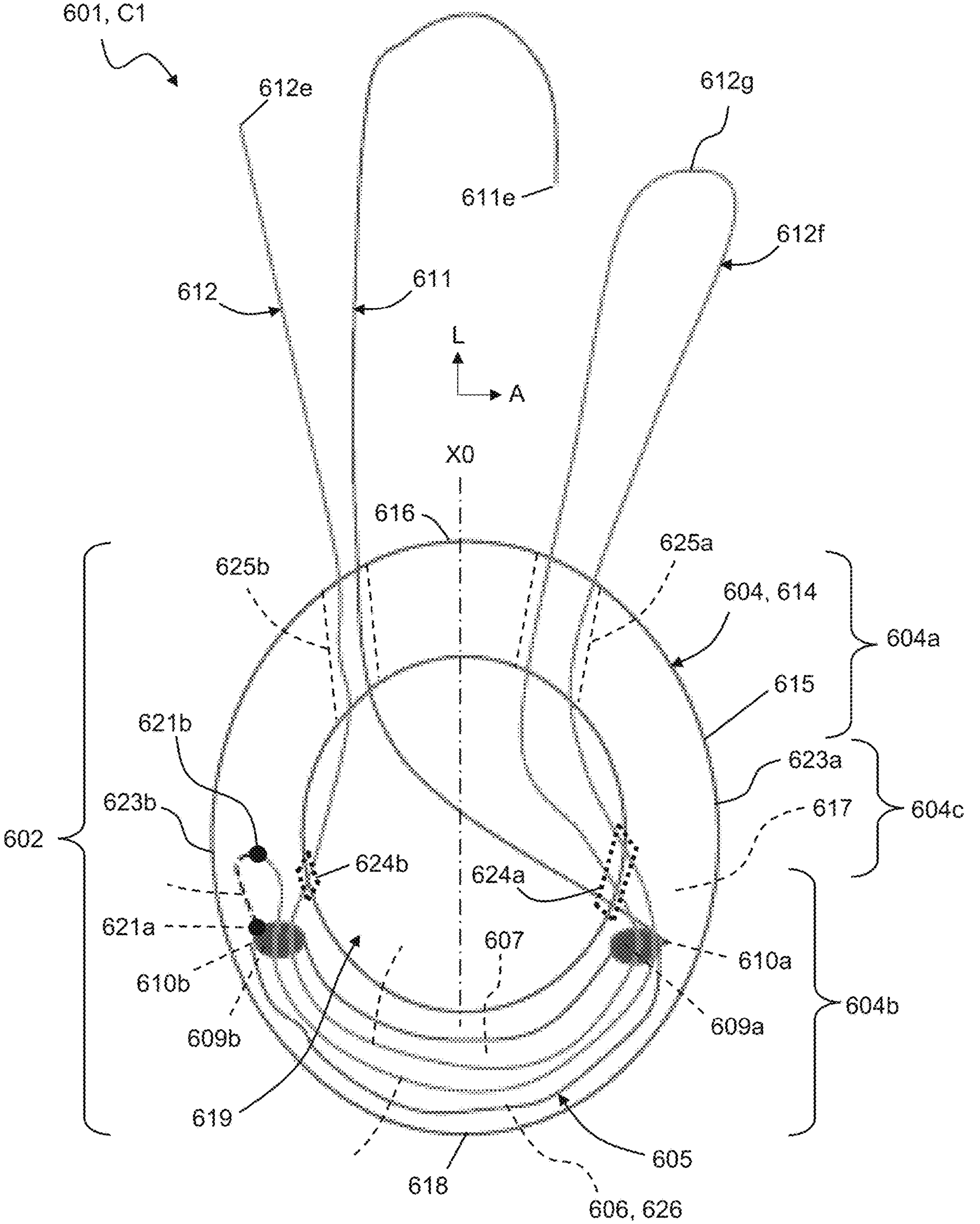
FIG. 15A is a front plan view of a tissue repair assembly having a cannulated actuation member partially disposed in an axial core space of an anchor body, according to another embodiment of the present disclosure.

For example, referring now to FIG. 15A, the repair assembly 601 of the present embodiment is shown in the insertion configuration C1, in which the anchor body 604 is preferably arranged into a closed anchor loop 614 having an elliptical shape. The anchor loop 614 defines a central anchor eyelet 619. The anchor body 604 can be similar to the anchor bodies 4, 204 described above with reference to FIGS. 1-6N and FIGS. 9A-9G, respectively. Accordingly, the anchor body 604 can have a textile jacket 615 surrounding (and defining) an axial core space 617. The repair assembly 601 includes a cannulated actuation member 605, which can be similar to the cannulated actuation members 306 described above with reference to FIGS. 10A-11C, 13A, and 14. The actuation member 605 includes a cannula 606, which is coupled to the anchor body 604 and defines the locking mechanism 626. The cannula 606 defines a cannulation 607 extending between first and second openings 609*a,b* at opposite ends 610*a,b* of the cannula 606. The cannula 606 is coupled to a distal portion 604*b* of the anchor body 604 within the axial core space 617 thereof. The distal portion 604*b* of the anchor body 604 includes the distal end 618 thereof and is longitudinally opposite a proximal portion 604*a* of the anchor body, which includes the proximal end 616 thereof. The anchor body 604 can also define an intermediate portion 604*c* longitudinally between the proximal and distal portions 604*a,b*. Preferably, the cannula 606 is laterally centered in the distal portion 604*b* of the anchor body 604, i.e., such that a lateral midpoint of the cannula 606 intersects the insertion axis X0 of the soft anchor 602, which axis X0 in turn intersects the distal end 618 of the anchor body 604. In this manner, the first opening 609*a* is positioned on a first lateral side 623*a* of the anchor body 604, while the second opening 609*b* is positioned on a second lateral side 623*b* of the anchor body 623*b* opposite the first lateral side 623*a*. For purposes of the following discussion, the first and second lateral sides 623*a,b* of the anchor body 604 represent the entire respective portions of the anchor body 604 on opposite sides of the insertion axis X0.

The actuation member 605 of the present embodiment includes an actuation tail 611 and a snake tail 612 that extend from the opposite ends of the cannula 606 to an actuation tail end 611*e* and a snake tail end 612*e*, respectively. The actuation tail 611 and the snake tail 612 can each have a respective tape-like cross-sectional geometry, circular cross-sectional geometry, or a combination thereof (e.g., one or both of the actuation tail 611 and the snake tail 612 can have one or more axial portions having a tape-like cross-sectional geometry and one or more axial portions having a circular cross-sectional geometry). In the present embodiment, the actuation member 605 is a monolithic structure, i.e., the cannula 606, the actuation tail 611, and the snake tail 612 are each separate portions of the monolithic structure that forms the actuation member 605.

The actuation tail 611 extends from the first end 610*a* of the cannula 606 and exits the anchor body 604 through a first distal penetration 624*a* through the jacket 615 on the first lateral side 623*a* of the anchor body 604. From the first distal penetration 624*a*, the actuation tail 611 extends along and/or through the anchor eyelet 619, crosses the insertion axis X0, and extends proximally through a second proximal penetration 625*b* through the proximal portion 604*a* of anchor body 604 at the second side 623*b* thereof.

The snake tail 612 is routed with respect to the anchor body 604 and the cannula 606 as follows. The snake tail 612 extends from the second end 610*b* of the cannulation 606 and extends through a first snake penetration 621*a* through the jacket 615 to an exterior of the anchor body 604. The snake tail 612 is routed back inside the anchor body 604 through a second snake penetration 621*b* through the jacket 615. As depicted in FIG. 15A, the first and second snake penetrations 621*a,b* are located on a rear face of the anchor body 604. From the second snake penetration 621*b*, the snake tail 612 is routed through the cannulation 607, from the second opening 609*b* to the first opening 609*a* thereof, and out of the cannulation 607 and, in turn, out of the anchor body 604 through the first distal penetration 624*a*. From the first distal penetration 624*a*, the snake tail 612 extends along and/or through the anchor eyelet 619 and extends proximally through a first proximal penetration 625*a* through the proximal portion 604*a* of anchor body 604 at the first lateral side 623*b* thereof. From the first proximal penetration 625*a*, the snake tail 612 extends generally proximally away from the anchor body 604 and is doubled back toward the anchor body 604 via a proximal bend 612*g* in the snake tail 612, from which bend 612*g* the snake tail 612 extends generally distally back through the first proximal penetration 625*a* of the anchor body 604. In this manner, the doubled portion of the snake tail 612 extending proximally from the first proximal penetration 625*a* to the bend 612*g* defines an elongated snake loop 612*f* for coupling with the actuation tail 611, which will be described in more detail below. The doubled back portion of the snake tail 612 extends distally from the first proximal penetration 625*a* and through and/or along the anchor eyelet 619, and back into the distal portion of the anchor body 604*b* through the first distal penetration 624*a*. From the first distal penetration 624*a*, the snake tail 612 extends back through the cannulation 607, in this instance from the first opening 609*a* to the second opening 609*b* and out therefrom. From the second opening 609*b* of the cannula 606, the snake tail 612 extends back out of the anchor body 604 through a second distal penetration 624*b* on the second lateral side 623*b* of the anchor body 604. From the second distal penetration 624*b*, the snake tail 612 extends through and/or along the anchor eyelet 619 and proximally through the second proximal penetration 625*b* of the anchor body 604 and proximally therefrom to the snake tail end 612*e*. With the foregoing routing of the actuation tail 611 and the snake tail 612, the snake loop 612*f* extends proximally from the first lateral side 623*a* of the anchor body 604 while free portions of the actuation tail 611 and snake tail 612 extend proximally from the second lateral side 623*b* of the anchor body 604. It should be appreciated that various modification and adaptations can be made to the repair assembly 601 while remaining within the scope of the present disclosure.

The manner in which the repair assembly 601 shown in FIG. 15A is adapted for tissue approximation will now be described with reference to FIGS. 15B-15E, in particularly according to an exemplary method for approximating a second anatomical structure 7 with respect to a first anatomical structure 5. For visualization purposes, the soft anchor 2 in these Figures is shown in the insertion configuration C1 (i.e., without the anchor being actuated into an anchored configuration); however, it should be appreciated that during tissue approximation the anchor 602 will have been actuated to an anchored configuration in which the anchor 602 bunches up, thereby causing the maximum length of the anchor 602 to decrease and the maximum width of the anchor 602 to increase, generally similar to the embodiments described above.

Figure 15B:
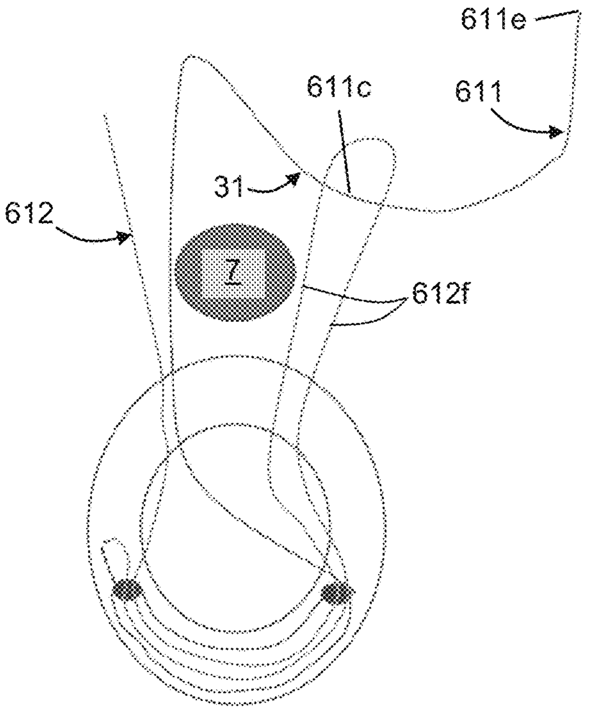
FIGS. 15B-15E are front plan views of the tissue repair assembly illustrated in FIG. 15A, shown in various stages of a process for approximating tissue, according to an embodiment of the present disclosure.

Referring now to FIG. 15B, the actuation tail end 611*e* is passed around the second anatomical structure 7 and through the snake loop 612*f*, thereby capturing or otherwise coupling a captured portion 611*c* of the actuation tail 611 with the snake loop 612*f*. This causes the snake loop 612*f* and the actuation tail 611 to form a shuttle loop 31 around the second anatomical structure 7.

Figure 15C:
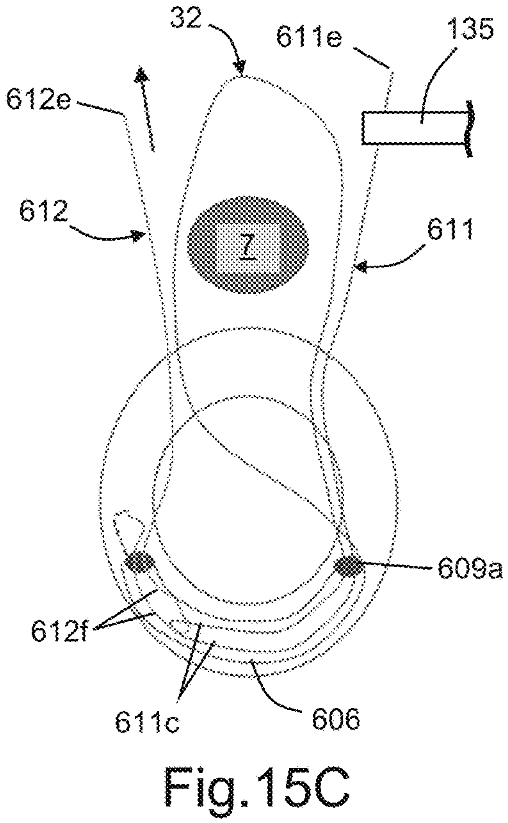

Referring now to FIG. 15C, the snake tail 612 is employed to shuttle the captured actuation tail portion 611*c* into the cannula 606. In particular, the snake tail end 612*e* is tensioned, which pulls the snake loop 612*f*, and the captured actuation tail portion 611*c* distally through the first proximal penetration 625*a*, and subsequently through the first distal penetration 624*a* and into the cannulation 607 through the first opening 609*a* of the cannula 606. During shuttling, the actuation tail end 611*e* can optionally be secured by a grasping tool 135 to prevent the actuation tail end 611*e* from decoupling from the snake loop 612*f*. After shuttling, the actuation tail 611 forms an approximation loop 32 around the second anatomical structure 7. Also after shuttling, the actuation tail 611 is pulled within the cannulation 607 through the first opening 609*a*, is captured by and doubles back round the snake loop 612*f*, and exits the cannulation 607 through the first opening 609*a* and extends to the actuation tail end 611*e*. In this manner, the repair assembly 601 can be characterized as providing a "double-stuff" actuation tail 611 within the cannulation 607, and thus also providing a double-stuff locking mechanism 626.

Figure 15D:
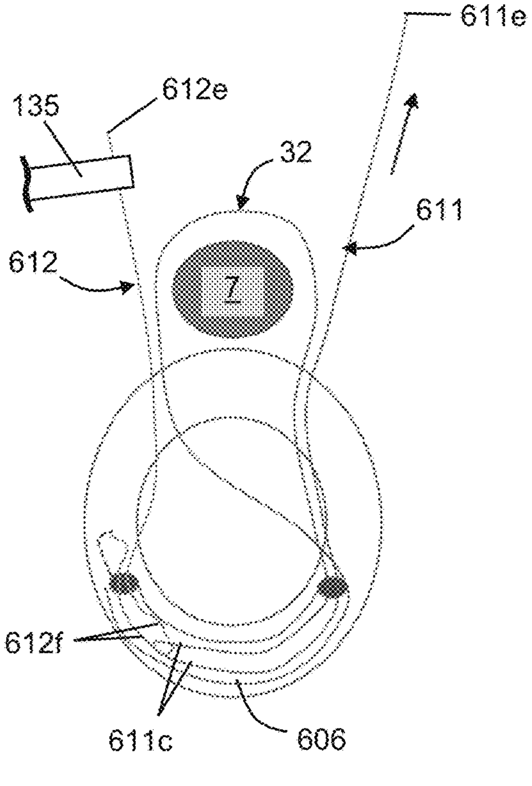

Referring now to FIG. 15D, when the snake loop 612*f* is inside the cannulation 607 and the snake tail end 612*e* is secured, which may optionally be aided by means such as a grasping tool 135, as shown, the snake loop 612*f* effectively forms a pully mechanism that operates upon the captured actuation tail portion 611*c* inside the cannulation 607, which pully mechanism allows the surgeon to pull the actuation tail end 611*e* to reduce the circumference of the approximation loop 32 and thereby approximate the second anatomical structure 7 with respect to the first anatomical structure 5. During tissue approximation, the tension applied to the actuation tail end 611*e* is transmitted along the actuation tail 611 to the cannula 606, which tensions the cannula 606 causing it perform one-way locking against the portions of the actuation tail 611 that are doubled through the cannulation 307. Because tension along the actuation tail 611 and the cannulation 606 is maintained after the second anatomical structure is satisfactorily approximated, the cannula 606 locks against the portions of the actuation tail 611 therein with sufficient force to retain the approximated position of the second anatomical structure with respect to the first anatomical structure 5.

Figure 15E:
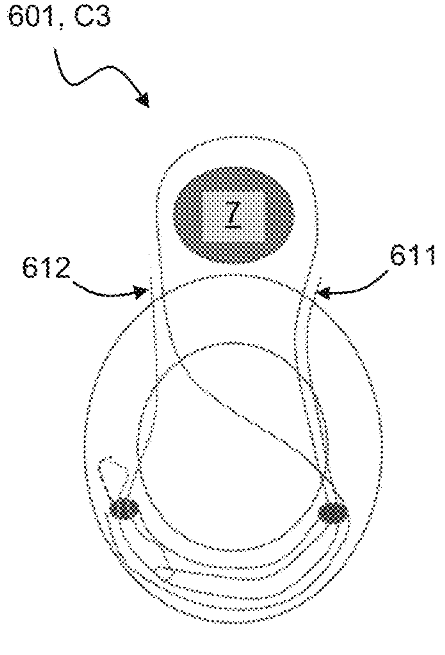

Referring now to FIG. 15E, when the second anatomical structure 7 is sufficiently approximated with respect to the anchor body 4 (and thus also with respect to the first anatomical structure 5), the free portions of the actuation tail 611 and the snake tail 612 can be trimmed. Optionally, one or both of the free portions of the actuation tail 611 and snake tail 612 can be tied-off to provide one or more secondary locking structures to the approximation loop 32 of the present embodiment. It should be appreciated that numerous additional and/or alternative steps can be performed to facilitate the foregoing exemplary technique for approximating tissue using the repair assembly 601.

It should be appreciated that the various parameters of the tissue repair assemblies 1, 201, 301, 401, 501, 601 described above, and their constituent soft anchors 2, 202, 302, 402, 502, 602, are provided as exemplary features for adapting a tissue repair assembly to approximate tissue in a manner providing the various benefits and advantages discussed above, such as, by way of non-limiting examples: using narrower-profile soft anchors for use within narrower bone holes; achieving wider, beneficial actuated anchor configurations (e.g., broader proximal anchor faces, proximal barrier-like anchor formations that resist pullout and resist proximal migration of the locking mechanism); and enhanced anchor tactile feedback, among other benefits and advantages. These parameters can be adjusted as needed without departing from the scope of the present disclosure.

It should also be appreciated that the size parameters disclosed above can be scaled upwards or downwards depending on the treatments needs of the patient, such as patient species, age, and treatment anatomy/location.

It should additionally be appreciated that in additional embodiments, the tissue repair assemblies 1, 201, 301, 401, 501, 601 described above can be provided in a kit that includes a plurality of interchangeable tissue repair assemblies and associated instruments, such as the instruments described above with reference to FIGS. 7A-8Q, such that the surgeon or other user can select the particular repair assembly for approximating a particular tissue according to specific treatments needs of the patient.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An assembly for anatomical approximation, wherein the assembly is configured to transition from an insertion configuration to an anchored configuration, the assembly comprising:

an anchor body constructed of suture and defining an anchor loop, the anchor body defining a length along a first direction and a width along a second direction that is substantially perpendicular to the first direction, wherein the anchor body is configured so that the length decreases and the width increases as the assembly transitions from the insertion configuration to the anchored configuration;

an actuation member that is constructed of suture and defines a first actuation portion and a second actuation portion, wherein the first actuation portion defines a locking mechanism within an interior passage defined by a distal portion of the anchor body, wherein the locking mechanism comprises a plurality of knot loops; and a snake member having a first snake portion and first and second snake tails, wherein, when the assembly is in the insertion configuration:

the first snake portion extends along the interior passage of the anchor body and through the plurality of knot loops, the second actuation portion and the first and second snake tails are exterior of the anchor body, and at least one of the second actuation portion and the first and second snake tails is configured to receive a tensile force for transitioning the assembly from the insertion configuration to the anchored configuration, and wherein a free end region of the second snake tail is configured to couple with a free end region of the second actuation portion, such that a free end region of the first snake tail is configured to be pulled to draw the free end region of the second actuation portion into and through the interior passage of the anchor body, so that:

when the assembly is in a third configuration, the second actuation portion:

1) is gripped by and slidable relative to the plurality of knot loops within the interior passage, and 2) defines an approximation loop located exterior of the anchor body for approximating tissue.

2. The assembly of claim 1, wherein the plurality of knot loops comprises a first knot loop and a second knot loop.

3. The assembly of claim 2, wherein the first and second knot loops are defined by respective portions of the first actuation portion that are bent into loops that double back and penetrate through the first actuation portion.

4. The assembly of claim 2, wherein the first knot loop and the second knot loop are spaced from each other at a knot loop spacing distance measured along a central axis of the anchor body, and the knot loop spacing distance is in a range of about 2.0 mm to about 7.0 mm.

5. The assembly of claim 4, wherein the knot spacing distance is in a range of about 3.5 mm to about 4.5 mm.

6. The assembly of claim 1, wherein the second actuation portion comprises first and second actuation tails that extend outside the anchor body from first and second locations of the anchor body, respectively, and the first and second actuation tails are spliced together extending from a splice insertion point to a splice end point, wherein the splice insertion point is located within a profile of the anchor loop with respect to the first and second directions.

7. The assembly of claim 1, wherein the actuation member enters the interior passage at a first location of the anchor body and exits the interior passage at a second location of the anchor body.

8. The assembly of claim 7, wherein a passage length measured between the first and second locations along a central axis of the anchor body is in a range of about 8.0 mm to about 16.0 mm.

9. The assembly of claim 8, wherein the passage length is in a range of about 11.0 mm to about 14.0 mm.

10. The assembly of claim 7, wherein the anchor body comprises suture fibers braided together in a circular braided construct.

11. The assembly of claim 7, wherein the actuation member penetrates the circular braided construct at the first and second locations.

12. The assembly of claim 7, wherein, when the assembly is in the insertion configuration, the snake member enters and exits the interior passage at the first and second locations, respectively.

13. The assembly of claim 7, wherein the distal portion of the anchor body extends from the a proximal-most one of the first and second locations to a distal end of the anchor body, and when the assembly is in the insertion configuration, the distal portion of the anchor body has a length along the first direction that is in a range of about 28% to about 32% of the length of the anchor body.

14. The assembly of claim 1, wherein the snake member is constructed of suture.

15. The assembly of claim 1, wherein the free end region of the second snake tail defines a snake loop for receiving at least part of the free end region of the second actuation portion for coupling the free end region of the second snake tail with the free end region of the second actuation portion.

16. The assembly of claim 15, wherein the snake loop is defined by an eye splice of two portions of the second snake tail.

* * * * *